US010098945B2

(12) United States Patent
Palese et al.

(10) Patent No.: US 10,098,945 B2
(45) Date of Patent: *Oct. 16, 2018

(54) GENETICALLY ENGINEERED SWINE INFLUENZA VIRUS AND USES THEREOF

(71) Applicants: Icahn School of Medicine at Mount Sinai, New York, NY (US); St. Jude Children's Research Hospital, Memphis, TN (US); The United States of America, As Represented by the Secretary of Agriculture, Washington, DC (US)

(72) Inventors: Peter Palese, New York, NY (US); Adolfo Garcia-Sastre, New York, NY (US); Richard J. Webby, Memphis, TN (US); Juergen A. Richt, Ames, IA (US); Robert G. Webster, Memphis, TN (US); Kelly M. Lager, Colo, IA (US)

(73) Assignees: Icahn School of Medicine at Mount Sinai, New York, NY (US); St. Jude Children's Research Hospital, Memphis, TN (US); The United States of America, As Represented by the Secretary of Agriculture, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/375,664

(22) Filed: Dec. 12, 2016

(65) Prior Publication Data

US 2017/0151324 A1 Jun. 1, 2017

Related U.S. Application Data

(62) Division of application No. 14/636,651, filed on Mar. 3, 2015, now Pat. No. 9,549,975, which is a division of application No. 13/304,175, filed on Nov. 23, 2011, now Pat. No. 8,999,352, which is a division of application No. 11/628,292, filed as application No. PCT/US2005/019382 on Jun. 1, 2005, now Pat. No. 8,124,101.

(60) Provisional application No. 60/576,418, filed on Jun. 1, 2004.

(51) Int. Cl.
*A61K 39/145* (2006.01)
*C12N 7/00* (2006.01)
*A61K 39/00* (2006.01)

(52) U.S. Cl.
CPC .............. *A61K 39/145* (2013.01); *C12N 7/00* (2013.01); *A61K 2039/5254* (2013.01); *A61K 2039/5256* (2013.01); *A61K 2039/552* (2013.01); *C12N 2760/16034* (2013.01); *C12N 2760/16121* (2013.01); *C12N 2760/16171* (2013.01)

(58) Field of Classification Search
None
See application file for complete search history.

(56) References Cited

U.S. PATENT DOCUMENTS

| | | | |
|---|---|---|---|
| 4,071,618 A | 1/1978 | Konobe et al. |
| 4,567,147 A | 1/1986 | Ooi et al. |
| 4,659,569 A | 4/1987 | Mitsuhashi et al. |
| 4,693,981 A | 9/1987 | Wiesehan et al. |
| 5,106,619 A | 4/1992 | Wiesehan et al. |
| 5,166,057 A | 11/1992 | Palese et al. |
| 5,674,502 A | 10/1997 | Ennis et al. |
| 5,766,601 A | 6/1998 | Ennis et al. |
| 5,786,199 A | 7/1998 | Palese et al. |
| 5,820,871 A | 10/1998 | Palese et al. |
| 5,854,037 A | 12/1998 | Palese et al. |
| 5,866,694 A | 2/1999 | Katinger et al. |
| 5,882,650 A | 3/1999 | Ennis |
| 5,891,705 A | 4/1999 | Budowsky et al. |
| 6,146,642 A | 11/2000 | Garcia-Sastre |
| 6,146,873 A | 11/2000 | Kistner et al. |
| 6,162,432 A | 12/2000 | Wallner et al. |
| 6,300,090 B1 | 10/2001 | Steinman et al. |
| 6,326,151 B1 | 12/2001 | Katze et al. |
| 6,468,544 B1 | 10/2002 | Egorov et al. |
| 6,544,785 B1 | 4/2003 | Palese et al. |
| 6,573,079 B1 | 6/2003 | Palese et al. |

(Continued)

FOREIGN PATENT DOCUMENTS

| | | |
|---|---|---|
| CN | 104830811 | 8/2015 |
| DE | 100 20 505 | 10/2001 |

(Continued)

OTHER PUBLICATIONS

"Commentary: 1933 Human Sequences in 2004 H1N1 Korean Swine Isolates", dated Dec. 4, 2004; http://www.recombinomics.com/News/12040402/1933_2004_1N1.html.

(Continued)

*Primary Examiner* — Benjamin P Blumel
(74) *Attorney, Agent, or Firm* — Jones Day

(57) ABSTRACT

The present invention relates, in general, to attenuated swine influenza viruses having an impaired ability to antagonize the cellular interferon (IFN) response, and the use of such attenuated viruses in vaccine and pharmaceutical formulations. In particular, the invention relates to attenuated swine influenza viruses having modifications to a swine NS1 gene that diminish or eliminate the ability of the NS1 gene product to antagonize the cellular IFN response. These viruses replicate in vivo, but demonstrate decreased replication, virulence and increased attenuation, and therefore are well suited for use in live virus vaccines, and pharmaceutical formulations.

34 Claims, 11 Drawing Sheets

Figure 1A:
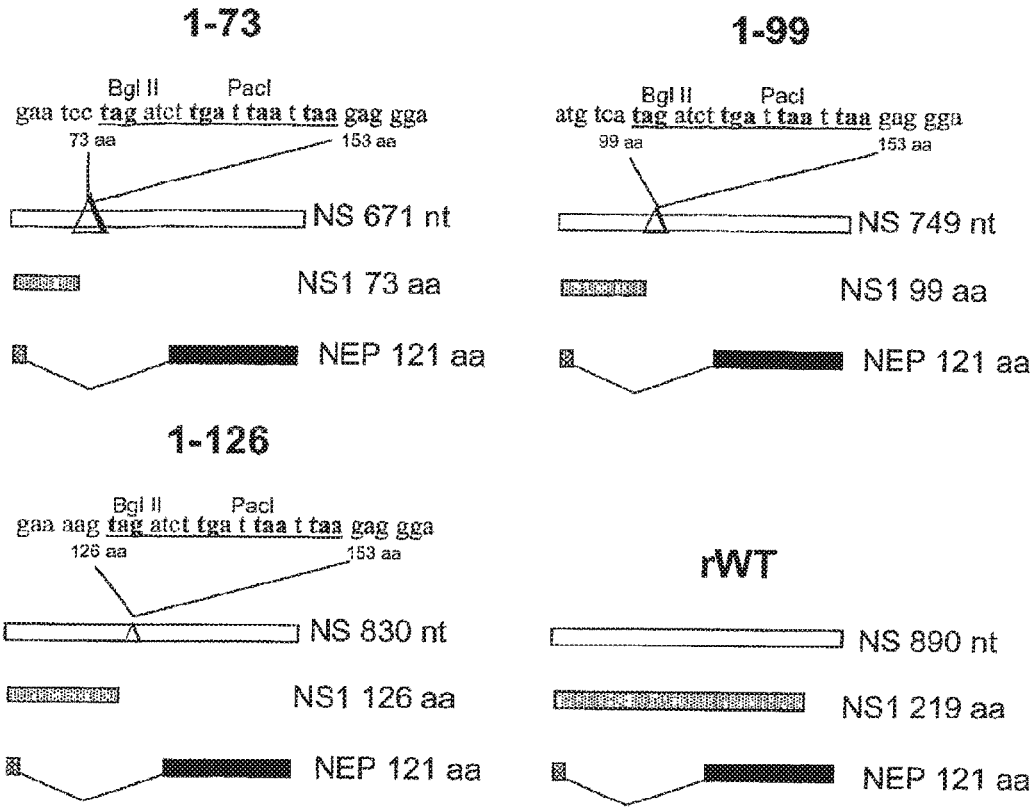

Specification includes a Sequence Listing.

(56) References Cited

U.S. PATENT DOCUMENTS

| | | | |
|---|---|---|---|
| 6,635,246 B1 | 10/2003 | Barrett et al. |
| 6,635,416 B2 | 10/2003 | Palese et al. |
| 6,649,372 B1 | 11/2003 | Palese et al. |
| 6,669,943 B1 | 12/2003 | Palese et al. |
| 6,673,591 B2 | 1/2004 | Lau |
| 6,686,190 B2 | 2/2004 | Lau |
| 6,800,288 B2 | 10/2004 | Ferko et al. |
| 6,852,522 B1 | 2/2005 | Palese et al. |
| 6,866,853 B2 | 3/2005 | Egorov et al. |
| 6,884,414 B1 | 4/2005 | Palese et al. |
| 7,060,430 B2 | 6/2006 | Palese et al. |
| 7,132,271 B2 | 11/2006 | Lau |
| 7,344,722 B1 | 3/2008 | Maassab et al. |
| 7,442,527 B2 | 10/2008 | Palese et al. |
| 7,494,659 B2 | 2/2009 | Katinger et al. |
| 7,494,808 B2 | 2/2009 | Palese et al. |
| 7,507,411 B2 | 3/2009 | Zhou et al. |
| 7,588,768 B2 | 9/2009 | Palese et al. |
| 7,833,774 B2 | 11/2010 | Palese et al. |
| 8,012,490 B2 | 9/2011 | Palese et al. |
| 8,057,803 B2 | 11/2011 | Palese et al. |
| 8,124,101 B2 | 2/2012 | Palese et al. |
| 8,137,676 B2 | 3/2012 | Palese et al. |
| 8,282,937 B2 | 10/2012 | Maassab et al. |
| 8,999,352 B2 | 4/2015 | Palese et al. |
| 9,549,975 B2 | 1/2017 | Palese et al. |
| 2004/0253273 A1 | 12/2004 | Paleso et al. |
| 2007/0122430 A1 | 5/2007 | Shneider et al. |
| 2008/0234175 A1 | 9/2008 | Montelione et al. |
| 2009/0123495 A1 | 5/2009 | Sachet et al. |
| 2009/0203114 A1 | 8/2009 | Palese et al. |
| 2010/0158942 A1 | 6/2010 | Palese et al. |
| 2010/0233785 A1 | 9/2010 | Brandt et al. |
| 2012/0122185 A1 | 5/2012 | Palese et al. |
| 2012/0258134 A1 | 10/2012 | Palese et al. |

FOREIGN PATENT DOCUMENTS

| | | | |
|---|---|---|---|
| EP | | 702085 A1 | 3/1996 |
| EP | | 780475 A1 | 6/1997 |
| EP | | 780475 B1 | 6/1997 |
| EP | | 1085904 | 12/1999 |
| EP | 1 086 207 B1 | | 1/2007 |
| EP | | 1098961 | 1/2008 |
| JP | | 59-39831 | 3/1984 |
| WO | WO 1993/006866 | | 4/1993 |
| WO | WO 1996/010632 | | 4/1996 |
| WO | WO 1996/034625 | | 11/1996 |
| WO | WO 1997/006270 | | 2/1997 |
| WO | WO 1997/008292 | | 3/1997 |
| WO | WO 1997/012032 | | 4/1997 |
| WO | WO 1998/002530 | | 1/1998 |
| WO | WO 1998/013501 | | 4/1998 |
| WO | WO 1998/053078 | | 11/1998 |
| WO | WO 1999/002657 | | 1/1999 |
| WO | WO 1999/015672 | | 4/1999 |
| WO | WO 1999/064068 | | 12/1999 |
| WO | WO 1999/064570 | | 12/1999 |
| WO | WO 1999/064571 | | 12/1999 |
| WO | WO 2001/004333 | | 1/2001 |
| WO | WO 2001/064860 | | 9/2001 |
| WO | WO 2001/077394 | | 10/2001 |
| WO | WO 2002/024876 | | 3/2002 |
| WO | WO 2006/083286 | | 8/2006 |
| WO | WO 2006/088481 | | 8/2006 |
| WO | WO 2007/064802 | | 6/2007 |
| WO | WO 2016/037113 | | 3/2016 |
| WO | WO 2016/137929 | | 9/2016 |

OTHER PUBLICATIONS

"Commentary: WSB/33 H1 in Fatally Infected Korean Swine Lungs", dated Apr. 25, 2005; http://www.recombinomics.com/News/04280501/WSN33_Fatal_Swine_Lung.html.

Aebi, 1989, "cDNA structures and regulation of two interferon-induced human Mx proteins." Mol. Cell. Biol. 11:5062.

Aoki K et al., 1996, "Differential sensitivity of two related viruses, Newcastle disease virus and Sendai virus, to interferon in mouse Had-2 cells selective inhibition of translation of NDV mRNA.", Arch Virol.;141(10):1847-62.

Aragon et al., 2000, "Eukaryotic translation initiation factor 4GI is a cellular target for NS1 protein, a translational activator of influenza virus." Mol. Cell. Biol. 20:6259-6268.

Arvin et al., 2006, "New viral vaccines." Virology, vol. 344:240-249.

Baez M et al., 1980, "Complete nucleotide sequence of the influenza A/PR/8/34 virus NS gene and comparison with the NS genes of the A/Udorn/72 and A/FPV/Rostock/34 strains", Nucleic Acids Res. Dec. 11;8(23):5845-58.

Baskin et al., 2007, Functional genomic and serological analysis of the protective immune response resulting from vaccination of macaques with an NS1-truncated influenza virus. J Virol. 81(21):11817-27.

Basler et al., 2000, "The Ebola virus VP35 protein functions as a type I IFN antagonist." Proc Natl Acad Sci U S A. Oct. 24;97(22):12289-94.

Beatrice et al., 1980, "Immunogenicity in mice of temperature-sensitive mutants of vesicular stomatitis virus: early appearance in bronchial secretions of an interferon-like inhibitor", J Gen Virol.; 47:529-533.

Beattie et al., 1995, "Reversal of the Interferon-Sensitive Phenotype of a Vaccinia Virus Lacking E3L by Expression of the Reovirus S4 Gene," J. Virology 69(1):499-505.

Belardelli & Gresser, 1996, "The neglected role of type I interferon in the T-cell response: implications for its clinical use." Immunol. Today 17:369-372.

Bergmann et al., 2000, "Influenza virus NS1 protein counteracts PKR-mediated inhibition of replication." Virol. Jul.;74(13):6203-6.

Bossert et al., 2002, "Respiratory Syncytial Virus (RSV) Nonstructural (NS) Proteins as Host Range Determinants: a Chimeric Bovine RSV with NS Genes from Human RSV Is Attenuated in Interferon-Competent Bovine Cells", J. of Virology 76:4287-93.

Bouloy et al., 2001, "Genetic evidence for an interferon-antagonistic function of rift valley fever virus nonstructural protein NSs." J Virol. Feb.;75(3):1371-7.

Briedis et al., 1981, "Influenza B virus genome: sequences and structural organization of RNA segment 8 and the mRNAs coding for the $NS_1$ and $NS_2$ proteins." J Virol. 42(1):186-93.

Briscoe et al., 1996, Kinase-negative mutants of JAK1 can sustain interferon-gamma-inducible gene expression but not an antiviral state, EMBO J. 15:799-809.

Buonagurio Da et al., 1986, "Evolution of human influenza A viruses over 50 years: rapid, uniform rate of change in NS gene", Science. May 23;232(4753):980-2.

Buonagurio et al., 1984, "Analysis of an influenza A virus mutant with a deletion in the NS segment," J Virol. 49:418-425.

Butterfield et al., 1978, "Vaccination for fowl plague", Am J Vet Res. Apr.; 39(4):671-674.

Chambers et al., 2009, "Influenza A viruses with truncated NS1 as modified live virus vaccines: Pilot studies of safety and efficacy in horses," Equine Veterinary Journal 41:87-92.

Chang et al., 1992,"The E3L gene of vaccinia virus encodes an inhibitor of the interferon-induced, double-stranded RNA-dependent protein kinase.", Proc Natl Acad Sci U S A. Jun. 1;89(11):4825-9.

Chen Z et al., 1999, "Influenza A virus NS1 protein targets poly(A)-binding protein II of the cellular 3'-end processing machinery", EMBO J. Apr. 15;18(8):2273-83.

Chinese Office Action of Chinese application No. 201210111286.1 dated Aug. 6, 2013.

Chinese Patent Application No. 200580026048.9, Translation of Second Office Action dated Apr. 2, 2010.

Clemens and Elia, 1997, "The Double Stranded RNA-Dependent Protein Kinase PKR: Structure and Function", Journal of Interferon and Cytokine Research, 17:503-524.

(56) References Cited

OTHER PUBLICATIONS

Clemens et al., 1997, "The Double Stranded RNA-Dependent Protein Kinase PKR: Structure and Function", in Journal of Interferon and Cytokine Research; 17:503-24.
Constantinescu et al., 1995, "Expression and signaling specificity of the IFNAR chain of the type I interferon receptor complex." Proc. Natl. Acad. Sci. USA 92:10487-91.
Cossins et al., 1993, "Precise prediction of a Kk-restricted cytotoxic T cell epitope in the NS1 protein of influenza virus using an MHC allele-specific motif.", Virology. Mar.;193(1):289-95.
Crowe JE, 1998, "Immune responses of infants to infection with respiratory viruses and live attenuated respiratory virus candidate vaccines", Vaccine. Aug.; 16(14/15):1423-1432.
Cruse et al, 2003, *Illustrated Dictionary of Immunology*, 2nd Edition, Cruse et al. Editors, CRC Press, pp. 367, under "Knockout Gene".
Da Silva et al., 2006, Vaccines under development: group B streptococcus, herpes-zoster, HIV, malaria and dengue, Jornal de Pediatria, vol. 82, Suppl. 3, pp. S115-S124.
De La Luna S et al., 1995, "Influenza virus NS1 protein enhances the rate of translation initiation of viral mRNAs", J Virol. Apr.;69(4):2427-33.
Desmyter J et al., 1968, "Defectiveness of interferon production and of rubella virus interference in a line of African green monkey kidney cells (Vero)", J Virol. Oct.;2(10):955-61.
Diaz MO et al., 1988, "Homozygous deletion of the alpha- and beta 1-interferon genes in human leukemia and derived cell lines", Proc Natl Acad Sci U S A. Jul.;85(14):5259-63.
Didcock et al., 1999, "The V Protein of Simian Virus 5 Inhibits Interferon Signalling by Targeting STAT1 for Proteasome-Mediated Degradation", J. of Virology, 73(12): 9928-9933.
Donelan et al., 2003, A recombinant influenza A virus expressing an RNA-binding-defective NS1 protein induces high levels of beta interferon and is attenuated in mice. J Virol. Dec.;77(24):13257-66.
Donelan et al., 2004, "The N- and C-terminal domains of the NS1 protein of influenza B virus can independently inhibit IRF-3 and beta interferon promoter activation." J Virol. Nov.;78(21):11574-82.
Dulbecco R, 1988, "Multiplication and Genetics of Animal Viruses", Ch. 48, in Dulbecco et al., Editors, *Virology*, pp. 77-79.
Durbin JE et al., 1996, "Targeted disruption of the mouse Stat1 gene results in compromised innate immunity to viral disease", Cell. Feb. 9;84(3):443-50.
Easterday, 1980, "Animals in the Influenza World." Philos Trans R Soc Lond B Biol Sci 288:433-7.
Efferson et al., 2005, "Stimulation of human T cells by an influenza A vector expressing a CTL epitope from the HER-2/neu protooncogene results in higher numbers of antigen-specific TCRhi cells than stimulation with peptide." Divergent roles of IL-2 and IL-15. Anticancer Res. Mar.-Apr.;25(2A):715-24.
Efferson et al., 2006, "Prostate tumor cells infected with a recombinant influenza virus expressing a truncated NS1 protein activate cytolytic CD8+ cells to recognize noninfected tumor cells." J Virol. 80(1):383-394.
Egorov A et al., 1994, "The NS gene—a possible determinant of apathogenicity of a cold-adapted donor of attenuation A /Leningrad/134/47/57 and its reassortants." Vopr Virusol. Sep.-Oct.;39(5):201-5. Russian.
Egorov A et al., 1998, "Transfectant influenza A viruses with long deletions in the NS1 protein grow efficiently in Vero cells", J Virol. Aug.;72(8):6437-41.
Egorov AY et al., 1997, "Generation of influenza A transfectant viruses containing deletions of the carboxyl-terminal part of the NS1 protein", in *Emergence and Re-emergence of Negative Strand Viruses, Tenth International Conference on Negative Strand Viruses*. Dublin, Ireland Abstract No. 108, p. 104.
Egorov et al., 1997, "Generation of Influenza A Transfectant Viruses Containing Deletions in the NS1 Protein", Institute of Applied Microbiology, in Emergence and Re-emergence of Negative Strand Viruses, Tenth International Conference on Negative Strand Viruses. Sep. 21-26, Dublin, Ireland. POSTER.

Enami K et al., 1994, "Influenza virus NS1 protein stimulates translation of the M1 protein", J Virol. Mar.;68(3):1432-7.
Enami M and Palese P., 1991, "High-efficiency formation of influenza virus transfectants", J Virol.;65(5):2711-3.
Enami M et al., 1991, "An influenza virus containing nine different RNA segments", Virology 185(1):291-8.
European Office Action of European application No. 05856779.3-1410 dated Mar. 20, 2013.
European Patent Application No. 05 856 778.5, Communication pursuant to Article 94(3) EPC, dated Apr. 7, 2010.
European Patent Application No. 05 856 778.5; Response to Apr. 17, 2010 Communication pursuant to Article 94(3) EPC, dated Oct. 15, 2010.
European Patent Application No. 05 856 779.3; Communication pursuant to Article 94(3) EPC, dated Oct. 6, 2010.
European patent application No. 99927445: Communication pursuant to Article 96(2) EPC, dated Nov. 14, 2007.
European patent application No. 99927445: Communication pursuant to Article 96(2) EPC, dated May 26, 2006.
European patent application No. 99927445: Communication pursuant to Article 96(2) EPC, dated Mar. 21, 2005.
European patent application No. 99927445: European Search Report, dated Nov. 11, 2004.
European patent application No. 99927445: Invitation pursuant to Article 94(3) EPC and Rule 71(1) EPC, dated Nov. 9, 2009.
European patent application No. 99927445: Response to Invitation pursuant to Article 94(3) EPC and Rule 71(1) EPC, dated May 10, 2010.
European patent application No. 99927445: Response to Mar. 21, 2005 Communication pursuant to Article 96(2) EPC, dated Sep. 30, 2005.
European patent application No. 99927445: Response to May 26, 2006 Communication pursuant to Article 96(2) EPC, dated Dec. 5, 2006.
European patent application No. 99927445: Response to Nov. 14, 2007 Communication pursuant to Article 96(2) EPC, dated May 26, 2008.
European Patent Application No. EP 05 856 778.5, Communication pursuant to Article 94(3) EPC, dated Jun. 28, 2011.
European Patent Application No. EP 05 856 779.3, Response to Communication pursuant to Article 94(3) EPC, dated Apr. 15, 2011.
Falcon et al., 2005, "Attenuation and immunogenicity in mice of temperature-sensitive influenza viruses expressing truncated NS1 proteins." J Gen Virol. Oct.;86(Pt 10):2817-21.
Fenner et al. 1974. *The Biology of Animal Viruses* $2^{nd}$ Ed. New York: Academic Press. 42-43.
Ferko et al., 2004, "Immunogenicity and protection efficacy of replication-deficient influenza A viruses with altered NS1 genes." J Virol. 78(23):13037-13045.
Fernandez-Sesma et al., 2006, "Influenza virus evades innate and adaptive immunity via the NS1 protein." J Virol. 80(13):6295-304.
Finn, OL 2003, "Cancer vaccines: between the idea and the reality." Nature 3:630-641.
Floyd-Smith et al., 1981, "Interferon Action: RNA Cleavage Pattern of a (2'-5') Oligoadenylate-Dependent Endonuclease," Science; 212:1030-2.
Fodor E et al., 1998, "Attenuation of influenza A virus mRNA levels by promoter mutations", J Virol. 72(8):6283-90.
Fodor et al., 1999, "Rescue of influenza A virus from recombinant DNA." J. Virol 73:9679-9682.
Fortes P et al., 1994, "Influenza virus NS1 protein inhibits pre-mRNA splicing and blocks mRNA nucleocytoplasmic transport", EMBO J. Feb. 1;13(3):704-12.
Garcia-Sastre A et al., 1998, "Influenza A virus lacking the NS1 gene replicates in interferon-deficient systems", Virology. Dec. 20;252(2):324-30.
Garcia-Sastre A et al., 1998, "The role of interferon in influenza virus tissue tropism", J Virol. Nov.;72(11):8550-8.
Garcia-Sastre A. 2001, "Inhibition of interferon-mediated antiviral responses by influenza A viruses and other negative-strand RNA viruses." Virology. 279(2):375-384.
Garcia-Sastre et al., 1994, "Introduction of foreign sequences into the genome of influenza A virus," Dev Biol Stand. 82:237-46.

(56) References Cited

OTHER PUBLICATIONS

Garcia-Sastre et al., 2002, "Mechanisms of inhibition of the host interferon alpha/beta-mediated antiviral responses by viruses." Microbes Infect 4:647-55.
Garcin et al., 1999, "Sendai Virus C Proteins Counteract the Interferon-Mediated Induction of an Antiviral State", J. Virology 73(8): 6559-6565.
Geiss et al., 2002, "Cellular transcriptional profiling in influenza A virus-infected lung epithelial cells: the role of the nonstructural NS1 protein in the evasion of the host innate defense and its potential contribution to pandemic influenza." Proc Natl Acad Sci U S A. Aug. 6;99(16):10736-41.
Genbank Accession No. AB116564 (Sus scrofa stat1 mRNA for signal transducer and activator of transcription 1, complete cds) Dec. 27, 2003.
Genbank Accession No. AF001662 (Influenza A virus (A/eq/Newmarket/D63/79(H3N8)) nonstructural proteins NS1 and NS2 (NS) gene, complete cds) Aug. 12, 1998.
Genbank Accession No. AF001663 (Influenza A virus (A/eq/Newmarket/1/77(H7N7)) nonstructural proteins NS1 and NS2 (NS) gene, complete cds) Aug. 12, 1998.
Genbank Accession No. AF001664 (Influenza A virus (A/eq/Kentucky/1/88(H3N8)) nonstructural proteins NS1 and NS2 (NS) gene, complete cds) Aug. 12, 1998.
Genbank Accession No. AF001665 (Influenza A virus (A/eq/LaPlata/1/88(H3N8)) nonstructural proteins NS1 and NS2 (NS) gene, complete cds) Aug. 12, 1998.
Genbank Accession No. AF001666 (Influenza A virus (A/eq/Yvelines/2136/89(H3N8)) nonstructural proteins NS1 and NS2 (NS) gene, complete cds) Aug. 12, 1998.
Genbank Accession No. AF001667 (Influenza A virus (A/eq/Alaska/1/91(H3N8)) nonstructural proteins NS1 and NS2 (NS) gene, complete cds), Aug. 12, 1998.
Genbank Accession No. AF001668 (Influenza A virus (A/eq/Arundel/12369/91(H3N8)) nonstructural proteins NS1 and NS2 (NS) gene, complete cds), Aug. 12, 1998.
Genbank Accession No. AF001669 (Influenza A virus (A/eq/Roma/5/91(H3N8)) nonstructural proteins NS1 and NS2 (NS) gene, complete cds), Aug. 12, 1998.
Genbank Accession No. AF001670 (Influenza A virus (A/eq/Hong Kong/1/92(H3N8)) nonstructural proteins NS1 and NS2 (NS) gene, complete cds), Aug. 12, 1998.
Genbank Accession No. AF001671 (Influenza A virus (A/eq/Kentucky/92(H3N8)) nonstructural proteins NS1 and NS2 (NS) gene, complete cds.), Aug. 12, 1998.
Genbank Accession No. AF001672 (Influenza A virus A/eq/Lambourn/22778/92(H3N8)) nonstructural proteins NS1 and NS2 (NS) gene, complete cds.), Aug. 12, 1998.
Genbank Accession No. AF001673 (Influenza A virus (A/eq/LaPlata/93(H3N8)) nonstructural proteins NS1 and NS2 (NS) gene, complete cds), Aug. 12, 1998.
Genbank Accession No. AJ293939 (A/swine/Italy/13962/95 (H3N2)), Nov. 14, 2006.
Genbank Accession No. AJ344041(A/swine/Cotes d'Armor/1121/00(H1N1))/13962/95 (H3N2)), Nov. 14, 2006.
Genbank Accession No. AJ430785 (Influenza A virus (A/equi-2/Ludhiana/87(H3N8)) genomic RNA for nonstructural protein (NS1 gene), isolate A/equi-2/Ludhiana/87(H3N8), Apr. 15, 2005.
Genbank Accession No. AY328471 (Influenza A virus (A/equine/Grobois/1/98(H3N8)) nonstructural protein NS1 mRNA, complete cds), Jul. 23, 2003.
Genbank Accession No. M65020 (Influenza A virus (A/equine/Jilin/1/1989(H3N8)) NS2 protein (NS2) and NS1 protein (NS1) genes, complete cds) May 23, 2006.
Genbank Accession No. NM_213769 (Sus scrofa signal transducer and activator of transcription 1 (STAT1), mRNA) Dec. 9, 2003.
Genbank Accession No. U49486 (Influenza A virus (A/equine/London/1416/1973(H7N7)) nonstructural protein NS2 (NS) gene, partial cds, alternatively spliced; and nonstructural protein NS1 (NS) gene, partial cds) Apr. 16, 2006.
Genbank Accession No. U49487 (Influenza A virus (A/equine/Tennessee/5/1986(H3N8)) nonstructural protein NS2 (NS) gene, partial cds, alternatively spliced; and nonstructural protein NS1 (NS) gene, partial cds) Apr. 16, 2006.
Genbank Accession No. U49489 (Influenza A virus (A/equine/Prague/1/1956(H7N7)) nonstructural protein NS2 (NS) gene, partial cds, alternatively spliced; and nonstructural protein NS1 (NS) gene, partial cds) Apr. 16, 2006.
Genbank Accession No. X80060 (Influenza A virus (A/equine 2/Suffolk/89(H3N8)) NS1 gene), Apr. 18, 2005.
Gonzalo et al., 1999, "Enhanced CD8+ T cell response to HIV1 env by combined immunization with influenza and vaccinia virus recombinants." Vaccine. Feb. 26;17(7-8):887-92.
Goodpasture et al., 1931, "The cultivation of vaccine and other viruses in the chorioallantoic membrane of chick embryos", Science.; 74(1919):371-372.
Gorse & Belshe, 1990, "Enhancement of anti-influenza A virus cytotoxicity following influenza A virus vaccination in older, chronically ill adults. "J. Clin. Microbiol. 28:2539-2550.
Gorse et al., 1995, "Increased anti-influenza A virus cytotoxic T cell activity following vaccination of the chronically ill elderly with live attenuated or inactivated influenza virus vaccine." J. Infect Dis 172:1-10.
Gotoh et al., 1999, "Knockout of the Sendai Virus C Gene Eliminates the Viral Ability to Prevent the Interferon-α/β-Mediated Responses." FEBS Letters 459:205-210.
Hackett CJ et al., 1992, "Influenza virus infection elicits class II major histocompatibility complex-restricted T cells specific for an epitope identified in the NS1 non-structural protein.", J Gen Virol. Jun.;73 ( Pt 6):1339-43.
Haller et al., 1980, "Host gene influences sensitivity to interferon action selectively for influenza virus", Nature. Feb. 14;283(5748):660-2.
Haller ,1981, "Inborn resistance of mice to orthomyxoviruses", Curr Top Microbiol Immunol. 92:25-52.
Haller et al., 1986, "Genetic resistance to influenza virus in wild mice", Curr Top Microbiol Immunol. 127:331-7.
Haller et al., 1998, "Mx Proteins: Mediators of Innate Resistance to RNA Viruses", Rev. Sci. Tech. Off. Int. Epiz., 17(1):220-230.
Hamzawi et al., 1981, "Antigenicity in hamsters of inactivated vaccines prepared from recombinant influenza viruses." J Hyg (Lond). 87(3):453-64. (Abstract only cited).
Hatada E et al., 1992, "Binding of influenza A virus NS1 protein to dsRNA in vitro", J Gen Virol. Dec.;73 (Pt 12):3325-9.
He et al., 1997, "The 34.5 Protein of Herpes Simplex Virus 1 Complexes With Protein Phosphatase 1α to Dephosphoiylate the α subunit of the eukaryotic translation initiation factor 2 and preclude the shutoff of protein synthesis by double stranded RNA-activated protein kinase", Proc. Natl. Acad. Sci. USA, 94:843-848.
Hengel et al., 2005, "Viruses know it all: New insights into IFN networks," Trends in Immunology 26:396-401.
Hoffmann et al., 2000, "A DNA transfection system for generation of influenza A virus from eight plasmids," Proc. Natl. Acad. Sci. U. S. A. 97(11):6108-13.
Holmquist et al., 1979, "Affinity chromatography of influenza virus on immobilized alpha and beta-ketosides of neraminic acid derivatives" in Acta Pathol Microb. Scand [B]; 87B(2):129-35 (Abstract Only).
International Preliminary Examination Report PCT/US99/13139, dated Sep. 12, 2000.
International Preliminary Examination Report PCT/US99/13142, dated Aug. 9, 2000.
International Preliminary Examination Report PCT/US99/13144, dated Nov. 28, 2000.
International Preliminary Report on Patentability PCT/US01/11543, dated Mar. 5, 2002.
International Preliminary Report on Patentability PCT/US05/019382, dated Dec. 28, 2006.
International Preliminary Report on Patentability PCT/US05/019383, dated Aug. 21, 2007.
International Search Report PCT/US05/19382, dated Oct. 25, 2006.
International Search Report PCT/US05/19383, dated Nov. 8, 2006.
International Search Report PCT/US99/13139, dated Oct. 28, 1999.

(56) References Cited

OTHER PUBLICATIONS

International Search Report PCT/US99/13142, dated Oct. 21, 1999.
International Search Report PCT/US99/13144, dated Oct. 21, 1999.
Ito et al., 1998. "Molecular basis for the generation in pigs of influenza A viruses with pandemic potential", J. Virol., 72:7367-7373.
Japanese Office Action of Japanese application No. 2010-218868 dated Apr. 16, 2013.
Karasin et al., 2000 "Genetic characterization of an H1N2 influenza virus isolated from a pig in Indiana." J. Clin. Microbiol. 38:2453-2456.
Karasin et al., 2000, "Genetic characterization of H3N2 influenza viruses isolated from pigs in North America, 1977-1999: evidence for wholly human and reassortant virus genotypes." Virus Res. 68:71-85.
Karasin et al., 2000, "Isolation and characterization of H4N6 avian influenza viruses from pigs with pneumonia in Canada." J biol 74:9322-9327.
Karasin et al., 2002, "Genetic characterization of H1N2 influenza A viruses isolated from pigs throughout the United States. "J. Clin. Microbiol. 40:1073-9.
Katinger et al., 1997, "Attenuated influenza virus as a vector for mucosal immunization against HIV-1.", Vaccine 97: 315-319.
Khiabanian et al., 2009, "Reassortment patterns in swine influenza viruses," PLoS One, 4:e7366.
Kida et al., 1994, "Potential for transmission of avian influenza viruses to pigs." J. Gen Virol. 75:2183-8.
Kingsbury, 1991, "Orthomyxoviridae and their replication" in *Fields Virology*, Lippincott-Raven P.A., pp. 527-541.
Kochs et al., 2007, Multiple anti-interferon actions of the influenza A virus NS1 protein. J Virol. Jul.;81(13):7011-21.
Komatsu et al., 2000, "Sendai Virus Blocks Alpha Interferon Signaling to Signal Transducers and Activators of Transcription", J. Virology, 74(5): 2477-2480.
Krishnan et al., 1997, "Kinase-deficient forms of Jak1 and Tyk2 inhibit interferon alpha signaling in a dominant manner." in Eur. J. Biochem.; 247:298-305.
Krug and Soeiro, 1975, "Studies on the intranuclear localization of influenza virus-specific proteins", Virology 64: 378-87.
Krug, 1995, "Chapter 8. Unique Functions of the NS1 Protein" in *Textbook of Influenza*, Nicholson et al. (eds.), pp. 82-92.
Krystal M, et al., 1983, "Sequential mutations in the NS genes of influenza virus field strains." J Virol 45(2):547-54.
Kuwano et al., 1988, "HA2 subunit of influenza A H1 and H2 subtype viruses induces a protective cross-reactive cytotoxic T lymphocyte response.", J Immunol. Feb. 15;140(4):1264-8.
Kuwano, K et al., 1990, "Cross-reactive protection against influenza A virus infections by an NS1-specific CTL clone." Virology. Sep.;178(1):174-9.
Lamb & Choppin, 1983, "The gene structure and replication of influenza virus." Annual Rev Biochem 52:467-506.
Landolt et al., 2003, "Comparison of the Pathogenesis of Two Genetically Different H3N2 Influenza A Viruses in Pigs." : J Clin Microb. 41(5):1936-1941.
Lapidus, 1969, "Purification and Concentration of Influenza Types A and B by Chromatography on Calcium Phosphate." Appl. Microb 17(4):504-506.
Lewis, 1985 Induction of anti-viral activity and specific enzymes in cell-lines derived from interferon-resistant, thymidine kinase deficient mouse L-929 cells, Prog Clin Biol Res 202:325-332; p. 325.
Li & Rhode, 1990, "Mutation of lysine 405 to serine in the pars ovirus H-1 NS1 abolishes its functions for viral DNA replication, late promoter trans activation, and cytotoxicity," J. Virol 10:4654-4660.
Li H et al., 2004, "Interspecies transmission and molecular evolution of swine influenza virus," *Chinese Journal of Veterinary Science*, 24:304-306 (with English-language summary).
Li X and Palese P, 1992, "Mutational analysis of the promoter required for influenza virus virion RNA synthesis", J Virol. Jul.;66(7):4331-8.

Li X and Palese P, 1994, "Characterization of the polyadenylation signal of influenza virus RNA", J Virol. Feb.;68(2):1245-9.
Lo, 1983, "Transformation by iontophoretic microinjection of DNA: multiple integrations without tandem insertions." Mol. Cell. Biol. 3:1803.
Loh et al., 1994, Mutant cell lines unresponsive to alpha/beta and gamma interferon are defective in tyrosine phosphorylation of ISGF-3 alpha components, Mol. Cell. Biol. 14:2170-2179.
Lu Y et al., 1994, "The influenza virus NS1 protein: a novel inhibitor of pre-mRNA splicing", Genes Dev. Aug. 1;8(15):1817-28.
Lu Y et al., 1995, "Binding of the influenza virus NS1 protein to double-stranded RNA inhibits the activation of the protein kinase that phosphoiylates the e1-2 translation initiation factor", Virology. Dec. 1;214(1):222-8.
Lucas WT, et al., 1988, "Characterization of a unique protein produced by influenza A virus recovered from a long-term persistent infection." Virology. 166(2):620-3. (Abstract only cited).
Lucas WT, et al., 1988, "Characterization of a unique protein produced by influenza A virus recovered from a long-term persistent infection." Virology. 166(2):620-3 (Abstract previously submitted as reference C117 in Information Disclosure Statement filed Aug. 22, 2008).
Lunn et al., 2001, "Safety, efficacy, and immunogenicity of a modified-live equine influenza virus vaccine in ponies after induction of exercise-induced immunosuppression." J. Am Vet. Med Assoc. 218:900-906.
Luo GX et al., 1991, "The polyadenylation signal of influenza virus RNA involves a stretch of uridines followed by the RNA duplex of the panhandle structure", J Virol. Jun.;65(6):2861-7.
Luytjes W et al., "Amplification, expression, and packaging of foreign gene by influenza virus", Cell. Dec. 22, 1989;59(6):1107-13.
Maassab and Deborde, "Characterization of an influenza A host range mutant.", Virology. Oct. 30, 1983;130(2):342-50.
Maramorosh, K and Koprowski, H. 1967. *Methods in Virology* vol. 1. Ch 6. New York: Academic Press. 178-216.
Marcus et al., 1994, Interferon induction: regulation by both virus and cell. Hokkaido Igaku Zasshi. Nov.;69(6):1320-1331.
Marión et al., 1997, "Influenza virus NS1 protein interacts with viral transcription—replication complexes in vivo," J Gen Virol, 78:2447-2451.
Marion RM et al., 1997, "The N-terminal half of influenza virus NS1 protein is fully active both in mRNA nuclear retention and enhancement of translation", in *Emergence and Re-emergence of Negative Strand Viruses, Tenth International Conference on Negative Strand Viruses*. Dublin, Ireland, Abstract No. 240, p. 170.
Marion RM et al., 1997, "The N-terminal half of the influenza virus NS1 protein is sufficient for nuclear retention of mRNA and enhancement of viral mRNA translation", Nucleic Acids Res. Nov. 1;25(21):4271-7.
Mebatsion et al, 2001, "A recombinant Newcastle disease virus with low-level V protein expression is immunogenic and lacks pathogenicity for chicken embryos." J Virol. Jan.;75(1):420-8.
Meraz MA et al., 1996, "Targeted disruption of the Stat1 gene in mice reveals unexpected physiologic specificity in the JAK-STAT signaling pathway", Cell. Feb. 9;84(3):431-42.
Mibayashi et al., 2007, "Inhibition of retinoic acid-inducible gene I-mediated induction of beta interferon by the NS1 protein of influenza A virus." J Virol. Jan.;81(2):514-24.
MMWR Weekly, Progress Toward Poliomyelitis Eradication—Nigeria, 2005-2006, Mar. 30, 2007, vol. 56(12):278-281.
Morahan et al., 1970, "Age-related cellular resistance of the chicken embryo to viral infections. I. Interferon and natural resistance to myxoviruses and vesicular stomatitis virus." J Infect Dis. Jun.;121(6):615-23.
Morley et al., 1999, "Efficacy of a commercial vaccine for preventing disease caused by influenza virus infection in horses." J. Am J. vet. Med Assoc. 215:61-66.
Mosca JD et al., 1986, "Transcriptional and posttranscriptional regulation of exogenous human beta interferon gene in simian cells defective in interferon synthesis", Mol Cell Biol. Jun.;6(6):2279-83.

(56) References Cited

OTHER PUBLICATIONS

Mumford et al., 1998, "Monitoring and detection of acute viral respiratory tract disease in horses." J. Am Vet. Med Assoc. 21:385-390.

Murphy et al., 1996, "Orthomyxoviruses" in Fields Virology, Lippincott-Raven P.A., pp. 1397-1445.

Muster T et al., 1991, "An influenza A virus containing influenza B virus 5' and 3' noncoding regions on the neuraminidase gene is attenuated in mice", Proc Natl Acad Sci U S A. Jun. 15;88(12):5177-81.

Mwau et al. 2003, A review of vaccines for HIV prevention. J. Gene. Med. 5:3-10.

Naniche et al., 2000, "Evasion of Host Defenses by Measles Virus: Wild Type Measles Virus Infection Interferes with Induction of Alpha/Beta Interferon Production", J. Virology, 74(16): 7478-7484.

Nelson et al., 1998, "Local and systemic isotype-specific antibody responses to equine influenza virus infection versus conventional vaccination." Vaccine 16:1306-1313.

Nemeroff ME et al., 1997, "Unique interactions of the influenza virus NS 1 protein with host cell nuclear functions", in *Emergence and Re-emergence of Negative Strand Viruses, Tenth International Conference on Ngative Strand Viruses.*, Dublin, Ireland. Abstract No. 229, p. 164.

Nemeroff ME et al., 1998,"Influenza virus NS1 protein interacts with the cellular 30 kDa subunit of CPSF and inhibits 3' end formation of cellular pre-mRNAs", Mol Cell. Jun.,1(7):991-1000.

Neumann et al., 1999, "Generation of influenza A viruses entirely from cloned cDNAs." Proc. Natl. Acad Sci USA 96:9345-9350.

Norton GP et al., 1987, "Infectious influenza A and B virus variants with long carboxyl terminal deletions in the NS1 polypeptides", Virology. Feb.;156(2):204-13.

Office Action dated Dec. 6, 2000 of U.S. Appl. No. 09/332,286.
Office Action dated Feb. 13, 2002 of U.S. Appl. No. 09/332,286.
Office Action dated Feb. 21, 2003 of U.S. Appl. No. 09/332,288.
Office Action dated Feb. 22, 2001 for U.S. Appl. No. 09/332,288.
Office Action dated Jun. 4, 2002 for U.S. Appl. No. 09/332,288.
Office Action dated Mar. 14, 2001 of U.S. Appl. No. 09/332,287.
Office Action dated May 23, 2000 of U.S. Appl. No. 09/332,286.
Office Action dated May 8, 2001 of U.S. Appl. No. 09/332,286.
Office Action dated Nov. 22, 2000 of U.S. Appl. No. 09/332,287.
Office Action dated Nov. 7, 2001 for U.S. Appl. No. 09/332,288.
Office Action dated Oct. 25, 2001 of U.S. Appl. No. 09/332,287.
Office Action dated Oct. 4, 1999 of U.S. Appl. No. 09/332,286.
Office Action of U.S. Appl. No. 13/250,846 dated May 9, 2013.

Olsen et al., 2000, "Virologic and serologic surveillance for human, swine and avian influenza virus infections among pigs in the north-central United States." Arch Virol 145:1399-419.

Olsen, 2002, "The emergence of novel swine influenza viruses in North America," Virus Res. 85(2):199-210.

Orkin et al. 1995, "Report and recommendations of the panel to assess the NIH investment in research on gene therapy."

Palese et al., 1999, "Learning from our foes: a novel vaccine concept for influenza virus." Arch Virol Suppl.;15:131-8.

Pansaert M et al., 1996, "Evidence of natural transmission of influenza A virus from wild ducks to swine and its potential importance for man", Bull W H O.;59:75-78.

Park et al. Newcastle disease virus (NDV)-based assay demonstrates interferon-antagonist activity for the NDV V protein and the Nipah virus V, W, and C proteins. J Virol. Jan. 2003;77(2):1501-11.

Park et al., 2003, "Newcastle disease virus V protein is a determinant of host range restriction." J Virol. 70:9522-9532.

Park YW and Katze MG, "Translational control by influenza virus. Identification of cis-acting sequences and trans-acting factors which may regulate selective viral mRNA translation", J Biol Chem Nov. 24, 1995;270(47):28433-9.

Parvin JD et al., "Nonsense mutations affecting the lengths of the NS1 nonstructural proteins of influenza A virus isolates", Virology. Jul. 30, 1983;128(2):512-7.

Patent Interference No. 105,952—*Baxter Healthcare SA* and *Mount Sinai School of Medicine* (U.S. Appl. No. 12/480,410), *Junior Party*, v. *Mount Sinai School of Medicine* (U.S. Pat. No. 7,588,768), *Senior Party*. Declaration of Interference, Jul. 9, 2013.

Patent Interference No. 105,952—*Vivaldi Biosciences Inc.* and *Icahn School of Medicine at Mount Sinai* (U.S. Appl. No. 12/480,410), *Junior Party*, v. *Icahn School of Medicine at Mount Sinai* (U.S. Pat. No. 7,588,768), *Senior Party*, Judgment, Oct. 29, 2013.

Perez et al., 2003, "Land-based birds as potential disseminators of avian/mammalian reassortant influenza A viruses," *Avian Diseases* 47:1114-1117.

Perry et al., 1993, "Transgenesis in chickens" Transgenic Res. 2(3):125-33.

Piccone ME et al., "Mutational analysis of the influenza virus vRNA promoter", Virus Res. May 1993;28(2):99-112.

Pleschka S et al., "A plasmid-based reverse genetics system for influenza A virus", J Virol. Jun. 1996;70(6):4188-92.

Qian et al., 1995, "An amino-terminal polypeptide fragment of the influenza virus NS1 protein possesses specific RNA-binding activity and largely helical backbone structure." RNA 1:948-956.

Qin XQ et al., "Interferon-beta gene therapy inhibits tumor formation and causes regression of established tumors in immune-deficient mice", Proc Natl Acad Sci U S A. Nov. 24, 1998;95(24):14411-6.

Qiu Y and Krug RM, "The influenza virus NS1 protein is a poly(A)-binding protein that inhibits nuclear export of mRNAs containing poly(A)", J Virol. Apr. 1994;68(4):2425-32.

Qiu Y et al., "The influenza virus NS1 protein binds to a specific region in human U6 snRNA and inhibits U6-U2 and U6-U4 snRNA interactions during splicing", RNA. May 1995;1(3):304-16.

Quinlivan et al., Attenuation of equine influenza viruses through truncations of the NS1 protein. J Virol. Jul. 2005;79(13):8431-9.

Qureshi et al., 1996, Function of Stat2 protein in transcriptional activation by alpha interferon, Mol. Cell. Biol. 16:288-293.

Reed et al., 1938, "A simple Method of estimating fifty percent endpoints." Am J. Hyg 27(3):493-497.

Restifo et al., 1998, "The promise of nucleic acid vaccines." Virology 249:89-97.

Restifo et al., 1998, "Transfectant influenza A viruses are effective recombinant immunogens in the treatment of experimental cancer.", Virology 249:89-97.

Richt & Garcia-Sastre, 2009, "Attenuated influenza virus vaccines with modified NS1 proteins," Current Topics in Microbiology and Immunology 333:177-195.

Richt et al., 2003, "Attenuation of an H3N2 swine Influenza virus utilizing a reverse genetics approach," 4th Intl. Symposium on Emerging and Re-emerging Pig Diseases—Rome, Jun. 29-Jul. 2, 2003, pp. 264-265.

Richt et al., Vaccination of pigs against swine influenza viruses by using an NS1-truncated modified live-virus vaccine. J Virol. Nov. 2006;80(22):11009-18.

Robert-Guroff et al. 1998, Vaccine protection against a heterologous, non-syncytium-inducing, primary human immunodeficiency virus. J. Virol. 72:10275-10280.

Rogers G N, Paulson J C. Receptor determinants of human and animal influenza virus isolates: differences in receptor specificity of the H3 henaagglutinin based on species of origin. Virology. 1983;127:361-373.

Rui et al., 2004, "Progress of swine influenza virus," Progress in Veterinary Medicine 25:25-28 (In Chinese with English Abstract).

Sang, 1994, "Transgenic chickens—methods and potential applications", Trends Biotechnol. 12(10):415-20.

Schlender et al., 2000, "Bovine Respiratory Syncytial Virus Nonstructural Proteins NS1 and NS2 Cooperatively Antagonize Alpha/Beta Interferon-Induced Antiviral Response", J. of Virology 74(18):8234-8242.

Scholtissek et al., 1998, "Influenza in pigs and their role as the intermediate host," Ch. 13 In K. G. Nicholson, R. G. Webster, A. J. Hay (ed.), *Textbook of influenza*, Blackwell Science, Oxford, United Kingdom, pp. 137-145.

Scholtissek, 1990, "Pigs as 'mixing vessels' for the creation of new pandemic influenza A viruses." Med Principles Pract 2:65-71.

Scholtissek, 1994, "Source for influenza pandemics." Eur J. Epidemiol 10:455-8.

(56) References Cited

OTHER PUBLICATIONS

Schuepbach et al., Early antiviral antibody response after immunization with viral oncolysate: a powerful prognostic marker for acute myelogenous leukemia remission patients. Blood. Sep. 1983;62(3):616-21.
Schultz et al., 1991, "Evolution of pig influenza viruses", Virology;183:61-73.
Sekellick MJ et al., "Development of the interferon system. I. In chicken cells development in ovo continues on time in vitro", In Vitro Cell Dev Biol. Oct. 1990;26(10):997-1003.
Sekellick MJ et al., "Interferon induction by viruses. XIV. Development of interferon inducibility and its inhibitionin chick embryo cells "aged" in vitro", J Interferon Res. 1985 Fall;5(4):651-67.
Seno et al., 1990, "Enhancing Effect of Centrifugation on Isolation of Influenza Virus from Clinical Specimens." J Clin. Microb. 28(7):1669-1670.
Shaw et al., "Immunologic studies on the influenza A virus nonstructural protein NS1.", J Exp Med. Jul. 1, 1982;156(1):243-54.
Shaw et al., 1996, "Nucleocapsid protein alone is sufficient for the generation of influenza transfectants" in *Options for the Control of Influenza III*, Brown (eds.), Hampson Webster (Elsevier Science) pp. 433-436.
Shope RE, 1951, "The provocation of masked swine influenza virus by infection with human influenza virus," Tijdschrift Voor Diergeneeskunde 76:414-420.
Shope, 1931, "Swine Influenza: III. Filtration Experiments and Etiology." J. Exp. Med. 54:373-385.
Shu et al., 1994, "Evidence for interspecies transmission and reassortment of influenza A viruses in pigs in southern China." Virol. 202:825-33.
Shuman, 1991, "Production of transgenic birds", Experientia. 47(9):897-905.
Snyder et al., "A 36 nucleotide deletion mutation in the coding region of the NS1 gene of an influenza A virus RNA segment 8 specifies a temperature-dependent host range phenotype.", Virus Res. Jan. 1990;15(1):69-83.
Soboll et al., 2003, "Mucosal co-administration of cholera toxin and influenza virus hemagglutinin-DNA in ponies generates a local IgA response." Vaccine 21:3081-3092.
Solorzano et al., 2005, "Mutations in the NS1 protein of swine influenza virus impair anti-interferon activity and confer attenuation in pigs." J Virol. 79(12):7535-43.
Sovinova et al., 1958, "Isolation of a virus causing respiratory disease in horses." Acta Virol 2:52-61.
Stark et al., 1998, "How Cells Respond to interferons", Annu.Rev. Biochem. 67:227-264.
Stern, 1996, "Chick stem cells", Curr Top Microbiol Immunol. 212:195-206.
Stojdl et al., 2003, "VSV strains with defects in their ability to shutdown innate immunity are potent systemic anti-cancer agents" Cancer Cell 4:263-275.
Supplementary European Search Report EP 05 85 6778, dated Dec. 9, 2009.
Supplementary European Search Report EP 05 85 6779, dated Feb. 16, 2009.
Supplementary European Search Report EP 99 92 7443, dated Oct. 30, 2002.
Supplementary Partial European Search Report EP 99 92 7440, dated Jul. 17, 2001.
Supplementary Partial European Search Report EP 99 92 7445, dated Nov. 3, 2004.
Talon et al. 2000, Influenza A and B viruses expressing altered NS1 proteins: A vaccine Approach. PNAS, 96(8):4309-4314.
Talon et al., 2000, "Activation of Interferon Regulatory Factor 3 Is Inhibited by the Influenza A Virus NS1 Protein", J. of Virology, 74(17): 7989-7996.
Taniguchi et al., 1996, "Nondefective rotavirus mutants with an NSP1 gene which has a deletion of 500 nucleotides, including a cysteine-rich zinc finger motif-encoding region (nucleotides 156 to 248), or which has a nonsense codon at nucleotides 153 to 155," Journal of Virology 70:4125-4130.
Tobita K et al., "Nucleotide sequence and some biological properties of the NS gene of a newly isolated influenza B virus mutant which has a long carboxyl terminal deletion in the NS1 protein", Virology. Jan. 1990;174(1):314-9.
Townsend, 2001, "Efficacy of a cold-adapted, intranasal, equine influenza vaccine: challenge trials." Equine Vet J. 33:637-643.
U.S. Appl. No. 12/148,798, Amendment dated May 27, 2011.
U.S. Appl. No. 12/148,798, Amendment dated Sep. 2, 2011.
U.S. Appl. No. 12/148,798, Issue Fee Transmittal dated Sep. 28, 2011.
U.S. Appl. No. 12/148,798, Notice of Allowance and Fees due dated Sep. 21, 2011.
U.S. Appl. No. 12/148,798, Office Action dated Aug. 17, 2011.
U.S. Appl. No. 12/148,798, Terminal Disclaimer dated May 26, 2011.
U.S. Appl. No. 09/332,286: Amendment Under 37 C.F.R. § 1.111, dated Nov. 8, 2001.
U.S. Appl. No. 09/332,286: Amendment Under 37 C.F.R. § 1.111, dated Mar. 6, 2000.
U.S. Appl. No. 09/332,286: Amendment Under 37 C.F.R. § 1.116, dated Aug. 12, 2002.
U.S. Appl. No. 09/332,286: Amendment Under 37 C.F.R. § 1.116, dated Nov. 24, 2000.
U.S. Appl. No. 09/332,286: Notice of Allowance dated Jan. 17, 2003.
U.S. Appl. No. 09/332,287: Amendment Under 37 C.F.R. § 1.111, dated Sep. 14, 2001.
U.S. Appl. No. 09/332,287: Amendment Under 37 C.F.R. § 1.116, dated Mar. 25, 2002.
U.S. Appl. No. 09/332,287: Notice of Allowance, dated May 28, 2002.
U.S. Appl. No. 09/332,287: Office Action, dated Apr. 15, 2002.
U.S. Appl. No. 09/332,287: Supplemental Amendment Under 37 C.F.R. § 1.116, dated Apr. 12, 2002.
U.S. Appl. No. 09/332,287: Supplemental Amendment Under 37 C.F.R. § 1.116, dated Apr. 10, 2002.
U.S. Appl. No. 09/332,288: Amendment Under 37 C.F.R. § 1.111, dated Dec. 4, 2002.
U.S. Appl. No. 09/332,288: Amendment Under 37 C.F.R. § 1.111, dated Mar. 7, 2002.
U.S. Appl. No. 09/332,288: Amendment Under 37 C.F.R. § 1.111, dated Aug. 22, 2001.
U.S. Appl. No. 09/332,288: Amendment Under 37 C.F.R. § 1.116, dated Jul. 21, 2003.
U.S. Appl. No. 09/332,288: Examiner's Amendment, dated May 31, 2002.
U.S. Appl. No. 09/332,288: Notice of Allowance, dated Aug. 6, 2003.
U.S. Appl. No. 09/724,419: Amendment Under 37 C.F.R. § 1.111, dated Jun. 11, 2003.
U.S. Appl. No. 09/724,419: Amendment Under 37 C.F.R. § 1.111, dated Dec. 31, 2002.
U.S. Appl. No. 09/724,419: Amendment Under 37 C.F.R. § 1.111, dated Apr. 19, 2002.
U.S. Appl. No. 09/724,419: Amendment Under 37 C.F.R. § 1.116, dated Feb. 26, 2004.
U.S. Appl. No. 09/724,419: Notice of Allowance, dated May 27, 2004.
U.S. Appl. No. 09/724,419: Office Action, dated Aug. 26, 2003.
U.S. Appl. No. 09/724,419: Office Action, dated Dec. 19, 2001.
U.S. Appl. No. 09/724,419: Office Action, dated Feb. 11, 2003.
U.S. Appl. No. 09/724,419: Office Action, dated Jul. 2, 2002.
U.S. Appl. No. 10/314,569: Amendment Under 37 C.F.R. § 1.111, dated Jan. 26, 2004.
U.S. Appl. No. 10/314,569: Amendment Under 37 C.F.R. § 1.116, dated Sep. 17, 2004.
U.S. Appl. No. 10/314,569: Notice of Allowance, dated Oct. 20, 2004.
U.S. Appl. No. 10/314,569: Office Action dated Apr. 20, 2004.
U.S. Appl. No. 10/314,569: Office Action dated Aug. 26, 2003.

(56) References Cited

OTHER PUBLICATIONS

U.S. Appl. No. 10/945,718: Amendment Under 37 C.F.R. § 1.111, dated Apr. 7, 2008.
U.S. Appl. No. 10/945,718: Amendment Under 37 C.F.R. § 1.111, dated Nov. 28, 2006.
U.S. Appl. No. 10/945,718: Notice of Allowance, dated Oct. 16, 2008.
U.S. Appl. No. 10/945,718: Office Action, dated Aug. 29, 2006.
U.S. Appl. No. 10/945,718: Office Action, dated Jan. 10, 2006.
U.S. Appl. No. 10/945,718: Office Action, dated Jun. 22, 2005.
U.S. Appl. No. 10/945,718: Office Action, dated Oct. 5, 2007.
U.S. Appl. No. 10/945,718: Reply Under 37 C.F.R. § 1.111, dated May 10, 2006.
U.S. Appl. No. 10/945,718: Reply Under 37 C.F.R. § 1.111, dated Oct. 24, 2005.
U.S. Appl. No. 10/713,732, Amendment Under 37 C.F.R. § 1.111, dated Dec. 2, 2008.
U.S. Appl. No. 10/713,732, Amendment Under 37 C.F.R. § 1.111, dated Apr. 11, 2008.
U.S. Appl. No. 10/713,732, Amendment Under 37 C.F.R. § 1.111, dated Mar. 23, 2007.
U.S. Appl. No. 10/713,732, Notice of Allowance, dated Mar. 13, 2009.
U.S. Appl. No. 10/713,732, Office Action dated May 15, 2007.
U.S. Appl. No. 10/713,732, Office Action dated Jul. 2, 2008.
U.S. Appl. No. 10/713,732, Office Action dated Oct. 19, 2007.
U.S. Appl. No. 10/713,732, Office Action dated Oct. 24, 2006.
U.S. Appl. No. 11/884,401, Office Action dated Mar. 3, 2010.
U.S. Appl. No. 11/884,401, Office Action dated Jun. 10, 2009.
U.S. Appl. No. 11/884,401; Amendment Under 37 C.F.R. § 1.111, dated Sep. 2, 2010.
U.S. Appl. No. 11/884,401; Office Action, dated Mar. 31, 2011.
U.S. Appl. No. 11/884,401; Response to Notice of Non-Compliant Amendment (37 C.F.R. § 1.121), dated Jan. 24, 2011.
U.S. Appl. No. 12/148,798; Office Action dated Nov. 29, 2010.
U.S. Appl. No. 12/364,243, Office Action dated Mar. 17, 2010.
U.S. Appl. No. 12/364,243; Amendment Under 37 C.F.R. § 1.111, dated Aug. 17, 2010.
U.S. Appl. No. 12/364,243; Correction of Amendment Under 37 C.F.R. § 1.111 filed on Aug. 17, 2010, dated Nov. 29, 2010.
U.S. Appl. No. 12/364,243; Office Action dated Feb. 16, 2011.
U.S. Appl. No. 11/884,401, Notice of Allowance, dated Aug. 18, 2011.
U.S. Appl. No. 11/884,401, Office communication with Notice of Allowability, dated Aug. 25, 2011.
U.S. Appl. No. 12/364,243, Reply Under 37 C.F.R. § 1.114, dated Jul. 18, 2011.
Van Der Putten et al., 1985, "Efficient insertion of genes into the mouse germ line via retroviral vectors." Proc. Natl Acad Sci 82:6148-6152.
Vandemark and Batzing, 1986, "The microbes: an introduction to their nature and importance", The Microbes. pp. 670-680.
Verma et al., 1997, "Gene therapy—promises, problems and prospects." Nature. Sep. 18;389(6648): 239-42.
Veselov et al., 1984, "Isolation of preparative amounts of influenza virus hemagglutinin by an affinity chromatographic method." Vopr Virusol 29(1):93-7 Abstract in English.
Vincent et al., 2007, "Efficacy of intranasal administration of a truncated NS1 modified live influenza virus vaccine in swine," Vaccine 25:7999-8009.
Waddell et al., "A new influenza virus associated with Equine Respiratory Disease." 1963, J Am Vet Med. Assoc. 143:587-590.
Wang et al., 2002, "Functional replacement of the carboxy-terminal two-thirds of the influenza A virus NS1 protein with short heterologous dimerization domains." J Virol. Dec.;76(24):12951-62.

Wang et al., 2000, "Influenza A Virus NS1 Protein Prevents Activation of NF-KB and Induction of Alpha/Beta Interferon", J. of Virology 74(24): 11566-11573.
Weaver BK et al., 1998, "Interferon regulatory factor 3 and CREB-binding protein/p300 are subunits of double-stranded RNA-activated transcription factor DRAF1", Mol Cell Biol. Mar.;18(3):1359-68.
Webby et al., 2000, "Evolution of swine H3N2 influenza viruses in the United States." J. Virol 74:8243-51.
Webby et al., 2001, "Emergence of Influenza A Viruses," Philos Trans R Soc Lond B Biol Sci 356:1817-28.
Weber et al., 2004, "Inverse interference: How viruses fight the interferon system," Viral Immunology 17:498-525.
Webster & Thomas, 1993, "Efficacy of equine influenza vaccines for protection against A/Equine/Jilin/89 (H3N8)—a new equine influenza virus," Vaccine 11:987-993.
Webster, 1993, "Are equine 1 influenza viruses still present in horses?" Equine vet. 25:537-538.
Wong et al., 1997, Interferon-resistant human melanoma cells are deficient in ISGF3 components, STAT1, STAT2, and p48-ISGF3gamma, J.Biol. Chem. 272:28779-28785.
Wressnigg et al., 2009, "Influenza B mutant viruses with truncated NS1 proteins grow efficiently in Vero cells and are immunogenic in mice," Journal of General Virology 90:366-374.
Written Opinion PCT/US05/19382, dated Sep. 28, 2006.
Written Opinion PCT/US05/19383, dated Oct. 11, 2006.
Written Opinion PCT/US99/13139, dated Jun. 14, 2000.
Written Opinion PCT/US99/13142, dated May 3, 2000.
Written Opinion of International application No. PCT/US99/13144, dated Jul. 25, 2000.
Wuethrich, 2003, "Chasing the fickle swine flu," Science 299(5612):1502-5.
Yang et al., 1998, STAT3 complements defects in an interferon-resistant cell line : Evidence for an essential role for STAT3 in interferon signaling and biological activities, Proc. Natl. Acad. Sci. USA 95:5568-5572.
Yannarell DA, Hjorth RN. , 1997, Factors affecting the yield of cold-adapted influenza virus vaccine. J Virol Methods. 64(2):161-9.
Yoshida T et al., "Characterization of the RNA associated with influenza A cytoplasmic inclusions and the interaction of NS1 protein with RNA.", Virology. Apr. 15, 1981;110(1):87-97.
Young et al., 2000, "Paramyxoviridae Use Distinct Virus Specific Mechanisms to Circumvent the Interferon Response", Virology, 269:383-390.
Young JF et al., "Efficient expression of influenza virus NS1 nonstructural proteins in *Escherichia coli*.", Proc Natl Acad Sci U S A. Oct. 1983;80(19):6105-9.
Zhou, 1999, "Genetic reassortment of avian, swine, and human influenza A viruses in American pigs", J. Virol 73:8851-6.
Zhou, 2000, "Emergence of H3N2 reassortant influenza A viruses in North American pigs." Vet Microbiol 74:47-58.
Zhu et al., 2008, "A naturally occurring deletion in its NS1 gene contributes to the attenuation of an H5N1 influenza swine virus in chickens," Journal of Virology 82:220-228.
Marozin et al., 2002, "Antigenic and genetic diversity among swine influenza A H1N1 and H1N2 viruses in Europe", J Gen Virol; 83:735-745.
GenBank Accession No. AAD51273, 1999, "NS1 [Influenza A virus (A/Swine/Texas/4199-2/98 (113N2))]".
GenBank Accession No. AF153261, 1999, "Influenza A virus (A/Swine/Texas/4199-2/98 (H3N2)) segment 8 NS1 and NS2 genes".
U.S. Appl. No. 11/884,401, Amendment dated Dec. 10, 2009.
Vincent et al., 2012, "Live Attenuated Influenza Vaccine Provides Superior Protection from Heterologous Infection in Pigs with Maternal Antibodies without Inducing Vaccine-Associated Enhanced Respiratory Disease," Journal of Virology, 86(19):10597-10605.
Kappes et al., 2012, "Vaccination with NS1-truncated H3N2 swine influenza virus primes T cells and confers cross-protection against an H1N1 heterosubtypic challenge in pigs," Vaccine, 30:280-288.

FIG.5A
FIG.5B
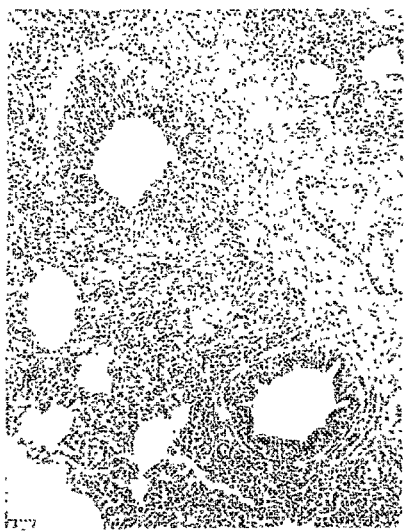
FIG.5C
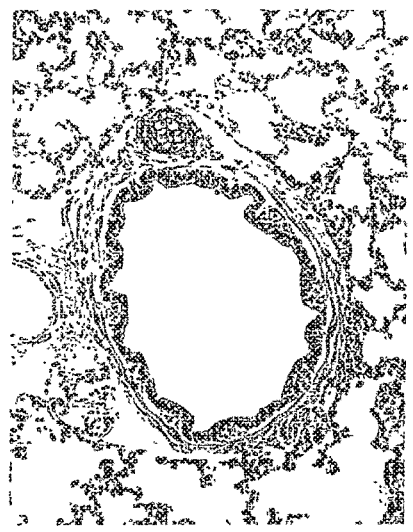
FIG.5D

SEQUENCE LISTING

<160> NUMBER OF SEQ ID NOS: 21

<210> SEQ ID NO 1
<211> LENGTH: 2318
<212> TYPE: DNA
<213> ORGANISM: Artificial Sequence
<220> FEATURE:
<223> OTHER INFORMATION: plasmid insert PB2

<400> SEQUENCE: 1

```
gggagcgaaa gcaggtcaaa tatattcaat atggagagaa taaaagaact aagagatcta      60
atgtcgcagt cccgcactcg cgagatactc actaagacca ctgtggacca tatggccata     120
```

```
atcaaaaagt acacatcagg aaggcaagag aagaaccccg cactcagaat gaagtggatg      180
atggcaatga aatacccaat tacagcagac aagagaataa tggacatgat tccagagagg      240
aatgaacaag gacaaaccct ctggagcaaa acaaacgatg ctggatcaga ccgcgtgatg      300
gtatcacctc tggccgtaac atggtggaat aggaatggcc caacaacaag tacagttcac      360
taccctaagg tatataaaac ttatttcgaa aaagtcgaaa ggttaaaaca tggtacctttt     420 ggccctgtcc acttcagaaa tcaagttaaa ataagaagga gagttgacac aaaccctggt      480
cacgcagatc tcagtgccaa ggaggcacag gatgtgatca tggaagttgt tttcccaaat     540
gaagtggggg caagaatact gacatcagag tcacagctga caataacaaa agagaagaaa      600
gaagagctcc aggattgtaa aattgctccc ttgatggtgg catacatgct agaaagagag      660
ttggtccgta aaacgaggtt tctcccggtg gctggtggaa caggcagtgt ttatattgag      720
gtgctgcact taacccaggg gacatgctgg gagcagatgt acactccagg aggagaagtg      780
agaaatgatg atgttgacca aagtttgatt atcgctgcta gaaacatagt aagaagagca      840
gcagtgtcag cagacccatt agcatctctc ttggaaatgt gccacagcac acagattgga      900
ggaataagga tggtggacat ccttagacag aatccaacgg aggaacaagc cgtagacata      960
tgcaaggcag caatggggtt gaggattagc tcatctttca gctttggtgg gttcactttc     1020
aaaagaacaa gcggatcatc agtcaagaaa gaagaagaag tgctcacggg caacctccaa     1080
acactgaaaa taagagtaca tgaaggatat gaagaattca caatggtcgg gagaagagca     1140
acagctattc tcagaaaggc aaccaggaga ttgatccagt taatagtaag tgggagagac     1200
gagcagtcaa ttgctgaggc aataattgtg gccatggtat tttcacaaga ggattgcatg     1260
atcaaggcag ttaggggcga tctgaacttt gtcaataggg caaaccagcg actgaatccc     1320
atgcaccaac tcttgaggca tttccaaaaa gatgcaaaag tgcttttcca gaactgggga     1380
attgaaccca tcgacaatgt gatgggaatg atcggaatat gcccgatat gatcccaagc     1440 acggagatgt cgctgagagg gataagagtc agcaaaatgg gagtagatga atactccagc     1500
acggagagag tggtagtgag cattgaccga tttttgaggg ttcgggatca acgagggaac     1560
gtactattgt ctcccgaaga ggtcagcgag acacaaggga cggagaagtt gacaataact     1620
tattcgtcat caatgatgtg ggagatcaat ggtcctgagt cagtgctggt caacactat      1680 caatggatca tcaggaactg ggaaactgtg aaaattcaat ggtcgcaaga tcccacgatg     1740
ttatacaaca aaatggaatt tgaaccattt cagtctcttg tccctaaggc aaccagaagc     1800
cgatacagtg gattcgtaag gacactgttc cagcaaatgc gggatgtgct tggaacattt     1860
gacactgtcc aaataataaa acttctcccc tttgctgctg ctccaccaga acagagtagg     1920
atgcagtttt cctcattgac tgtgaatgtg agaggatcag ggttgaggat actggtaaga     1980
ggcaattctc cagtattcaa ttacaacaaa gcaaccaaaa ggcttacagt tcttggaaag     2040
gatgcaggtg cattgactga agatccagat gaaggcacag ctggagtgga gtctgctgtc     2100
ctgagaggat ttctcatttt gggcaaagaa gacaagagat atggcccagc attaagcatc     2160
aatgaactga gcaatcttgc aaaaggagag aaggctaatg tgctaattgg gcaaggagac     2220
gtagtgttgg taatgaaacg gaaacgggac tctagcacc ttactgacag ccagacagcg     2280
accaaaagaa ttcggatggc catcaattag tgtcgaat                             2318
```

<210> SEQ ID NO 2
<211> LENGTH: 2348
<212> TYPE: DNA

<213> ORGANISM: Artificial Sequence
<220> FEATURE:
<223> OTHER INFORMATION: plasmid insert PB1

<400> SEQUENCE: 2

```
gggagcgaaa gcaggcaaac catttgaatg gatgtcaatc cgactctact ttttctaaag      60
gttccagcgc aaaatgccat aagcaccaca ttcccttata ctggagatcc tccatacagc     120
catggaacag gaacaggata caccatggac acagtcaaca gaacacacca atattcagaa     180
aaagggaagt ggacgacaaa cacagagact ggggcacccc agctcaaccc gattgatgga     240
ccactacctg aggataatga accaagtgga tatgcacaaa cagactgtgt tctggaggcc     300
atggctttcc ttgaagaatc ccacccaggg atatttgaga attcatgcct tgaaacaatg     360
gaagttgttc aacaaacaag ggtgataaaa ctaactcaag gtcgccagac ttatgattgg     420
acattaaaca gaaatcaacc ggcagcaact gcattggcca acaccataga agttttaga      480
tcgaatggtc taacagctaa tgagtcagga aggctaatag atttcctaaa ggatgtgatg     540
gaatcaatgg ataagagga aatagagata acaacacact tcaaagaaa aaggagagta      600
agagacaaca tgaccaagaa gatggtcaca caaagaacaa taggaaagaa aaaacaaaga     660
gtgaataaga gaggttatct aataagagca ctgacattga atacgatgac caaagatgca     720
gagagaggca aattaaaaag aagggctatc gcaacacctg ggatgcaaat tagagggttc     780
gtgtactttg ttgaaacttt agctaggagc atttgcgaaa agcttgaaca gtctggactc     840
ccagtagggg gcaatgaaaa gaaagccaaa ttggcaaatg ttgtgagaaa gatgatgact     900
aattcacaag acacagagct ttctttcaca atcactgggg acaacactaa gtggaatgaa     960
aatcaaaatc ctcgaatgtt cctggcgatg attacatata tcaccagaaa tcaacccgag    1020
tggttcagaa acatcctgag catggcaccc ataatgttct caaacaaaat ggcaagacta    1080
ggaaaagggt acatgttcga gagtaaaaga atgaagctcc gaacacaaat accagcagaa    1140
atgctagcaa gcattgacct gaagtatttc aatgaatcaa caggaagaa aattgagaaa    1200
ataaggcctc ttctaataga tggcacagca tcattgagcc ctggaatgat gatgggcatg    1260
ttcaacatgc taagtacggt tttgggagtc tcgatactga atcttggaca aaagaaatac    1320
accaggacaa catactggtg gatggactc caatcctccg acgattttgc cctcatagtg    1380
aatgcaccaa atcatgaggg aatacaagca ggagtggata gattctacag gacctgcaag    1440
ttagtgggaa tcaacatgag caaaaagaag tcctatataa ataagacagg acatttgaa    1500
ttcacaagct ttttttatcg ctatggattt gtggctaatt ttagcatgga gctgcccagt    1560
tttggagtgt ctggaataaa tgaatcagct gatatgagta ttggagtaac agtgataaag    1620
aacaacatga taaacaatga ccttggacct gcaacagccc agatggccct tcaattgttc    1680
atcaaagact acagatacac atataggtgc catagaggag acacacaaat tcagacgaga    1740
agatcattcg agctaaagaa gctgtgggat caaacccaat caaaggcagg actattagta    1800
tctgatggag gaccaaactt atacaatatc cggaatcttc acattcctga agtctgctta    1860
aaatgggagc taatggatga ggattatcgg ggaagacttt gtaatcccct gaaccccttt    1920
gtcagccata aagagattga ttctgtaaac aatgctgtgg tgatgccagc ccatggtcca    1980
gccaagagca tggaatatga tgccgttgca actacacact cctggattcc caagaggaac    2040
cgctctattc tcaacacaag ccaaggggga attcttgagg atgaacagat gtaccagaag    2100
tgctgcaacc tgttcgagaa atttttccct agtagttcat acaggagacc ggttggaatt    2160
tctagcatgg tggaggccat ggtgtctagg gcccggattg atgccaggat tgacttcgag    2220
```

```
tctggacgga ttaagaaaga agagttctct gagatcatga agatctgttc caccattgaa    2280
gaactcagac ggcaaaaata atgaatttag cttgtccttc atgaaaaaat gccttgtttc    2340
tactaata                                                             2348

<210> SEQ ID NO 3
<211> LENGTH: 2240
<212> TYPE: DNA
<213> ORGANISM: Artificial Sequence
<220> FEATURE:
<223> OTHER INFORMATION: plasmid insert PA

<400> SEQUENCE: 3
gggagcgaaa gcaggtactg atccaaaatg aagactttg tgcgacaatg cttcaatcca      60
atgatcgtcg agcttgcgga aaaggcaatg aaagaatatg gagaagatcc gaaaatcgaa    120
actaacaaat tcgctgcaat atgcacacac ttggaagtct gtttcatgta ttcggatttc    180
catttcatcg acgaacgggg tgaatcaata attgtagaat ctggtgatcc aaatgcatta    240
ctgaagcacc gatttgagat aattgaagga agagacagga ccatggcctg gacagtggtg    300
aacagtatct gcaacaccac aggggtagag aagcctaaat tcttccggat tttgtatgat    360
tacaaagaga accgattcat tgaaattgga gtgacacgga gggaggtcca catatactac    420
ctagagaaag ccaacaaaat aaaatccgag aagacacaca ttcacatttt ttcattcact    480
ggagaggaga tggccaccaa agcggactac acccttgatg aagagagcag ggcaagaatc    540
aaaaccaggc ttttcaccat aagacaagaa atggccagta ggggtctatg ggattccttt    600
cgtcagtccg agagaggcga agagacaatt gaagaaagat ttgaaattac aggaaccatg    660
cgcaggcttg ccgaccaaag tctcccaccg aacttctcca gccttgaaaa ctttagagcc    720
tatgtagatg gattcgaacc gaacggctgc attgagggca gctttctca aatgtcaaaa    780 gaagtgagcg ccaaaattga accattcttg aagacaacac cacgccccct cagattgcct    840
gatgggcctc cttgctctca gcggtcaaag ttcttgctga tggatgctct gaaactaagt    900
attgaagacc cgagtcatga ggggaagggg ataccactat atgatgcaat caatgcatg    960 aagacatttt ttggctggaa agagcctaac ataatcaaac acatgagaa aggcataaac   1020 cccaattacc tcctggcttg aagcaggtg ctagcagagc tccaggacat gaaaatgaa    1080 gagaagatcc aaagacaaa gaacatgaag agaacaagcc aattgaagtg gcactcggt    1140 gagaatatgg caccagagaa agtagacttt gatgactgca agatgttgg tgatcttaaa    1200 cagtatgaca gcgatgagcc agagcccaga tctctagcaa gctgggtcca aaatgaattc    1260
aataaggcat gtgaattgac cgattcaagc tggatagaac ttgatgagat aggagaagat    1320
gttgccccga ttgaacacat cgcaagcatg aggaggaact attttacagc agaagtgtcc    1380
cattgcaggg ccactgaata cataatgaag ggagtgtaca taaatacggc tttgctcaat    1440
gcatcttgtg cagccatgga tgacttccag ctgatcccaa tgataagcaa atgtaggacc    1500
aaagaaggaa gacggaaaac aaatctgtat ggggttcatta taaaggaag gtctcatttg    1560 agaaatgata ctgacgtggt gaactttgta agtatggagt ctcccctcac tgacccgaga    1620
ctggagccac acaaatggga aaagtactgt gttcttgaaa taggagacat gctcctgagg    1680
actgcgatag gccaagtgtc gaggcccatg ttcctatatg tgagaaccaa tggaacctcc    1740
aagatcaaga tgaaatgggg catggaaatg aggcgctgcc ttcttcagtc tcttcagcag    1800
attgagagca tgattgaggc cgagtcttct gtcaaagaga aagacatgac caaggaattc    1860
```

| | |
|---|---|
| tttgaaaaca aatcggagac atggccaatc ggagaatcac ccaaaggagt ggaggaaggc | 1920 |
| tctattggga aagtgtgcag gaccttactg gcaaaatctg tattcaacag tctatacgcg | 1980 |
| tctccacaac ttgaggggtt ttcggctgaa tcgagaaaat tgcttctcat tgttcaggca | 2040 |
| cttagggaca acctggaacc tggaaccttc gatcttgggg ggctatatga agcaatcgag | 2100 |
| gagtgcctga ttaatgatcc ctgggttttg cttaatgcat cttggttcaa ctccttcctc | 2160 |
| acacatgcac tgaaatagtt gtggcaatgc tactatttgc tatccatact gtccaaaaaa | 2220 |
| gtaccttgtt tctactaata | 2240 |

<210> SEQ ID NO 4
<211> LENGTH: 1769
<212> TYPE: DNA
<213> ORGANISM: Artificial Sequence
<220> FEATURE:
<223> OTHER INFORMATION: plasmid insert HA

<400> SEQUENCE: 4

| | |
|---|---|
| gggagcaaaa gcaggggata attctattaa ccatgaagac tatcattgct ttgagctaca | 60 |
| ttttatgtct ggttttcgct caaaaacttc ccggaaatga caacagcaca gcaacgctgt | 120 |
| gcctgggaca ccatgcagtg ccaaacggaa ccctagtgaa acaatcacg aatgatcaaa | 180 |
| ttgaagtgac taatgctact gagctggttc agagttcctc aacaggtaga atatgcgaca | 240 |
| gtcctcaccg aatccttgat ggaaaaaact gcacattgat agatgctcta ctgggagacc | 300 |
| ctcattgcga tggctttcaa aataaggaat gggaccttt tattgaacgc agcaaagctt | 360 |
| acagcaactg ttacccttat gatgtgccgg attattcctc ccttaggtca ctagttgcct | 420 |
| catcaggcac cctggagttt accaatgaag acttcaattg gactggggtc gctcaggatg | 480 |
| ggggaagcta ttcttgcaaa aggggatctg ttaaaagttt ctttagtaga ttgaattggt | 540 |
| tacacaaatt agaatacaaa tatccagcac tgaacgtgac tatgccaaac aatgacaaat | 600 |
| ttgacaaatt gtacatttgg ggggttcacc acccgagcac ggacagtgaa caaaccagcc | 660 |
| tgtatgttca agcaataggg agagtcacag tctctaccaa aagtagccaa caaactgtaa | 720 |
| tcccgaacat cgggtccaga ccctgggtga gggcatctc cagtagaata agcatctatt | 780 |
| ggacaatagt aaaaccggga gacatacttt tgattagcag cacagggaat ctaattgctc | 840 |
| ctcgggggtta cttcaaaata cgaaatggga aaagctcaat aatgaggtca gatgcaccca | 900 |
| ttgacaactg ctattctgaa tgcatcactc caaatggaag cattcccaat gacaaacctt | 960 |
| ttcaaaatgt aaataggatc acatatgggg cctgtcccaa atatgttaag caaaaaccc | 1020 |
| tgaaattggc aacagggatg cggaatgtac cagagaaaca aactagaggc atattcggcg | 1080 |
| caatcgcagg tttcatagaa aatggttggg agggaatggt agacggttgg tacggtttca | 1140 |
| ggcatcaaaa ttctgagggc acaggacaag cagcagatct taaaagcacc caagcagcaa | 1200 |
| tcgatcaagt caacgggaaa ttgaataggt taatcgagaa aacgaacgag aaattccatc | 1260 |
| aaatcgaaaa agaattttca gaagtagaag ggagaattca ggacctcgag aaatatgttg | 1320 |
| aagacactaa aatagatctc tggtcttaca acgcggagct ccttgttgcc ctggagaatc | 1380 |
| aacatacaat tgatctaact gactcagaaa tgaacaaact gtttgaaaaa acaaggaagc | 1440 |
| aactgaggga aaatgctgag gacatgggca atggttgctt caaatatac cacaaatgtg | 1500 |
| acaatgcctg catagggtca atcagaaatg gaacttatga ccatgatgta tacagagacg | 1560 |
| aagcattaaa caaccggttc cagatcaaag gtgttgagct gaaatcagga tacaaagatt | 1620 |
| ggatcctatg gatttccttt gccatatcat gcttttgct ttgtgttgtt ttgctggggt | 1680 |

| tcatcatgtg ggcctgccaa aaaggcaaca ttaggtgcaa catttgcatt tgagtgcatt | 1740 |
| aattaaaaac acccttgttt ctactaata | 1769 |

<210> SEQ ID NO 5
<211> LENGTH: 1572
<212> TYPE: DNA
<213> ORGANISM: Artificial Sequence
<220> FEATURE:
<223> OTHER INFORMATION: plasmid insert NP

<400> SEQUENCE: 5

| gggagcaaaa gcagggtaga taatcactca atgagtgaca tcgaagccat ggcgtctcaa | 60 |
| ggcaccaaac gatcatatga acaaatggag actggtgggg aacgccagga tgccacagaa | 120 |
| atcagagcat ctgtcggaag aatgattggt ggaatcggga gattctacat ccaaatgtgc | 180 |
| actgaactca aactcagtga ctatgaggga cgactaatcc aaaatagcat aacaatagag | 240 |
| agaatggtgc tctctgcttt tgatgagaga agaaataaat acctagaaga gcatcccagt | 300 |
| gctgggaagg atcctaagaa aactggagga cccatatata gaagagtaga cggaaagtgg | 360 |
| atgagagaac tcatccttta tgacaaagaa gaaataagga gagtttggcg ccaagcaaac | 420 |
| aatggtgaag atgcaacagc tggtcttact catatcatga tttggcattc caatctgaat | 480 |
| gatgccactt atcagagaac aagagcgctt gttcgcaccg gaatggatcc cagaatgtgc | 540 |
| tctctaatgc aaggttcaac acttcccaga aggtctgggg ccgcaggtgc tgcagtgaaa | 600 |
| ggagttggaa caatagcaat ggagttaatc agaatgatca aacgtgggat caatgaccga | 660 |
| aacttctgga gggtgaaaaa tggacgaagg acaaggattg catatgaaag aatgtgcaat | 720 |
| attctcaaag gaaaatttca gacagctgcc cagagggcaa tgatggatca agtgagagaa | 780 |
| agtcggaacc caggaaacgc tgagattgaa gatctcattt tcctggcacg gtcagcactt | 840 |
| attctaaggg gatcagttgc acataagtct tgcctgcctg cttgtgtgta tgggcttgca | 900 |
| gtagcaagtg ggcatgactt tgaaagggaa gggtattcac tggtcgggat agacccattt | 960 |
| aaattactcc aaaacagtca agtgttcagc ctgataagac caaatgaaaa cccagctcac | 1020 |
| aagagtcaat tggtgtggat ggcatgccac tctgctgcat tgaggatttt aagagtatca | 1080 |
| agtttcataa gagggaagaa agtgattcca gaggaaagc tttccacaag aggggttcag | 1140 |
| attgcttcaa atgagaatgt ggaagccatg gactccaata cccctagaact gagaagcaga | 1200 |
| tactgggcca taaggaccag gagtggagga aataccaatc aacagaaggc atccgcgggc | 1260 |
| cagatcagtg tgcaacctac attctcagtg caacggaatc tccctttga aagagcaacc | 1320 |
| gttatggcag ctttcagcgg gaacaatgaa ggacggacat ccgacatgag aacagaagtt | 1380 |
| ataaggatga tggaaagtgc aaagccagaa gatttgtcct tccaggggcg gggagtcttc | 1440 |
| gagctctcgg acgaaaaggc aacgagcccg atcgtgcctt cctttgacat gagtaatgaa | 1500 |
| gggtcttatt tcttcggaga caatgcagag gagtatgaca gttgaggaaa ataccccttg | 1560 |
| tttctactaa ta | 1572 |

<210> SEQ ID NO 6
<211> LENGTH: 1453
<212> TYPE: DNA
<213> ORGANISM: Artificial Sequence
<220> FEATURE:
<223> OTHER INFORMATION: plasmid insert NA

<400> SEQUENCE: 6

| | |
|---|---:|
| gatgaatcca aatcaaaaga taataacgat tggctctgtt tctctcacta ttgccacaat | 60 |
| gtgcttcctt atgcaaattg ccatcctggt aactactgta acattgcatt tcaagcaata | 120 |
| tgaatgcaac taccccccaa acaaccaagt aatactgtgt gaaccaacaa taatagaaag | 180 |
| aaacataaca gagatagtgt atctgaccaa caccaccata gagaaggaaa tatgccccaa | 240 |
| actagcagaa tacagaaatt ggtcaaagcc gcaatgtaaa attacaggat ttgcacctttt | 300 |
| ttccaaggac aattcgatta ggcttttccgc tggtggggac atttgggtga caagagaacc | 360 |
| ttatgtgtca tgcgatcctg acaagtgtta tcaatttgcc cttggacagg gaacaacact | 420 |
| aaacaacagg cattcaaatg acacagtaca tgataggacc ccttatcgaa ccctattgat | 480 |
| gaatgagttg ggtgttccat tcatttggg aaccaagcaa gtgtgcatag catggtccag | 540 |
| ctcaagttgt cacgatggaa aagcatggct gcatgtttgt gtaactgggc atgatgaaaa | 600 |
| tgcaactgct agcttcattt acgatgggag gcttgtagat agtattggtt catggtccaa | 660 |
| aaaaatcctc aggacccagg agtcggaatg cgtttgtatc aatggaactt gtacagtagt | 720 |
| aatgactgat gggagtgctt caggaagagc tgatactaaa atattattca ttgaggaggg | 780 |
| gaaaatcgtt catattagcc cattgttagg aagtgctcag catgtcgagg agtgctcctg | 840 |
| ttatcctcga tatcctggtg tcagatgtgt ctgcagagac aactggaaag gctccaatag | 900 |
| gcccatcgta gatataaatg taaaggatta tagcattgtt tccagttatg tgtgctcagg | 960 |
| acttgttgga gacacaccca gaaaaaacga cagatccagc agtagcaatt gcctgaatcc | 1020 |
| taacaatgag gaaggggtc atggagtgaa aggctgggcc tttgatgatg gaatgacgt | 1080 |
| gtggatggga agaacgatca acgagaagtt acgctcaggt tatgaaacct tcaaagtcat | 1140 |
| tgaaggctgg tccaaaccta actccaaatt gcagataaat aggcaagtca tagttgacag | 1200 |
| aggtgatagg tccggttatt ctggcatttt ctctgttgaa ggcaaaagct gcatcaatcg | 1260 |
| gtgcttttat gtggagttga taaggggaag gaaacaggaa actgaagtat ggtggaccctc | 1320 |
| aaacagtatt gttgtgtttt gtggcaccctc aggtacatat ggaacaggct catggcctga | 1380 |
| tggggcggac atcaatctca tgcctatata agctttcgca attttagaaa aaaactcctt | 1440 |
| gtttctacta ata | 1453 |

<210> SEQ ID NO 7
<211> LENGTH: 1032
<212> TYPE: DNA
<213> ORGANISM: Artificial Sequence
<220> FEATURE:
<223> OTHER INFORMATION: plasmid insert M

<400> SEQUENCE: 7

| | |
|---|---:|
| gggagcaaaa gcaggtagat gtttaaagat gagtcttcta accgaggtcg aaacgtatgt | 60 |
| tctctctatc gttccgtcag gccccctcaa agccgagata gcgcagagac tcgaagacgt | 120 |
| ttttgcaggg aaaaacaccg atcttgaggc actcatggaa tggctaaaga caagaccaat | 180 |
| cctgtcacct ctgactaagg ggattttagg atttgtgttc acgctcaccg tgcccagtga | 240 |
| gcgaggactg cagcgtagac gctttgtcca gaatgccctc aatgggaatg gtgacccgaa | 300 |
| caacatggac aaagcggtca aactgtacag gaaacttaaa agggaaataa cattccatgg | 360 |
| ggccaaagaa gtagcgctca gttactctgc tggtgcactt gccagttgca tgggcctcat | 420 |
| atataacaga atggggactg tcaccactga ggtggccttt ggtctagtat gcgcaacctg | 480 |
| tgaacagatt gctgattccc agcatcgatc tcatagacaa atggtgacaa caccaatcc | 540 |
| actaatcagg cacgagaaca gaatggtatt agccagtaca acagctaaag ccatggaaca | 600 |

```
aatggctgga tcaagcgaac aagcagcaga ggctatggag gttgccagcc aggctagaca    660
aatggtacag gcaatgagaa caattgggac tcaccctagt tccagtgctg gtctaaaaga    720
tgatcttctt gaaaatttac agacctatca gaaacggatg ggagtgcaaa tgcaacgatt    780
caagtgatcc tctcattgct gccgcaagca tcattgggat tttgcacctg atattgtgga    840
ttcttgatcg tctttttttc aaatacattt accgtcgctt taaatacggt ctgaaaagag    900
ggccttctac ggaaggagtg ccggagtcca tgagggaaga gtatcgacag aaacagcaga    960
gtgctgtgga tgttgacgat ggtcattttg tcaacatagt gctagagtaa aaaactacct   1020
tgtttctact aa                                                       1032

<210> SEQ ID NO 8
<211> LENGTH: 873
<212> TYPE: DNA
<213> ORGANISM: Artificial Sequence
<220> FEATURE:
<223> OTHER INFORMATION: NS

<400> SEQUENCE: 8
gggagcaaaa gcagggtgac aaagacataa tggactccaa cactgtgtca agctttcagg     60
tagactgttt cctttggcat atccgcaaac ggtttgcaga caatggattg ggtgatgccc    120
cattccttga tcggctccgc cgagatcaaa agtccctaaa aggaagaggc aacacccttg    180
gcctcgacat cgaaacagcc actcttgttg gaaacaaat tgtggagtgg atttttgaaag    240 aggaatccag cgagacactt aagatgacca ttgcatctgt acctacttcg cgctacctag    300
ctgacatgac cctcgaggaa atgtcacgag actggttcat gctcatgcct aggcaaaaga    360
taataggctc tctttgtgtg cgaatggacc aggcgatcat ggaaaagaac atcatactga    420
aagcgaactt cagtgtgatc tttaaccgat tagagacttt gatactacta agggctttca    480
ctgaggaggg agcaatcgtt ggagaaattt caccattacc ttctcttcca ggacatactg    540
atgaggatgt caaaaatgca gttggggtcc tcatcggagg acttgaatgg aatggtaaca    600
cggttcgagt ctctgaaaat ctacagagat tcgcttggag aaaccgtaat gaggatggga    660
gaccttcact acctccagag cagaaatgaa aagtggcgag agcaattggg acagaaattt    720
gaggaaataa ggtggttaat tgaagaagtg cggcacagat tgaaagcgac agagaatagt    780
ttcgaacaaa taacatttat gcaagcctta caactactgc ttgaagtaga acaagagata    840 agaacttct cgtttcagct tatttaatga taa                                 873

<210> SEQ ID NO 9
<211> LENGTH: 27
<212> TYPE: DNA
<213> ORGANISM: Artificial Sequence
<220> FEATURE:
<223> OTHER INFORMATION: oligo pHW-3' (reverse) for annealing in the
      plasmid pHW2000 backbone

<400> SEQUENCE: 9
gggtcaagga aggcacgggg gaggggc                                         27

<210> SEQ ID NO 10
<211> LENGTH: 31
<212> TYPE: DNA
<213> ORGANISM: Artificial Sequence
<220> FEATURE:
<223> OTHER INFORMATION: oligo 5'NS-PacI for annealing in the NS1 gene

<400> SEQUENCE: 10
```
gcgcttaatt aagagggagc aatcgttgga g                                        31

<210> SEQ ID NO 11
<211> LENGTH: 31
<212> TYPE: DNA
<213> ORGANISM: Artificial Sequence
<220> FEATURE:
<223> OTHER INFORMATION: primer CMV5' annealing in the CMV promoter of
      pHW2000 plasmid

<400> SEQUENCE: 11
gccccattga cgcaaatggg cggtaggcgt g                                        31

<210> SEQ ID NO 12
<211> LENGTH: 42
<212> TYPE: DNA
<213> ORGANISM: Artificial Sequence
<220> FEATURE:
<223> OTHER INFORMATION: reverse primer NS73- BglII-PacI-3' annealing
      in the NS1 gene

<400> SEQUENCE: 12
gcgcttaatt aatcaagatc taggattcct ctttcaaaat cc                            42

<210> SEQ ID NO 13
<211> LENGTH: 42
<212> TYPE: DNA
<213> ORGANISM: Artificial Sequence
<220> FEATURE:
<223> OTHER INFORMATION: primer NS99-BglII-PacI-3'

<400> SEQUENCE: 13
gcttaattaa tcaagatcta tgacatttcc tcgagggtca tg                            42

<210> SEQ ID NO 14
<211> LENGTH: 44
<212> TYPE: DNA
<213> ORGANISM: Artificial Sequence
<220> FEATURE:
<223> OTHER INFORMATION: primer NS126-BglII-PacI-3'

<400> SEQUENCE: 14
gcgcttaatt aatcaagatc tacttttcca tgatcgcctg gtcc                          44

<210> SEQ ID NO 15
<211> LENGTH: 23
<212> TYPE: DNA
<213> ORGANISM: Artificial Sequence
<220> FEATURE:
<223> OTHER INFORMATION: specific primer 5-SWIFNB+ for swine IFN-beta

<400> SEQUENCE: 15
ggccatggct aacaagtgca tcc                                                 23

<210> SEQ ID NO 16
<211> LENGTH: 22
<212> TYPE: DNA
<213> ORGANISM: Artificial Sequence
<220> FEATURE:
<223> OTHER INFORMATION: specific primer 3-SWIFNB- for swine IFN-beta

<400> SEQUENCE: 16
ccggtcagtt ccggaggtaa tc                                                  22

<210> SEQ ID NO 17

```
<211> LENGTH: 18
<212> TYPE: DNA
<213> ORGANISM: Artificial Sequence
<220> FEATURE:
<223> OTHER INFORMATION: primer 5'SW-TNFA for NF-a (see Genbank
      accession No. M86762)

<400> SEQUENCE: 17
atgagcactg agagcatg                                                 18

<210> SEQ ID NO 18
<211> LENGTH: 18
<212> TYPE: DNA
<213> ORGANISM: Artificial Sequence
<220> FEATURE:
<223> OTHER INFORMATION: primer 3'SW-TNFA (see Genbank accession No.
      X57321)

<400> SEQUENCE: 18
tcacagggca atgatccc                                                 18

<210> SEQ ID NO 19
<211> LENGTH: 30
<212> TYPE: DNA
<213> ORGANISM: Artificial Sequence
<220> FEATURE:
<223> OTHER INFORMATION: oligonucleotide used to introduce mutation in
      NS1 gene (1-73)

<400> SEQUENCE: 19
gaatcctaga tcttgattaa ttaagaggga                                    30

<210> SEQ ID NO 20
<211> LENGTH: 30
<212> TYPE: DNA
<213> ORGANISM: Artificial Sequence
<220> FEATURE:
<223> OTHER INFORMATION: oligonucleotide used to introduce mutation in
      NS1 gene (1-99)

<400> SEQUENCE: 20
atgtcataga tcttgattaa ttaagaggga                                    30

<210> SEQ ID NO 21
<211> LENGTH: 30
<212> TYPE: DNA
<213> ORGANISM: Artificial Sequence
<220> FEATURE:
<223> OTHER INFORMATION: oligonucleotide used to introduce mutation in
      NS1 gene (1-126)

<400> SEQUENCE: 21
gaaaagtaga tcttgattaa ttaagaggga                                    30
```

GENETICALLY ENGINEERED SWINE INFLUENZA VIRUS AND USES THEREOF

This application is a divisional of U.S. application Ser. No. 14/636,651, filed Mar. 3, 2015, now U.S. Pat. No. 9,549,975, which is a divisional application of U.S. application Ser. No. 13/304,175, filed Nov. 23, 2011, now U.S. Pat. No. 8,999,352, which is a divisional of U.S. application Ser. No. 11/628,292, filed Feb. 6, 2008, now U.S. Pat. No. 8,124,101, which is the National Stage of International Application No. PCT/US2005/019382, filed Jun. 1, 2005, which claims the benefit under 35 U.S.C. 119(e) of U.S. Provisional Application No. 60/576,418, filed Jun. 1, 2004, each of which is incorporated by reference herein in its entirety.

This invention was made with government support under grant number AI095357 awarded by the National Institutes of Health. The government has certain rights in the invention.

The present specification contains a Sequence Listing, which has been submitted in electronic format via EFS-Web and is hereby incorporated by reference in its entirety. The Sequence Listing is provided as a computer readable format (CRF) file entitled SEQLIST 6923-265-999, which was created on Feb. 12, 2017, and is 20,827 bytes in size.

1. FIELD OF THE INVENTION

The present invention relates, in general, to attenuated swine influenza viruses having an impaired ability to antagonize the cellular interferon (IFN) response, and the use of such attenuated viruses in vaccine and pharmaceutical formulations. In particular, the invention relates to attenuated swine influenza viruses having modifications to a swine NS1 gene that diminish or eliminate the ability of the NS1 gene product to antagonize the cellular IFN response. These viruses replicate in vivo, but demonstrate decreased virulence and increased attenuation, and therefore are well suited for use in live virus vaccines, and pharmaceutical formulations.

2. BACKGROUND

2.1 Influenza Virus

Virus families containing enveloped single-stranded RNA of the negative-sense genome are classified into groups having non-segmented genomes (Paramyxoviridae, Rhabdoviridae, Filoviridae and Borna Disease Virus) or those having segmented genomes (Orthomyxoviridae, Bunyaviridae and Arenaviridae). The Orthomyxoviridae family, described in detail below, and used in the examples herein, includes the viruses of influenza, types A, B and C viruses, as well as Thogoto and Dhori viruses and infectious salmon anemia virus.

The influenza virions consist of an internal ribonucleoprotein core (a helical nucleocapsid) containing the single-stranded RNA genome, and an outer lipoprotein envelope lined inside by a matrix protein (M1). The segmented genome of influenza A virus consists of eight molecules (seven for influenza C) of linear, negative polarity, single-stranded RNAs which encode eleven polypeptides, including: the RNA-dependent RNA polymerase proteins (PB2, PB1 and PA) and nucleoprotein (NP) which form the nucleocapsid; the matrix membrane proteins (M1, M2); two surface glycoproteins which project from the lipid containing envelope: hemagglutinin (HA) and neuraminidase (NA); the nonstructural protein (NS1), nuclear export protein (NEP); and the proapoptotic factor PB1-F2. Transcription and replication of the genome takes place in the nucleus and assembly occurs via budding on the plasma membrane. The viruses can reassort genes during mixed infections.

Influenza virus adsorbs via HA to sialyloligosaccharides in cell membrane glycoproteins and glycolipids. Following endocytosis of the virion, a conformational change in the HA molecule occurs within the cellular endosome which facilitates membrane fusion, thus triggering uncoating. The nucleocapsid migrates to the nucleus where viral mRNA is transcribed. Viral mRNA is transcribed by a unique mechanism in which viral endonuclease cleaves the capped 5'-terminus from cellular heterologous mRNAs which then serve as primers for transcription of viral RNA templates by the viral transcriptase. Transcripts terminate at sites 15 to 22 bases from the ends of their templates, where oligo(U) sequences act as signals for the addition of poly(A) tracts. Of the eight viral RNA molecules so produced, six are monocistronic messages that are translated directly into the proteins representing HA, NA, NP and the viral polymerase proteins, PB2, PB1 and PA. The other two transcripts undergo splicing, each yielding two mRNAs which are translated in different reading frames to produce M1, M2, NS1 and NEP. The PB1 segment encodes a second protein, the nonstructural PB1-F2 protein, by using of an alternative ATG. In other words, the eight viral RNA segments code for eleven proteins: nine structural and two nonstructural. A summary of the genes of the influenza virus and their protein products is shown in Table I below.

TABLE I

INFLUENZA VIRUS GENOME RNA SEGMENTS AND CODING ASSIGNMENTS[a]

| Segment | Length[b] (Nucleotides) | Encoded Polypeptide[c] | Length[d] (Amino Acids) | Molecules Per Virion | Comments |
|---|---|---|---|---|---|
| 1 | 2341 | PB2 | 759 | 30-60 | RNA transcriptase component; host cell RNA cap binding |
| 2 | 2341 | PB1 | 757 | 30-60 | RNA transcriptase component; initiation of transcription |
|   |      | PB1-F2 | 87 |  | Proapoptotic factor |
| 3 | 2233 | PA | 716 | 30-60 | RNA transcriptase component |
| 4 | 1778 | HA | 566 | 500 | Hemagglutinin; trimer; envelope glycoprotein; mediates attachment to cells |
| 5 | 1565 | NP | 498 | 1000 | Nucleoprotein; associated with RNA; structural component of RNA transcriptase |
| 6 | 1413 | NA | 454 | 100 | Neuraminidase; tetramer; envelope glycoprotein |

TABLE I-continued

INFLUENZA VIRUS GENOME RNA SEGMENTS
AND CODING ASSIGNMENTS[a]

| Segment | Length[b] (Nucleotides) | Encoded Polypeptide[c] | Length[d] (Amino Acids) | Molecules Per Virion | Comments |
|---|---|---|---|---|---|
| 7 | 1027 | $M_1$ | 252 | 3000 | Matrix protein; lines inside of envelope |
|   |      | $M_2$ | 96  | ?    | Structural protein in plasma membrane; spliced mRNA |
| 8 | 890  | $NS_1$ | 230 |     | Nonstructural protein; function unknown |
|   |      | NEP   | 121 | ?    | Nuclear export protein; spliced mRNA |

[a]Adapted from R. A. Lamb and P. W. Choppin (1983), Annual Review of Biochemistry, Volume 52, 467-506.
[b]For A/PR/8/34 strain
[c]Determined by biochemical and genetic approaches
[d]Determined by nucleotide sequence analysis and protein sequencing The pathogenicity of influenza viruses is modulated by multiple virus and host factors. Among the host factors that fight virus infections, the type I interferon (IFNα/β) system represents a powerful antiviral innate defense mechanism which was established relatively early in the evolution of eukaryotic organisms (Garcia-Sastre, 2002, Microbes Infect 4:647-55). The antiviral IFNα/β system involves three major steps: (i) detection of viral infection and IFNα/β secretion, (ii) binding of IFNα/β to its receptors and transcriptional induction of IFNα/β-stimulated genes, and (iii) synthesis of antiviral enzymes and proteins. Most viruses, however, have acquired specific genetic information encoding IFNα/β antagonist molecules, which effectively block one or more steps of the antiviral IFNα/β system. Influenza A viruses express a non-structural protein in infected cells, the NS1 protein (described in detail, infra), which counteracts the cellular IFNα/β response (Garcia-Sastre et al., 1998, Virology 252:324-30).

The influenza A virus genome contains eight segments of single-stranded RNA of negative polarity, coding for two nonstructural and nine structural proteins. The nonstructural protein NS1 is abundant in influenza virus infected cells, but has not been detected in virions. NS1 is a phosphoprotein found in the nucleus early during infection and also in the cytoplasm at later times of the viral cycle (King et al., 1975, Virology 64: 378). Studies with temperature-sensitive (ts) influenza mutants carrying lesions in the NS gene suggested that the NS1 protein is a transcriptional and post-transcriptional regulator of mechanisms by which the virus is able to inhibit host cell gene expression and to stimulate viral protein synthesis. Like many other proteins that regulate post-transcriptional processes, the NS1 protein interacts with specific RNA sequences and structures. The NS1 protein has been reported to bind to different RNA species including: vRNA, poly-A, U6 snRNA, 5' untranslated region as of viral mRNAs and ds RNA (Qiu et al., 1995, RNA 1: 304; Qiu et al., 1994, J. Virol. 68: 2425; Hatada Fukuda 1992, J Gen Virol. 73:3325-9. Expression of the NS1 protein from cDNA in transfected cells has been associated with several effects: inhibition of nucleo-cytoplasmic transport of mRNA, inhibition of pre-mRNA splicing, inhibition of host mRNA polyadenylation and stimulation of translation of viral mRNA (Fortes, et al., 1994, EMBO J. 13: 704; Enami et al., 1994, J. Virol. 68: 1432; de la Luna et al., 1995, J. Virol. 69:2427; Lu et al., 1994, Genes Dev. 8:1817; Park et al., 1995, J. Biol Chem. 270, 28433; Nemeroff et al., 1998, Mol. Cell. 1:1991; Chen et al., 1994, EMBO J. 18:2273-83). In particular, the NS1 protein has three domains that have been reported to have a number of regulatory functions during influenza virus infection. The amino-terminal 73 amino acids are responsible for binding to RNAs (Qian et al., 1995, RNA 1:948-956), particularly double stranded RNAs, conferring to the virus the ability to escape the interferon α/β response (Donelan et al., 2003, J. Virol. 77:13257-66). The central portion of the protein interacts with the eukaryotic translation initiation factor 4GI facilitating preferential translation of viral mRNAs over host mRNAs (Aragon et al., 2000, Mol. Cell Biol. 20:6259-6268). The carboxy-terminus or the effector domain has been shown to inhibit host mRNA processing, specifically, inhibition of host mRNA polyadenylation (Nemeroff et al., 1998, Mol. Cell 1:991-1000), binding to poly(A) tails of mRNA inhibiting nuclear export (Qiu and Krug, 1994, J. Virol. 68:2425-2432) and inhibition of pre-mRNA splicing (Lu et al., 1994, Genes Dev. 8:1817-1828).

Studies of human recombinant influenza virus lacking the NS1 gene (delNS1) showed that this virus could only replicate in IFN-incompetent systems such as STAT1−/− mice or Vero cells; thus the NS1 protein is responsible for IFN antagonist activity (Garcia-Sastre et al., 1998, Virology 252:324-330). Also, it has been shown that human influenza viruses with truncated NS1 proteins are attenuated in mice (Egorov et al., 1998, J. Virol. 72:6437-6441) and provide protection against wild-type challenge (Talon et al., 2000, Proc. Natl. Acad. Sci. USA 97:4309-4314).

2.2 Swine Influenza Virus

Swine influenza (SI) is an acute respiratory disease of swine caused by type A influenza viruses. Its severity depends on many factors, including host age, virus strain, and secondary infections (Easterday, 1980, Philos Trans R Soc Lond B Biol Sci 288:433-7). Influenza A viruses are segmented negative-strand RNA viruses and can be isolated from a number of other animal host species, including birds, humans, horses, whales, and mink. Although whole influenza viruses rarely cross the species barrier, gene segments can cross this barrier through the process of genetic reassortment, or genetic shift. Since pigs support the replication of both human and avian influenza A viruses (Kida et al., 1994, J Gen Virol 75:2183-8), they have been postulated to play an important role in interspecies transmission by acting as a "mixing vessel" for reassortment between viruses specific to different host species (Scholtissek, 1994, Eur J Epidemiol 10:455-8). This may lead to the generation of novel influenza viruses capable of crossing the species barrier to humans. There are three subtypes of SI viruses (SIV) currently circulating in pigs in the U.S.: H1N1, H3N2, and H1N2 (Olsen, 2002, Virus Res 85:199-210; Karasin et al., 2002, J Clin Microbiol 40:1073-9; Karasin et al., 2000, Virus Res 68:71-85; Olsen et al., 2000, Arch Virol 145:1399-419; Webby et al., 2000, J Virol 74:8243-51; Webby et al., 2001, Philos Trans R Soc Lond B Biol Sci 356:1817-28; Zhou, 2000, Vet Microbiol 74:47-58). Before 1998, mainly "classical" H1N1 SIVs were isolated from swine in the United States (Kida et al., 1994, J Gen Virol 75:2183-8; Scholtissek, 1994, Eur J Epidemiol 10:455-8; Olsen et al., 2000, Arch Virol. 145:1399-419). In 1998, SIVs of the subtype H3N2 were isolated in multiple states in the United States. These viruses were generated by reassortment between human, avian and classical swine viruses, they are undergoing rapid evolution and in general they cause more severe disease than classical H1N1 SIV.

Pathogenicity of influenza viruses is modulated by multiple virus and host factors. Among the host factors that fight virus infections, the type I interferon (IFNα/β) system represents a powerful antiviral innate defense mechanism which was established relatively early in the evolution of eukaryotic organisms (Garcia-Sastre, 2002, *Microbes Infect* 4:647-55). The antiviral IFNα/β system involves three major steps: (i) detection of viral infection and IFNα/β secretion, (ii) binding of IFNα/β to its receptors and transcriptional induction of IFNα/β-stimulated genes, and (iii) synthesis of antiviral enzymes and proteins. Most viruses, however, have acquired specific genetic information encoding IFNα/β antagonist molecules, which effectively block one or more steps of the antiviral IFNα/β system. Influenza A viruses express a non-structural protein in infected cells, the NS1 protein, which counteracts the cellular IFNα/β response (Garcia-Sastre et al., 1998, *Virology* 252:324-30).

Influenza infection in pigs was first reported in 1918 and the first swine influenza viruses were isolated from pigs in 1930 (Shope, R. E., 1931, *J. Exp. Med.* 54:373-385). These first isolates were the progenitors of what is recognized as the H1N1 lineage of swine influenza A viruses. From 1930 to the 1990s, influenza in North American pigs was caused almost exclusively by infection with H1N1 swine viruses. A dramatic shift in the pattern of swine influenza began around 1997, when an unexpected and substantial increase in H3 seropositivity (8%) was detected, and H3N2 viruses began to be isolated from pigs in both the US and Canada (Olsen et al., 2000, *Arch. Virol.* 134:1399-1419). Furthermore, reassortment between H3N2 viruses and H1N1 swine viruses resulted in the detection of second generation H1N2 reassortant viruses (Karasin et al., 2000, *J. Clin. Microbiol.* 38:2453-2456; Karasin et al., 2002, *J. Clin Microbiol.* 40:1073-1079). In addition, avian H4N6 viruses of duck origin have been isolated from pigs in Canada (Karasin et al., 2000, *J. Virol.* 74:9322-9327). The generation of these novel viruses in addition to the described antigenic drift variants of H1N1 swine influenza viruses, introduce potential veterinary and human public health implications.

In 1998, a new strain of swine influenza virus to which pigs had little immunity sickened every pig in an operation of 2400 animals. Although there has been only one influenza subtype which has sickened North American pigs since 1930, in the last few years a quick succession of new flu viruses has been sweeping through North America's 100 million pigs. After years of stability, the North American swine flu virus has jumped onto an evolutionary fast track, bringing out variants every year. This has had not only an undesired effect on the farming industry and a negative economic impact, but, there is also concern by experts that the evolving swine flu increases the likelihood that a novel virus will arise that is transmissible among humans. Fortunately, the new pig strains that have appeared in North America so far do not appear to readily infect humans.

2.3 Attenuated Viruses

Inactivated virus vaccines are prepared by "killing" the viral pathogen, e.g., by heat or formalin treatment, so that it is not capable of replication. Inactivated vaccines have limited utility because they do not provide long lasting immunity and, therefore, afford limited protection. An alternative approach for producing virus vaccines involves the use of attenuated live virus vaccines. Attenuated viruses are capable of replication but are not pathogenic, and, therefore, provide for longer lasting immunity and afford greater protection. However, the conventional methods for producing attenuated viruses involve the chance isolation of host range mutants, many of which are temperature sensitive; e.g., the virus is passaged through unnatural hosts, and progeny viruses which are immunogenic, yet not pathogenic, are selected.

A conventional substrate for isolating and growing influenza viruses for vaccine purposes are embryonated chicken eggs. Influenza viruses are typically grown during 2-4 days at 37° C. in 10-12 day old eggs. Although most of the human primary isolates of influenza A and B viruses grow better in the amniotic sac of the embryos, after 2 to 3 passages the viruses become adapted to grow in the cells of the allantoic cavity, which is accessible from the outside of the egg (Murphy, B. R., and R. G. Webster, 1996. Orthomyxoviruses pp. 1397-1445. In Fields Virology. Lippincott-Raven P.A.).

Recombinant DNA technology and genetic engineering techniques, in theory, would afford a superior approach to producing an attenuated virus since specific mutations could be deliberately engineered into the viral genome. However, the genetic alterations required for attenuation of viruses are not known or predictable. In general, the attempts to use recombinant DNA technology to engineer viral vaccines have mostly been directed to the production of subunit vaccines which contain only the protein subunits of the pathogen involved in the immune response, expressed in recombinant viral vectors such as vaccinia virus or baculovirus. More recently, recombinant DNA techniques have been utilized in an attempt to produce herpes virus deletion mutants or polioviruses which mimic attenuated viruses found in nature or known host range mutants. Until 1990, the negative strand RNA viruses were not amenable to site-specific manipulation at all, and thus could not be genetically engineered.

Although these viruses are beneficial because they are immunogenic and not pathogenic, they are difficult to propagate in conventional substrates for the purposes of making vaccines. Furthermore, attenuated viruses may possess virulence characteristics that are so mild as to not allow the host to mount an immune response sufficient to meet subsequent challenges.

Human influenza viruses does not replicate efficiently in birds, and vice versa due to differences in receptors which bind the viruses. In contrast, pigs are uniquely susceptible to infection with human and avian viruses because they possess receptor types present both in humans and avian influenza viruses. As a result, pigs have been hypothesized to be the "mixing vessel" hosts for human-avian virus reassortment and there is support for this theory from several studies. See, e.g., Shu et al., 1994, Virology 202:825-33; Scholtissek, 1990, Med. Principles Pract. 2:65-71; Zhou et al., 1999 J Virol. 73:8851-6. This mixing facilitates the generation of novel human influenza virus strains and the initiation of influenza pandemics.

Inactivated or "killed" influenza virus preparations are the only influenza vaccines currently licensed in the United States. An alternative approach for producing virus vaccines to the inactivated virus vaccines in which the viral pathogen is "killed", involves the use of attenuated live virus vaccines which are capable of replication but are not pathogenic. Live vaccines which are administered intranasally may have advantages over their inactivated counterparts. Firstly, live vaccines are thought to induce improved cross-reactive cell-mediated cytotoxicity as well as a humoral antibody response, providing better protection than inactivated vaccines (Gorse and Belshe, 1990, J. Clin. Microbiol. 28:2539-2550; and Gorse et al., 1995, J. Infect. Dis. 172:1-10). Secondly, live vaccines also have the advantage of intranasal administration which avoids the swelling and muscle soreness occasionally associated with the intramuscular administration of inactivated adjuvanted vaccines. These live vaccines have been reported to induce not only humoral responses against homotypic influenza virus but also cross-reactive cell-mediated cytotoxicity. Further advantages of live vaccines include the ease of intranasal administration, induction of mucosal immunity, longer lasting immunity, and its cost effectiveness. These are all important considerations regarding potential swine influenza vaccines.

Thus, new and more effective vaccines and immunogenic formulations for preventing swine influenza virus infections generated by such technology are needed.

3. SUMMARY OF THE INVENTION

The present invention provides attenuated swine influenza viruses having an impaired ability to antagonize the cellular interferon (IFN) response, methods for producing such attenuated swine influenza viruses, and the use of such viruses in vaccine and pharmaceutical formulations. Such viruses are capable of generating an immune response and creating immunity but not causing illness or causing fewer and/or less severe symptoms, i.e., the viruses have decreased virulence. Therefore, they are ideal candidates for live virus vaccines. Moreover, the attenuated viruses can induce a robust IFN response which has other biological consequences in vivo, affording protection against subsequent infectious diseases and/or inducing antitumor responses. Therefore, the attenuated viruses can be used pharmaceutically, for the prevention or treatment of other infectious diseases and/or IFN-treatable diseases.

The invention is based, in part, on the Applicants' discovery that swine influenza viruses engineered to contain or containing a deletion(s) in the NS1 gene have impaired replication relative to wild-type swine influenza viruses as demonstrated by fewer lung lesions upon infection of pigs, reduced viral titers in bronchoalveolar lavage fluid (BALF) and reduced detection of virus on nasal swabs. Surprisingly, and contrary to results seen with human influenza virus in mouse models, the length of the NS1 protein does not correlate with the level of attenuation of the swine influenza virus. Applicants have discovered that with swine influenza, a mutant virus with the shortest NS1 protein is the least attenuated. In other words, swine influenza viruses containing shorter deletions in the NS1 gene exhibit a greater attenuation in vivo than swine influenza viruses containing longer deletions in their NS1 gene, or wild type swine influenza viruses. Applicants have further discovered that the recombinant swine influenza viruses are impaired in their ability to inhibit IFN production in vitro, and they do not replicate as efficiently as the parental recombinant strain in 10-day old embryonated hen eggs, in MDCK cells, in PK-15 cells or in an in vivo pig model. While not intending to be bound to any theory or explanation for the mechanism of action of the swine influenza virus NS1 deletion mutants in vivo, the attenuated features of such viruses are presumably due to their levels of NS1 protein expression, their ability to induce a robust cellular IFN response, and their impaired ability to antagonize such a response. However, the beneficial features of such viruses may not be solely attributable to their effect on the cellular interferon response. Indeed, alterations in other activities associated with NS1, such as, alteration of pre-mRNA splicing, inhibition of cellular mRNA polyadenylation, poly(A)-containing mRNA nucleocytoplasmic transport, and stimulation of viral protein synthesis, may contribute to the desired attenuated phenotype achieved by the introduction of mutations in the NS1 gene of swine influenza virus.

An attenuated swine influenza virus of the present invention comprises a mutation in a swine influenza NS1 gene that diminishes the ability of the NS1 gene product to antagonize the cellular interferon response. In one embodiment, an attenuated swine influenza virus of the invention comprises a genome comprising a mutation in a swine influenza virus NS1 gene that diminishes the ability of the NS1 gene product to antagonize a cellular interferon response, and permits the attenuated virus, at a multiplicity of infection (MOI) of between 0.0005 and 0.001, 0.001 and 0.01, 0.01 and 0.1, or 0.1 and 1, or a MOI of 0.0005, 0.0007, 0.001, 0.005, 0.01, 0.05, 0.1, 0.5, 1.0, 1.5, 2.0, 2.5, 3.0, 3.5, 4.0, 4.5, 5.0, 5.5, or 6.0, to grow to titers between approximately 1 to approximately 100 fold, approximately 5 to approximately 80 fold, approximately 20 to approximately 80 fold, or approximately 40 to approximately 80 fold, approximately 1 to approximately 10 fold, approximately 1 to approximately 5 fold, approximately 1 to approximately 4 fold, approximately 1 to approximately 3 fold, approximately 1 to approximately 2 fold, approximately 3 to approximately 15 fold, or approximately 1, 2, 3, 4, 5, 6, 7, 8, 10, 15, 20, 25, 30, 35, 40, 45, 50, 55, 60, 65, 70, 75, 80, 85, 90, 95 or 100 fold lower than wild-type swine influenza virus in cells (e.g., cells of a human (e.g., PerC6, a producer cell line derived from human embryonic retinoblasts transformed with the E1 region of Adenovirus 5), mouse, chicken (e.g., chicken embryo fibroblasts), rat, birds, or pig (e.g., PK(D1) cells, PK(15) cells, PK13 cells, NSK cells, LLC-PK1 cells, LLC-PK1A cells, ESK-4 cells, ST cells, PT-K75 cells, PK-2a/CL 13 or SJPL cells)), as determined approximately 2 to 10 days, 3 to 7 days, 3 to 5 days, or 2, 3, 4, 5, 6, 7, 8, 9, 10 days post-infection when propagated under the same conditions. The titers of attenuated and wild-type swine influenza viruses can be determined utilizing any technique well-known in the art or described herein, (e.g., hemagglutination assays, plaque assays, tissue culture infectious dose 50 (TCID50), egg infectious dose 50 (EID50), etc.) and the viruses can be propagated under conditions described herein or well-known in the art (e.g., in pig cells, MDCK cells (e.g., in MEM, 10% v/v fetal calf serum (FCS), 1% penicillin/ streptomycin at 37° C. in a 5% $CO_2$ humidified incubator) or embryonated chicken eggs (e.g., in a stationary incubator at 37° C. with 55% relative humidity). Alternatively, the viruses can be propagated in cells (e.g., in pig cells, MDCK cells, etc.) that are grown in serum-free or serum reduced (e.g., TPCK trypsin) medium.

In a specific embodiment, an attenuated swine influenza virus of the invention comprises a genome comprising a mutation in a swine influenza virus NS1 gene that diminishes the ability of the NS1 gene product to antagonize a cellular interferon response, and permits the attenuated virus, at a multiplicity of infection (MOI) of between 0.0005 and 0.001, 0.001 and 0.01, 0.01 and 0.1, or 0.1 and 1, or a MOI of 0.0005, 0.0007, 0.001, 0.005, 0.01, 0.05, 0.1, 0.5, 1.0, 1.5, 2.0, 2.5, 3.0, 3.5, 4.0, 4.5, 5.0, 5.5, or 6.0, to grow to titers between approximately 1 to approximately 100 fold, approximately 5 to approximately 80 fold, approximately 20 to approximately 80 fold, or approximately 40 to approximately 80 fold, approximately 1 to approximately 10 fold, approximately 1 to approximately 5 fold, approximately 1 to approximately 4 fold, approximately 1 to approximately 3 fold, approximately 1 to approximately 2 fold, approximately 3 to approximately 15 fold, or approximately 1, 2, 3, 4, 5, 6, 7, 8, 10, 15, 20, 25, 30, 35, 40, 45, 50, 55, 60, 65, 70, 75, 80, 85, 90, 95 or 100 fold lower than wild-type swine influenza virus in cells (e.g., cells of a human (e.g., PerC6, a producer cell line derived from human embryonic retinoblasts transformed with the E1 region of Adenovirus 5), mouse, chicken (e.g., chicken embryo fibroblasts), rat, birds, or pig (e.g., PK(D1) cells, PK(15) cells, PK13 cells, NSK cells, LLC-PK1 cells, LLC-PK1A cells, ESK-4 cells, ST cells, PT-K75 cells, PK-2a/CL 13 or SJPL cells)), as determined approximately 2 to 10 days, 3 to 7 days, 3 to 5 days, or 2, 3, 4, 5, 6, 7, 8, 9, 10 days post-infection when propagated under the same conditions. The titers of attenuated and wild-type swine influenza viruses can be determined utilizing any technique well-known in the art or described herein, (e.g., hemagglutination assays, plaque assays, etc.) and the viruses can be propagated under conditions described herein or well-known in the art (e.g., in pig cells, MDCK cells (e.g., in MEM, 10% v/v fetal calf serum (FCS), 1% penicillin/streptomycin at 37° C. in a 5% $CO_2$ humidified incubator) or embryonated chicken eggs (e.g., in a stationary incubator at 37° C. with 55% relative humidity).

The swine influenza viruses used in accordance with the invention may be selected from naturally occurring strains, variants or mutants; mutagenized viruses (e.g., viruses generated by exposure to mutagens, repeated passages and/or passage in non-permissive hosts); reassortants; and/or genetically engineered viruses (e.g., using the "reverse genetics" and helper-free plasmid-based techniques) having the desired phenotype—i.e., an impaired ability to antagonize the cellular IFN response. The naturally occurring strains, variants or mutants, reassortments and/or genetically engineered viruses with the desired interferon antagonist phenotype can be selected based on differential growth in cells (e.g., cells of a human (e.g., PerC6, a producer cell line derived from human embryonic retinoblasts transformed with the E1 region of Adenovirus 5), mouse, chicken (e.g., chicken embryo fibroblasts), rat, birds, or pig (e.g., PK(D1) cells, PK(15) cells, PK13 cells, NSK cells, LLC-PK1 cells, LLC-PK1A cells, ESK-4 cells, ST cells, PT-K75 cells, PK-2a/CL 13 or SJPL cells)) in other assays described below. In certain embodiments, the swine influenza viruses of the invention are genetically engineered viruses. In other embodiments, the swine influenza viruses of the invention are not naturally occurring strains, variants or mutants and/or reassortments.

In a specific embodiment, an attenuated swine influenza virus of the invention comprises a genome comprising a mutation in a swine influenza virus NS1 gene that diminishes the ability of the NS1 gene product to antagonize a cellular interferon response, and permits the attenuated virus, at a multiplicity of infection (MOI) of between 0.0005 and 0.001, 0.001 and 0.01, 0.01 and 0.1, or 0.1 and 1, or a MOI of 0.0005, 0.0007, 0.001, 0.005, 0.01, 0.05, 0.1, 0.5, 1.0, 1.5, 2.0, 2.5, 3.0, 3.5, 4.0, 4.5, 5.0, 5.5, or 6.0, to grow to titers between approximately 1 to approximately 100 fold, approximately 5 to approximately 80 fold, approximately 20 to approximately 80 fold, or approximately 40 to approximately 80 fold, approximately 1 to approximately 10 fold, approximately 1 to approximately 5 fold, approximately 1 to approximately 4 fold, approximately 1 to approximately 3 fold, approximately 1 to approximately 2 fold, approximately 3 to approximately 15 fold, or approximately 1, 2, 3, 4, 5, 6, 7, 8, 10, 15, 20, 25, 30, 35, 40, 45, 50, 55, 60, 65, 70, 75, 80, 85, 90, 95 or 100 fold lower than wild-type swine influenza virus in cells (e.g., cells of a human (e.g., PerC6, a producer cell line derived from human embryonic retinoblasts transformed with the E1 region of Adenovirus 5), mouse, chicken (e.g., chicken embryo fibroblasts), rat, birds, or pig (e.g., PK(D1) cells, PK(15) cells, PK13 cells, NSK cells, LLC-PK1 cells, LLC-PK1A cells, ESK-4 cells, ST cells, PT-K75 cells, PK-2a/CL 13 or SJPL cells)) as determined by a hemagglutination assay of BALF from pigs or supernatants of pig cells approximately 2 to 10 days, 3 to 7 days, 3 to 5 days, or 2, 3, 5, 6, 7, 8, 9, 10 days post-infection or when the viruses are plagued on Madin-Darby canine kidney (MDCK) cells. In one embodiment, the growth of an attenuated swine influenza virus of the invention is compared to a particular standard or reference, e.g., wild-type swine influenza virus A/Swine/Texas/4199-2/98. In accordance with these embodiments, the attenuated virus may be genetically engineered to contain or express non-swine influenza virus nucleic acid sequences such, e.g., an epitope of a foreign pathogen or a tumor antigen. Preferably, the non-swine influenza virus sequences do not include a nucleic acid sequence that alters the attenuated phenotype of the virus. Accordingly, nucleic acid sequences encoding proteins, polypeptides or peptides with interferon antagonizing activity are preferably not engineered into a swine influenza virus.

The invention provides attenuated swine influenza viruses comprising a genome comprising at least two, at least three, at least four or more mutations in two, three, four or more swine influenza virus genes, wherein at least one of the mutations is in the NS1 gene and contributes to or is responsible (directly or indirectly) for the attenuation of the virus and/or the diminished ability of the virus to antagonize a cellular interferon response. In one embodiment, an attenuated swine influenza virus of the invention comprises a genome comprising at least two, at least three, at least four or more mutations in two, three, four or more swine influenza virus genes, wherein at least one of the mutations is in the NS1 gene and is responsible for the diminished ability of the NS1 gene product to antagonize a cellular interferon response, and permits the attenuated virus, at a MOI of between 0.0005 and 0.001, 0.001 and 0.01, 0.01 and 0.1, or 0.1 and 1, or a MOI of 0.0005, 0.0007, 0.001, 0.005, 0.01, 0.05, 0.1, 0.5, 1.0, 1.5, 2.0, 2.5, 3.0, 3.5, 4.0, 4.5, 5.0, 5.5, or 6.0, to grow to titers between approximately 1 to approximately 100 fold, approximately 5 to approximately 80 fold, approximately 20 to approximately 80 fold, or approximately 40 to approximately 80 fold, approximately 1 to approximately 10 fold, approximately 1 to approximately 5 fold, approximately 1 to approximately 4 fold, approximately 1 to approximately 3 fold, approximately 1 to approximately 2 fold, approximately 3 to approximately 15 fold or approximately 1, 2, 3, 4, 5, 6, 7, 8, 10, 15, 20, 25, 30, 35, 40, 45, 50, 55, 60, 65, 70, 75, 80, 85, 90, 95 or 100 fold lower than wild-type swine influenza virus in cells (e.g., cells of a human (e.g., PerC6, a producer cell line derived from human embryonic retinoblasts transformed with the E1 region of Adenovirus 5), mouse, chicken (e.g., chicken embryo fibroblasts), rat, birds, or pig (e.g., PK(D1) cells, PK(15) cells, PK13 cells, NSK cells, LLC-PK1 cells, LLC-PK1A cells, ESK-4 cells, ST cells, PT-K75 cells, PK-2a/CL 13 or SJPL cells)), as determined by, e.g., hemagglutination assays, approximately 2 to 10 days, 3 to 7 days, 3 to 5 days, or 2, 3, 5, 6, 7, 8, 9, 10 days post-infection when the viruses are propagated under the same conditions.

In a specific embodiment, an attenuated swine influenza virus of the invention comprises a genome comprising at least two, at least three, at least four or more mutations in two, three, four or more swine influenza virus genes, wherein at least one of the mutations is in the NS1 gene and is responsible for the diminished ability of the NS1 gene product to antagonize a cellular interferon response, and permits the attenuated virus, at a MOI of between 0.0005 and 0.001, 0.001 and 0.01, 0.01 and 0.1, or 0.1 and 1, or a MOI of 0.0005, 0.0007, 0.001, 0.005, 0.01, 0.05, 0.1, 0.5, 1.0, 1.5, 2.0, 2.5, 3.0, 3.5, 4.0, 4.5, 5.0, 5.5, or 6.0, to grow to titers between approximately 1 to approximately 100 fold, approximately 5 to approximately 80 fold, approximately 20 to approximately 80 fold, or approximately 40 to approximately 80 fold, approximately 1 to approximately 10 fold, approximately 1 to approximately 5 fold, approximately 1 to approximately 4 fold, approximately 1 to approximately 3 fold, approximately 1 to approximately 2 fold, approximately 3 to approximately 15 fold or approximately 1, 2, 3, 4, 5, 6, 7, 8, 10, 15, 20, 25, 30, 35, 40, 45, 50, 55, 60, 65, 70, 75, 80, 85, 90, 95 or 100 fold lower than wild-type swine influenza virus in pig cells, as determined by, e.g., hemagglutination assays, approximately 2 to 10 days, 3 to 7 days, 3 to 5 days, or 2, 3, 5, 6, 7, 8, 9, 10 days post-infection when the viruses are propagated under the same conditions (e.g., in MDCK cells). In another embodiment, an attenuated swine influenza virus of the invention comprises a genome comprising at least two, three, four or more mutations in two, three, four or more swine influenza virus genes, wherein at least one of the mutations is in the NS1 gene and is responsible for the attenuation of the virus, and permits the attenuated virus, at a MOI of between 0.0005 and 0.001, 0.001 and 0.01, 0.01 and 0.1, or 0.1 and 1, or a MOI of 0.0005, 0.0007, 0.001, 0.005, 0.01, 0.05, 0.1, 0.5, 1.0, 1.5, 2.0, 2.5, 3.0, 3.5, 4.0, 4.5, 5.0, 5.5, or 6.0, to grow to titers between approximately 1 to approximately 100 fold, approximately 5 to approximately 80 fold, approximately 20 to approximately 80 fold, or approximately 40 to approximately 80 fold, approximately 1 to approximately 10 fold, approximately 1 to approximately 5 fold, approximately 1 to approximately 4 fold, approximately 1 to approximately 3 fold, approximately 1 to approximately 2 fold, approximately 3 to approximately 15 fold or approximately 1, 2, 3, 4, 5, 6, 7, 8, 10, 15, 20, 25, 30, 35, 40, 45, 50, 55, 60, 65, 70, 75, 80, 85, 90, 95 or 100 fold lower than wild-type swine influenza virus in pig cells, as determined by, e.g., hemagglutination assays, approximately 2 to 10 days, 3 to 7 days, 3 to 5 days, or 2, 3, 5, 6, 7, 8, 9, 10 days post-infection when the viruses are propagated under the same conditions (e.g., in MDCK cells). In accordance with these embodiments, the attenuated virus has an impaired interferon antagonist phenotype and may be genetically engineered to contain or express non-swine influenza virus nucleic acid sequences, such as, e.g., an epitope of a foreign pathogen (e.g., epitopes of porcine reproductive and respiratory syndrome virus, porcine cytomegalo virus, porcine respiratory corona virus, porcine encephalomyocarditis virus, porcine epidemic diarrhea and antigenic determinants of non-viral swine pathogens such as bacteria, including, but not limited to, *Brucella suis*, and parasites, including, but not limited to, roundworms (*Ascaris suum*), whipworms (*Trichuris suis*), or a tumor antigen such as carcinoembryonic antigen (CEA), breast cancer antigen such as EGFR (epidermal growth factor receptor), HER2 antigen (p185$^{HER2}$), HER2 neu epitope, cancer antigen-50 (CA-50), cancer antigen 15-3 (CA15-3) associated with breast cancer, carcinoma associated antigen (CAA), melanoma antigen, and melanoma associated antigens 100, 25, and 150). Preferably, the non-swine influenza virus sequences (heterologous sequences) do not include a nucleic acid sequence that alters the attenuated phenotype of the virus. Accordingly, nucleic acid sequences encoding proteins, polypeptides or peptides with interferon antagonizing activity are preferably not engineered into the swine influenza virus.

Mutations in the swine influenza virus NS1 gene comprise (alternatively, consist of) any mutation that results in the desired phenotype (i.e., an impaired ability to antagonize a cellular interferon response). Examples of the type of mutations that can be included in or introduced into a swine influenza virus NS1 gene include, but are not limited to, deletions, substitutions, insertions and combinations thereof. One or more mutations can be located anywhere throughout the NS1 gene, i.e., in the regulatory, non-coding and/or coding regions (e.g., the amino-terminus and/or the carboxy-terminus or somewhere in between). In a specific embodiment, an attenuated swine influenza virus of the invention comprises a genome comprising a swine influenza virus NS1 gene with a mutation (e.g., a deletion or substitution) at the amino terminus. In a preferred embodiment, an attenuated swine influenza virus of the invention comprises a genome comprising a swine influenza NS1 gene with a mutation (e.g., a deletion or substitution, preferably a deletion) at the carboxy terminus. In another embodiment, an attenuated swine influenza virus of the invention comprises a genome comprising a mutation in a swine influenza virus NS1 gene resulting in a deletion consisting of 5, preferably 10, 15, 20, 25, 30, 35, 40, 45, 50, 55, 60, 65, 70, 75, 80, 85, 90, 91, 92, 93, 94, 95, 100, 105, 110, 115, 119, 120, 121, 125, 130, 135, 140, 145, 146, 147, 148, 150, 155, 160, 165, 170 or 175 amino acid residues from the carboxy terminus of NS1, or a deletion of between 5-170, 25-170, 50-170, 100-170, 90-160, 100-160 or 105-160, 90-150, 5-75, 5-50 or 5-25 amino acid residues from the carboxy terminus. In another embodiment, an attenuated swine influenza virus of the invention comprises a genome comprising a mutation in a swine influenza virus NS1 gene resulting in a deletion of all amino acid residues of the NS1 gene product except amino acid residues 1-126, amino acid residues 1-120, amino acid residues 1-115, amino acid residues 1-110, amino acid residues 1-100, amino acid residues 1-99, amino acid residues 1-95, amino acid residues 1-85, amino acid residues 1-80, amino acid residues 1-75, amino acid residues 1-73, amino acid residues 1-70, amino acid residues 1-65 or amino acid residues 1-60, wherein the amino terminal amino acid is number 1. In accordance with these embodiments, the attenuated swine influenza virus is preferably genetically engineered. In a preferred embodiment, an attenuated swine influenza virus of the invention is TX/98/del 126, TX/98/del 99 or TX/98/del 73.

The attenuated swine influenza virus of the present invention may be a chimeric virus that expresses a heterologous sequence. Preferably, the heterologous sequence is not a nucleic acid sequence that alters the attenuated phenotype of the virus. Accordingly, preferably, nucleic acid sequences encoding proteins, polypeptides or peptides with interferon antagonizing activity are not engineered into the swine influenza virus. In certain embodiments, the chimeric virus expresses a tumor antigen. In other embodiments, the chimeric virus expresses an epitope of a foreign pathogen.

An attenuated swine influenza virus having the desired phenotype can itself be used as the active ingredient in vaccine, pharmaceutical or immunogenic formulations. Alternatively, the attenuated swine influenza virus can be used as the vector or "backbone" of recombinantly produced vaccines or immunogenic formulations. To this end, the "reverse genetics" technique or helper-free plasmid approach can be used to engineer mutations or introduce foreign epitopes into the attenuated swine influenza virus, which would serve as the "parental" strain. In this way, vaccines can be designed for immunization against strain variants, or in the alternative, against completely different infectious agents or disease antigens (e.g., tumor antigens). For example, the attenuated swine influenza virus can be engineered to express neutralizing epitopes of other preselected strains. Alternatively, epitopes of other viruses can be built into the attenuated swine influenza virus. Alternatively, epitopes of non-viral infectious pathogens (e.g., parasites, bacteria, fungi) can be engineered into the swine influenza virus.

In a particular embodiment, reassortment techniques can be used to transfer the attenuated phenotype from a parental swine influenza virus strain (a natural mutant, a mutagenized virus, or a genetically engineered virus) to a different virus strain (a wild-type virus, a natural mutant, a mutagenized virus, or a genetically engineered virus). In accordance with this embodiment, the "reverse genetics technique" or helper-free plasmid approach can be used to engineer mutations or introduce foreign epitopes into the attenuated swine influenza virus, which would serve as the "parental strain".

The present invention provides methods for vaccinating subjects comprising administering a vaccine formulation comprising an attenuated swine influenza virus comprising a mutation in a swine influenza NS1 gene that diminishes the ability of the NS1 gene product to antagonize the cellular interferon response, and a physiologically effective excipient. In one embodiment, the present invention provides a method comprising administering an effective amount of a vaccine formulation of the invention. In certain embodiments, the dose of the vaccine formulation administered is between about $10^2$ to about $10^8$, about $10^3$ to about $10^7$, or about $10^4$ to about $5 \times 10^6$ pfu. In other embodiments, the dose of the vaccine formulation administered is $10^2$, $5 \times 10^2$, $10^3$, $5 \times 10^3$, $10^4$, $5 \times 10^4$, $10^5$, $5 \times 10^5$, $10^6$, $5 \times 10^6$, $10^7$, $5 \times 10^7$ or $10^8$ pfu. In specific embodiments, the subject is a donkey, zebra, camel, dog, avian (e.g., a duck). In a preferred embodiment, the subject is a pig.

The present invention provides immunogenic formulations comprising an attenuated swine influenza virus of the invention and methods for inducing an immune response for the treatment, management or prevention of a swine influenza virus infection or a condition or symptom associated therewith, an infection, other than a swine influenza virus infection, or a condition or symptom associated therewith, or a condition in which the attenuated swine influenza viruses can be used as a vector to induce an immune response to a particular antigen associated with the condition, comprising administering to a subject an immunogenic formulation of the invention. In one embodiment, the present invention provides a method for inducing an immune response for the treatment, management or prevention of a swine influenza virus infection or a condition or symptom associated therewith, an infection, other than a swine influenza virus infection, or a condition or symptom associated therewith, or a condition in which the attenuated swine influenza viruses can be used as a vector to induce an immune response to a particular antigen associated with the condition, comprising administering to a subject an effective amount of an immunogenic formulation of the invention. In certain embodiments, the dose of an immunogenic formulation of the invention administered to a subject is between about $10^2$ to about $10^8$, about $10^3$ to about $10^7$, or about $10^4$ to about $5 \times 10^6$ pfu or about $10^4$ to about $10^7$ pfu. In specific embodiments, the immunogenic formulation administered to a subject has an attenuated swine influenza virus concentration of about $10^4$ to about $10^7$ pfu/ml. In other embodiments, the dose of an immunogenic formulation of the invention administered to a subject is $10^2$, $5 \times 10^2$, $10^3$, $5 \times 10^3$, $10^4$, $5 \times 10^4$, $10^5$, $5 \times 10^5$, $10^6$, $5 \times 10^6$, $10^7$, $5 \times 10^7$ or $10^8$ pfu. In specific embodiments, the subject is a donkey, zebra, camel, dog, avian (e.g., a duck). In a preferred embodiment, the subject is a pig.

The attenuated swine influenza viruses, which induce robust IFN responses in subjects, may also be used in pharmaceutical formulations for the prophylaxis or treatment of infections and IFN-treatable diseases such as cancer. In this regard, the tropism of the attenuated swine influenza virus can be altered to target the virus to a desired target organ, tissue or cells in vivo or ex vivo. Using this approach, the IFN response can be induced locally, at the target site, thus avoiding or minimizing the side effects of systemic IFN therapy. To this end, the attenuated swine influenza virus can be engineered to express a ligand specific for a receptor of the target organ, tissue or cells.

The present invention provides methods for preventing, managing or treating an infection, or IFN-treatable disease in a subject (e.g., a pig), other than a swine influenza viral infection, or IFN-treatable disease caused by swine influenza virus, comprising administering a pharmaceutical formulation of the invention. In one embodiment, the present invention provides a method for preventing, managing or treating an infection or IFN-treatable disease in a subject, other than a swine influenza viral infection or IFN-treatable disease caused by swine influenza virus, comprising administering to a subject an effective amount of a pharmaceutical formulation of the invention. In certain embodiments, the dose of the pharmaceutical formulation administered to the subject is between about $10^2$ to about $10^{12}$, about $10^2$ to about $10^{10}$, about $10^2$ to about $10^8$, about $10^3$ to about $10^9$, about $10^3$ to about $10^7$, about $10^4$ to about $10^8$, about $10^4$ to about $5 \times 10^6$, about $10^4$ to about $10^7$, or about $10^4$ to about $10^{12}$ pfu. In specific embodiments, the pharmaceutical formulation administered to the subject has an attenuated influenza virus concentration from about $10^4$ to about $10^{12}$ pfu/ml. In other embodiments, the dose of the pharmaceutical formulation administered is $10^2$, $5 \times 10^2$, $10^3$, $5 \times 10^3$, $10^4$, $5 \times 10^4$, $10^5$, $5 \times 10^5$, $10^6$, $5 \times 10^6$, $10^7$, $5 \times 10^7$, $10^8$, $5 \times 10^8$, $1 \times 10^9$, $5 \times 10^9$, $1 \times 10^{10}$, $5 \times 10^{10}$, $1 \times 10^{11}$, $5 \times 10^{11}$ or $10^{12}$ pfu. In specific embodiments, the subject is a donkey, zebra, camel, dog, avian (e.g., a duck). In a preferred embodiment, the subject is a pig.

The present invention provides methods for preventing, managing or treating cancer in a subject comprising administering a pharmaceutical formulation of the invention. In one embodiment, the present invention provides a method for preventing, managing or treating cancer in a subject comprising administering to a subject an effective amount of a pharmaceutical formulation of the invention. In certain embodiments, the pharmaceutical formulation comprises a swine influenza virus comprising a tumor antigen. In certain embodiments, the dose of the pharmaceutical formulation administered to the subject is between about $10^2$ to about $10^{12}$, about $10^2$ to about $10^{10}$, about $10^2$ to about $10^8$, about $10^3$ to about $10^9$, about $10^3$ to about $10^7$, about $10^4$ to about $10^8$, about $10^4$ to about $5 \times 10^6$ pfu or about $10^4$ to about $10^{12}$ pfu. In other embodiments, the dose of the pharmaceutical formulation administered is $10^2$ $5 \times 10^2$ $10^3$ $5 \times 10^3$ $10^4$ $5 \times 10^4$ $10^5$ $5 \times 10^5$ $10^6$ $5 \times 10^6$ $10^7$ $5 \times 10^7$ $10^8$ $5 \times 10^8$ $1 \times 10^9$, $5 \times 10^9$, $1 \times 10^{10}$, $5 \times 10^{10}$, $1 \times 10^{11}$, $5 \times 10^{11}$ or $10^{12}$ pfu. In specific embodiments, the subject is a donkey, zebra, camel, dog, avian (e.g., a duck). In a preferred embodiment, the subject is a pig.

Applicants have demonstrated that attenuated swine influenza viruses with impaired interferon antagonist activity replicate in vivo generating titers that are lower than detected with wild-type swine influenza viruses, but that are sufficient to induce immunological and cytokine responses. Thus, mutations which diminish but do not abolish the IFN antagonist activity of the swine influenza virus are preferred for vaccine, immunologic, and pharmaceutical formulations. Such viruses can be selected for growth in both conventional and non-conventional substrates, and for intermediate virulence.

The present invention provides cells containing (alternatively, comprising) swine influenza viruses of the present invention. In a specific embodiment, a cell contains/comprises a swine influenza virus that is genetically engineered. In certain embodiments, the attenuated swine influenza virus contained in the cell is engineered to encode an epitope derived from another pathogen (e.g., another virus) or a tumor antigen. In accordance with this embodiment, the genome of the attenuated swine influenza virus may comprise at least one segment derived from a different virus. Any cell can be infected with, contain or comprise an attenuated swine influenza virus of the invention including, but not limited to, MDCK cells, PK cells, Vero cells, primary human umbilical vein endothelial cells (HUVEC), H292 human epithelial cell line, HeLa cells, and swine embryonic kidney cells RES. In a preferred embodiment, the cell is a pig cell or a pig cell line. In certain embodiments, the cell (e.g., a pig cell or pig cell line) is interferon deficient.

In certain other embodiments, the swine influenza viruses of the invention are contained in 10 day-old, 6 to 9 day-old, 6 to 8 day-old, or 6 to 7 day-old embryonated chicken eggs. In a specific embodiment, the viruses are contained in allantoic cavity of such eggs. In another specific embodiment, the viruses are contained in the amniotic cavity of such eggs.

The invention encompasses the use of substrates such as cells, cell lines and embryonated eggs, to propagate the attenuated swine influenza viruses of the invention. In one embodiment, the invention provides methods for vaccine production and pharmaceutical production comprising propagating in a substrate an attenuated swine influenza virus of the present invention and collecting progeny virus, wherein the substrate is a cell, cell line or embryonated egg. In certain embodiments, the substrate is an IFN deficient system. Exemplary IFN-deficient systems include, but are not limited to, young embryonated eggs (e.g., 6 to 10 days old, 6 to 9 days old, 6 to 8 days old or 6 to 7 days old embryonated eggs), and IFN-deficient cell lines (such as VERO cells or genetically engineered cell lines such as STAT1 knockouts). Embryonated eggs or cell lines pretreated with compounds that inhibit the IFN system (including drugs, antibodies, antisense, ribozymes, etc.) can also be used as an IFN-deficient system. Further, eggs deficient in the IFN system, e.g., eggs produced by STAT1 negative birds, especially fowl, including but not limited to transgenic chickens, ducks or turkeys, may be used as an IFN-deficient system.

3.1 Terminology

As used herein, the term "about" or "approximately" when used in conjunction with a number refers to any number within 1, 5 or 10% of the referenced number.

As used herein, the phrase "amino-terminus" of NS1 refer to the amino acids from the amino terminal amino acid residue (amino acid residue 1) through amino acid residue 115, amino acid residues 1 through 100, amino acid residues 1 through 75, amino acid residues 1 through 50, amino acid residues 1 through 25, or amino acid residues 1 through 10 of the swine influenza viral NS1 protein.

As used herein, the phrase "carboxy-terminus" of NS1 refer to amino acid residues 116 through the carboxy terminal amino acid residue, amino acid residues 101 through the carboxy terminal amino acid residue, amino acid residues 76 through the carboxy terminal amino acid residue, amino acid residues 51 through the carboxy terminal amino acid residue, or amino acid residues 26 through the carboxy terminal amino acid residue of the swine influenza viral NS1 protein, when the amino-terminus of NS1 is amino acid residues 1 through amino acid residue 115, amino acid residues 1 through 100, amino acid residues 1 through 75, amino acid residues 1 through 50, or amino acid residues 1 through 25, respectively, of the swine influenza viral NS1 protein. Deletions from the carboxy terminus can include deletions consisting of 5, preferably 10, 15, 20, 25, 30, 35, 40, 45, 50, 55, 60, 65, 70, 73, 75, 80, 85, 90, 95, 99, 100, 105, 110, 115, 120, 125, 126, 130, 135, 140, 145, 150, 155, 160, 165, 170 or 175 amino acid residues from the carboxy terminus of NS1.

As used herein, the term "cytokine receptor modulator" refers to an agent which modulates the phosphorylation of a cytokine receptor, the activation of a signal transduction pathway associated with a cytokine receptor, and/or the expression of a particular protein such as a cytokine. Such an agent may directly or indirectly modulate the phosphorylation of a cytokine receptor, the activation of a signal transduction pathway associated with a cytokine receptor, and/or the expression of a particular protein such as a cytokine. Thus, examples of cytokine receptor modulators include, but are not limited to, cytokines, fragments of cytokines, fusion proteins, and antibodies that immunospecifically binds to a cytokine receptor or a fragment thereof. Further, examples of cytokine receptor modulators include, but are not limited to, peptides, polypeptides (e.g., soluble cytokine receptors), fusion proteins and antibodies that immunospecifically binds to a cytokine or a fragment thereof.

As used herein, the term "effective amount" refers to the amount of a therapy (e.g., a prophylactic or therapeutic agent) which is sufficient to reduce and/or ameliorate the severity and/or duration of a condition (e.g., a swine influenza virus infection or a condition or symptom associated therewith, another infection (e.g., another viral infection), an IFN treatable disease or a condition in which the attenuated swine influenza viruses can be used as a vector to induce an immune response to a particular antigen associated with the condition), prevent the advancement of a condition (e.g., a swine influenza virus infection or a condition or symptom associated therewith, another infection (e.g., another viral infection), an IFN treatable disease or a condition in which the attenuated swine influenza viruses can be used as a vector to induce an immune response to a particular antigen associated with the condition), cause regression of a condition (e.g., a swine influenza virus infection or a condition or symptom associated therewith, another infection (e.g., another viral infection) or an IFN treatable disease), prevent the recurrence, development, or onset of one or more symptoms associated with a condition (e.g., a swine influenza virus infection or a condition or symptom associated therewith, another infection (e.g., another viral infection) or an IFN treatable disease), reduce the titer of swine influenza virus or enhance or improve the prophylactic or therapeutic effect(s) of another therapy (e.g., prophylactic or therapeutic agent).

As used herein, the term "epitopes" refers to sites or fragments of a polypeptide or protein having antigenic or immunogenic activity in an animal, preferably in a mammal, and most preferably in a pig. An epitope having immunogenic activity is a site or fragment of a polypeptide or protein that elicits an antibody response in an animal. An epitope having antigenic activity is a site or fragment of a polypeptide or protein to which an antibody immunospecifically binds as determined by any method well-known to one of skill in the art, for example by immunoassays.

As used herein, the term "fragment" in the context of a proteinaceous agent refers to a peptide or polypeptide comprising an amino acid sequence of at least 2 contiguous amino acid residues, at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, at least 200 contiguous amino acid residues, or at least 250 contiguous amino acid residues of the amino acid sequence of a peptide, polypeptide or protein. In one embodiment, a fragment of a full-length protein retains activity of the full-length protein, e.g., IFN antagonist activity. In another embodiment, the fragment of the full-length protein does not retain the activity of the full-length protein, e.g., IFN antagonist activity.

As used herein, the term "fragment" in the context of a nucleic acid refers to a nucleic acid comprising an nucleic acid sequence of at least 2 contiguous nucleotides, at least 5 contiguous nucleotides, at least 10 contiguous nucleotides, at least 15 contiguous nucleotides, at least 20 contiguous nucleotides, at least 25 contiguous nucleotides, at least 30 contiguous nucleotides, at least 35 contiguous nucleotides, at least 40 contiguous nucleotides, at least 50 contiguous nucleotides, at least 60 contiguous nucleotides, at least 70 contiguous nucleotides, at least contiguous 80 nucleotides, at least 90 contiguous nucleotides, at least 100 contiguous nucleotides, at least 125 contiguous nucleotides, at least 150 contiguous nucleotides, at least 175 contiguous nucleotides, at least 200 contiguous nucleotides, at least 250 contiguous nucleotides, at least 300 contiguous nucleotides, at least 350 contiguous nucleotides, or at least 380 contiguous nucleotides of the nucleic acid sequence encoding a peptide, polypeptide or protein. In a preferred embodiment, a fragment of a nucleic acid encodes a peptide or polypeptide that retains activity of the full-length protein, e.g., IFN antagonist activity. In another embodiment, the fragment of the full-length protein does not retain the activity of the full-length protein, e.g., IFN antagonist activity.

As used herein, the phrase "heterologous sequence" refers to any sequence nucleic acid or protein, polypeptide or peptide sequence which is not normally found or in nature associated in nature with a nucleic acid or protein, polypeptide or peptide sequence of interest. For example, a "heterologous sequence" may refer to a sequence derived from a different species.

As used herein, the term "in combination" refers to the use of more than one therapy (e.g., more than one prophylactic agent and/or therapeutic agent). The use of the term "in combination" does not restrict the order in which therapies (e.g., prophylactic and/or therapeutic agents) are administered to a subject with a condition (e.g., a swine influenza virus infection or a condition or symptom associated therewith, another infection (e.g., another viral infection) or an IFN treatable disease). A first therapy (e.g., a first prophylactic or therapeutic agent) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a second prophylactic or therapeutic agent) to a subject with a condition (e.g., a swine influenza virus infection or a condition or symptom associated therewith, another infection (e.g., another viral infection) or an IFN treatable disease).

As used herein, the phrase "interferon antagonist activity" refers to a protein or polypeptide, or fragment, derivative, or analog thereof that reduces or inhibits the cellular interferon immune response. In particular, a protein or polypeptide, or fragment, derivative, or analog thereof (e.g., swine influenza virus NS1) that has interferon antagonist activity reduces or inhibits interferon expression and/or activity. In a specific embodiment, the phrase "interferon antagonist activity" refers to a swine influenza virus protein or polypeptide, or fragment, derivative, or analog thereof that reduces or inhibits the cellular interferon immune response. A swine influenza viral protein or polypeptide with interferon antagonist activity may preferentially affect the expression and/or activity of one or two types of interferon (IFN). In one embodiment, the expression and/or activity of IFN-α is affected. In another embodiment, the expression and/or activity of IFN-β is affected. In one embodiment, the expression and/or activity of IFN-γ is affected. In certain embodiments, the expression and/or activity of IFN-β☐ and/or IFN-γ is reduced 5-10%, 10-20%, 20-30%, 30-40%, 40-50%, 50-60%, 60-70%, 70-80%, 80-90% or more by protein, polypeptide, etc. with an interferon antagonist activity when compared to a control (e.g., PBS or a protein without interferon antagonist activity) in IFN-competent systems, e.g., a wild-type cell or animal under the same conditions. In certain embodiments, the expression and/or activity of IFN-β and/or IFN-γ is reduced approximately 1 to approximately 100 fold, approximately 5 to approximately 80 fold, approximately 20 to approximately 80 fold, approximately 1 to approximately 10 fold, or approximately 1 to approximately 5 fold, or approximately 40 to approximately 80 fold, or 1, 2, 3, 4, 5, 7, 10, 15, 20, 25, 30, 35, 40, 45, 50, 55, 60, 65, 70, 75, 80, 85, 90, 95 or 100 fold by protein, polypeptide, etc. with an interferon antagonist activity when compared to a control (e.g., PBS or a protein without interferon antagonist activity) in IFN-competent systems under the same conditions.

As used herein, the phrases "IFN-deficient systems" or "IFN-deficient substrates" refer to systems, e.g., cells, cell lines and animals, such as pigs, mice, chickens, turkeys, rabbits, rats, etc., which do not produce IFN or produce low levels of IFN (i.e., a reduction in IFN expression of 5-10%, 10-20%, 20-30%, 30-40%, 40-50%, 50-60%, 60-70%, 70-80%, 80-90% or more when compared to IFN-competent systems under the same conditions), do not respond or respond less efficiently to IFN, and/or are deficient in the activity of one or more antiviral genes induced by IFN.

As used herein, the phrase "IFN-inducing phenotype" refers to a phenotype whereby a virus demonstrates an increased cellular interferon response compared to a wild-type virus, which typically inhibits or reduces cellular interferon mediated As used herein, the phrases "IFN treatable disorders", "IFN treatable diseases" and analogous phrases refer to conditions that are preventable, treatable, managed or ameliorated by the administration of IFN, either IFN-α, β, γ or any combination thereof. The IFN treatable disorders need not be limited to swine, if swine influenza virus infects other species. Examples of IFN treatable disorders in pigs include, but are not limited to, foot and mouth disease, porcine *Haemophilus* pneumonia (PHP, and other disorders caused by infection with, e.g., infection by *A. pleuropneumonias, P. haemolytica, P. multocida, H. somnus* and *A. suis.*

As used herein, the phrase "intermediate" phenotype with respect to IFN-antagonist activity refers to a phenotype which can stimulate a robust immune response, while being attenuated because viruses with an intermediate phenotype cannot overcome the host IFN response. In particular, an intermediate phenotype can stimulate an immune response and inhibit/reduce IFN only to the extent that it allows fewer rounds of virus replication or lower numbers of virus particles being produced compared to wild-type virus, as determined by techniques well-known in the art (e.g., as measured by lower plaque titer or hemagglutination assays).

As used herein, the term "isolated", in the context of viruses, refers to a virus that is derived from a single parental virus. A virus can be isolated using routine methods known to one of skill in the art including, but not limited to, those based on plaque purification and limiting dilution.

As used herein, the terms "manage," "managing," and "management" refer to the beneficial effects that a subject derives from a therapy (e.g., a prophylactic or therapeutic agent), which does not result in a cure of the disease. In certain embodiments, a subject is administered one or more therapies (e.g., one or more prophylactic or therapeutic agents) to "manage" a disease so as to prevent the progression or worsening of the disease.

As used herein, the phrase "multiplicity of infection" or "MOI" is the average number of virus per infected cell. The MOI is determined by dividing the number of virus added (ml added×PFU) by the number of cells added (ml added× cells/ml).

As used herein, the phrase "non-swine influenza virus" in the context of swine influenza viruses containing or comprising non-swine influenza virus sequences refers to any influenza virus strain or isolate comprising a sequence (e.g., a nucleic acid or amino acid sequence) heterologous to swine influenza virus, i.e, the sequence is not found to naturally in association with swine influenza virus.

As used herein, the phrase "NS1 gene" refers to the gene which encodes the nonstructural protein (NS1) in influenza. NS1 is one of the eight molecules encoded by the segmented genome of influenza A and other viruses. A "swine influenza virus NS1 gene" is an NS1 gene isolated from a swine influenza virus. Representative swine NS1 genes can be found in public sequence databases such as Genbank and include, but are not limited to, Genbank Accession No. AJ293939 (A/swine/Italy/13962/95(H3N2)) and Genbank Accession No. AJ344041 (A/swine/Cotes d'Armor/1121/00 (H1N1)). A "NS1 gene product" refers to a gene product (e.g., a RNA or protein) encoded by a NS1 gene. In the case of a protein, the NS1 gene product is full-length and has wild-type NS1 activity, (e.g., from Influenza A/swine/Texas/4199-2/98. A "swine influenza virus NS1 gene product" refers to a gene product (e.g., a RNA or protein) encoded by a swine influenza virus NS1 gene. In the case of a protein, the swine influenza virus NS1 gene product is full-length and has wild-type swine influenza virus NS1 activity, e.g., from Influenza A/swine/Texas/4199-2/98.

As used herein, the terms "prevent", "preventing" and "prevention" refer to the inhibition of the development or onset of a condition (e.g, a swine influenza virus infection or a condition associated therewith, an infection other than a swine influenza virus infection or a condition associated therewith, an IFN-treatable disease or a condition in which the attenuated swine influenza viruses can be used as a vector to induce an immune response to a particular antigen associated with the condition), or the prevention of the recurrence, onset, or development of one or more symptoms of a condition (e.g., a swine influenza virus infection or a condition associated therewith, an infection other than a swine influenza virus infection or a condition associated therewith, or an IFN-treatable disease), in a subject resulting from the administration of a therapy (e.g., a prophylactic or therapeutic agent), or the administration of a combination of therapies (e.g., a combination of prophylactic or therapeutic agents).

As used herein, the terms "prophylactic agent" and "prophylactic agents" refer to any agent(s) which can be used in the prevention of a condition or a symptom thereof (e.g., a swine influenza virus infection or a condition or symptom associated therewith, an infection other than a swine influenza virus infection or a condition or symptom associated therewith, an IFN treatable disease or a condition in which the attenuated swine influenza viruses can be used as a vector to induce an immune response to a particular antigen associated with the condition). Preferably, a prophylactic agent is an agent which is known to be useful to or has been or is currently being used to the prevent or impede the onset, development, progression and/or severity of a swine influenza virus infection or a condition or symptom associated therewith, an infection other than a swine influenza virus infection or a condition or symptom associated therewith, an IFN treatable disease or a condition in which the attenuated swine influenza viruses can be used as a vector to induce an immune response to a particular antigen associated with the condition.

As used herein, the term "prophylactically effective amount" refers to the amount of a therapy (e.g., prophylactic agent) which is sufficient to result in the prevention of the development, recurrence, or onset of a condition or a symptom thereof (e.g., a swine influenza virus infection or a condition or symptom associated therewith, an infection other than a swine influenza virus infection or a condition or symptom associated therewith, an IFN treatable disease or a condition in which the attenuated swine influenza viruses can be used as a vector to induce an immune response to a particular antigen associated with the condition) or to enhance or improve the prophylactic effect(s) of another therapy (e.g., a prophylactic agent).

As used herein, the phrase "purified" in the context of viruses refers to a virus which is substantially free of cellular material and culture media from the cell or tissue source from which the virus is derived. The language "substantially free of cellular material" includes preparations of virus in which the virus is separated from cellular components of the cells from which it is isolated or recombinantly produced. Thus, virus that is substantially free of cellular material includes preparations of protein having less than about 30%, 20%, 10%, or 5% (by dry weight) of cellular protein (also referred to herein as a "contaminating protein"). The virus is also substantially free of culture medium, i.e., culture medium represents less than about 20%, 10%, or 5% of the volume of the virus preparation. A virus can be purified using routine methods known to one of skill in the art including, but not limited to, chromatography and centrifugation.

As used herein, the terms "subject" or "patient" are used interchangeably. As used herein, the terms "subject" and "subjects" refers to an animal (e.g., birds, reptiles, and mammals), preferably a mammal including a non-primate (e.g., a camel, donkey, zebra, cow, pig, horse, cat, dog, rat, and mouse) and a primate (e.g., a monkey, chimpanzee, and a human). In certain embodiments, the subject or patient has a swine influenza virus infection. In certain embodiments, the mammal is 0 to 6 months old, 6 to 12 months old, 1 to 5 years old, 5 to 10 years old, 10 to 15 years old, 15 to 20 years old, 20 to 25 years old, 25 to 30 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100. In a preferred embodiment, the subject or patient is a pig. In certain embodiments, the pig is 0 to 6 months old, 6 to 12 months old, 1 to 5 years old, 5 to 10 years old or 10 to 15 years old. The natural lifespan of a pig is 10-15 years.

As used herein, "swine influenza virus" refers to a type A or type C influenza virus from the family orthomyxovirus that causes swine influenza. While orthomyxovirus has three groups: type A, type B and type C, only type A and type C influenza viruses infect pigs. Subtypes of swine influenza virus include H1N1, H1N2, H3N2, and H3N1. H9N2 and H5N1 can also be found in pigs. In certain embodiments, a swine influenza virus is an influenza virus that has been isolated from swine. In a preferred embodiment, a swine influenza virus contains a swine NS1 gene. Representative swine NS1 genes can be found in public sequence databases such as Genbank and include, but are not limited to, Genbank Accession No. AJ293939 (A/swine/Italy/13962/95 (H3N2)) and Genbank Accession No. AJ344041 (A/swine/Cotes d'Armor/1121/00(H1N1)). Examples of swine influenza virus variants include, but are not limited to, A/Swine/Colorado/1/77, A/Swine/Colorado/23619/99, A/Swine/Cote d'Armor/3633/84, A/Swine/Cote d'Armor/3633/84, A/Swine/England/195852/92, A/Swine/Finistere/2899/82, A/Swine/Hong Kong/10/98, A/Swine/Hong Kong/9/98, A/Swine/Hong Kong/81/78, A/Swine/Illinois/100084/01, A/Swine/Illinois/100085A/01, A/Swine/Illinois/21587/99, A/Swine/Indiana/1726/88, A/Swine/Indiana/9K035/99, A/Swine/Indiana/P12439/00, A/Swine/Iowa/30, A/Swine/Iowa/15/30, A/Swine/Iowa/533/99, A/Swine/Iowa/569/99, A/Swine/Iowa/3421/90, A/Swine/Iowa/8548-1/98, A/Swine/Iowa/930/01, A/Swine/Iowa/17672/88, A/Swine/Italy/1513-1/98, A/Swine/Italy/1523/98, A/Swine/Korea/CY02/02, A/Swine/Minnesota/55551/00, A/Swine/Minnesota/593/99, A/Swine/Minnesota/9088-2/98, A/Swine/Nebraska/1/92, A/Swine/Nebraska/209/98, A/Swine/Netherlands/12/85, A/Swine/North Carolina/16497/99, A/Swine/North Carolina/35922/98, A/Swine/North Carolina/93523/01, A/Swine/North Carolina/98225/01, A/Swine/Oedenrode/7C/96, A/Swine/Ohio/891/01, A/Swine/Oklahoma/18717/99, A/Swine/Oklahoma/18089/99, A/Swine/Ontario/01911-1/99, A/Swine/Ontario/01911-2/99, A/Swine/Ontario/41848/97, A/Swine/Ontario/97, A/Swine/Quebec/192/81, A/Swine/Quebec/192/91, A/Swine/Quebec/5393/91, A/Swine/Taiwan/7310/70, A/Swine/Tennessee/24/77, A/Swine/Texas/4199-2/98, A/Swine/Wisconsin/125/97, A/Swine/Wisconsin/136/97, A/Swine/Wisconsin/163/97, A/Swine/Wisconsin/164/97, A/Swine/Wisconsin/166/97, A/Swine/Wisconsin/168/97, A/Swine/Wisconsin/235/97, A/Swine/Wisconsin/238/97, A/Swine/Wisconsin/457/98, A/Swine/Wisconsin/458/98, A/Swine/Wisconsin/464/98 and A/Swine/Wisconsin/14094/99.

As used herein, the term "synergistic" refers to a combination of therapies (e.g., prophylactic or therapeutic agents) which is more effective than the additive effects of any two or more single therapies (e.g., one or more prophylactic or therapeutic agents). A synergistic effect of a combination of therapies (e.g., a combination of prophylactic or therapeutic agents) permits the use of lower dosages of one or more of therapies (e.g., one or more prophylactic or therapeutic agents) and/or less frequent administration of said therapies to a subject with a condition (e.g., a swine influenza virus infection or a condition or symptom associated therewith, an infection other than a swine influenza virus infection or a condition or symptom associated therewith, an IFN treatable disease or a condition in which the attenuated swine influenza viruses can be used as a vector to induce an immune response to a particular antigen associated with the condition). The ability to utilize lower dosages of therapies (e.g., prophylactic or therapeutic agents) and/or to administer said therapies less frequently reduces the toxicity associated with the administration of said therapies to a subject without reducing the efficacy of said therapies in the prevention or treatment of a condition (e.g., a swine influenza virus infection or a condition or symptom associated therewith, an infection other than a swine influenza virus infection or a condition or symptom associated therewith, an IFN treatable disease or a condition in which the attenuated swine influenza viruses can be used as a vector to induce an immune response to a particular antigen associated with the condition). In addition, a synergistic effect can result in improved efficacy of therapies (e.g., prophylactic or therapeutic agents) in the prevention or treatment of a condition (e.g., a swine influenza virus infection or a condition or symptoms associated therewith, an infection other than a swine influenza virus infection or a condition or symptom associated therewith, an IFN treatable disease or a condition in which the attenuated swine influenza viruses can be used as a vector to induce an immune response to a particular antigen associated with the condition). Finally, synergistic effect of a combination of therapies (e.g., prophylactic or therapeutic agents) may avoid or reduce adverse or unwanted side effects associated with the use of any single therapy.

As used herein, the term "T cell receptor modulator" refers to an agent which modulates the phosphorylation of a T cell receptor, the activation of a signal transduction pathway associated with a T cell receptor and/or the expression of a particular protein such as a cytokine. Such an agent may directly or indirectly modulate the phosphorylation of a T cell receptor, the activation of a signal transduction pathway associated with a T cell receptor, and/or the expression of a particular protein such as a cytokine. Examples of T cell receptor modulators include, but are not limited to, peptides, polypeptides, proteins, fusion proteins and antibodies which immunospecifically bind to a T cell receptor or a fragment thereof. Further, examples of T cell receptor modulators include, but are not limited to, proteins, peptides, polypeptides (e.g., soluble T cell receptors), fusion proteins and antibodies that immunospecifically bind to a ligand for a T cell receptor or a fragment thereof.

As used herein, the term "therapeutically effective amount" refers to the amount of a therapy, which is sufficient to reduce the severity of a condition (e.g., a swine influenza virus infection or a condition associated therewith (e.g., influenza induced abortions, depression, inappetance, anorexia, dyspnea, myalgia, or enlarged submandibular lymph nodes), an infection other than a swine influenza virus infection or a condition or symptom associated therewith, an IFN treatable disease or a condition in which the attenuated swine influenza viruses can be used as a vector to induce an immune response to a particular antigen associated with the condition), reduce the duration of a condition (e.g., swine influenza virus infection or a condition associated therewith, an infection other than a swine influenza virus infection or a condition or symptom associated therewith, an IFN treatable disease or a condition in which the attenuated swine influenza viruses can be used as a vector to induce an immune response to a particular antigen associated with the condition), reduce the titer of swine influenza virus or other virus, reduce the number of other pathogens, ameliorate one or more symptoms of a condition (e.g., a swine influenza virus infection or a condition associated therewith, an infection other than a swine influenza virus infection or a condition or symptom associated therewith, an IFN treatable disease or a condition in which the attenuated swine influenza viruses can be used as a vector to induce an immune response to a particular antigen associated with the condition), prevent the advancement of a condition (e.g., a swine influenza virus infection or a condition associated therewith, an infection other than a swine influenza virus infection or a condition or symptom associated therewith, an IFN treatable disease or a condition in which the attenuated swine influenza viruses can be used as a vector to induce an immune response to a particular antigen associated with the condition), cause regression of a condition (e.g., a swine influenza virus infection or a condition associated therewith, an infection other than a swine influenza virus infection or a condition or symptom associated therewith, an IFN treatable disease or a condition in which the attenuated swine influenza viruses can be used as a vector to induce an immune response to a particular antigen associated with the condition), or enhance or improve the therapeutic effect(s) of another therapy.

As used herein, the terms "therapies" and "therapy" can refer to any protocol(s), method(s), compositions, formulations, and/or agent(s) that can be used in the prevention, treatment, management, or amelioration of a condition (e.g., a swine influenza virus infection or a condition or symptom associated therewith, an infection other than a swine influenza virus infection or a condition or symptom associated therewith, an IFN treatable disease or a condition in which the attenuated swine influenza viruses can be used as a vector to induce an immune response to a particular antigen associated with the condition). In certain embodiments, the terms "therapies" and "therapy" refer to biological therapy, supportive therapy, and/or other therapies useful in treatment, management, prevention, or amelioration of a swine influenza virus infection or a condition or symptom associated therewith, an infection other than a swine influenza virus infection or a condition or symptom associated therewith, an IFN treatable disease or a condition in which the attenuated swine influenza viruses can be used as a vector to induce an immune response to a particular antigen associated with the condition, known to one of skill in the art.

As used herein, the terms "therapeutic agent" and "therapeutic agents" refer to any agent(s) which can be used in the prevention, treatment, management, or amelioration of a condition or a symptom thereof (e.g., a swine influenza infection or a condition or symptoms associated therewith, an infection other than a swine influenza virus infection or a condition or symptom associated therewith, an IFN treatable disease or a condition in which the attenuated swine influenza viruses can be used as a vector to induce an immune response to a particular antigen associated with the condition). Preferably, a therapeutic agent is an agent which is known to be useful for, or has been or is currently being used for the prevention, treatment, management, or amelioration of a swine influenza virus infection or a condition or symptoms associated therewith, an infection other than a swine influenza virus infection or a condition or symptom associated therewith, an IFN treatable disease or a condition in which the attenuated swine influenza viruses can be used as a vector to induce an immune response to a particular antigen associated with the condition.

As used herein, the terms "treat," "treatment," and "treating" refer to the eradication or control of swine influenza virus replication or the replication of a pathogen (e.g., a virus) other than swine influenza virus, the reduction in the titer of swine influenza virus or virus other than swine influenza virus, the reduction in the numbers of a pathogen, the reduction or amelioration of the progression, severity, and/or duration of a condition (e.g., a swine influenza virus infection or a condition associated therewith, an infection other than a swine influenza virus infection or a condition or symptom associated therewith, an IFN treatable disease or a condition in which the attenuated swine influenza viruses can be used as a vector to induce an immune response to a particular antigen associated with the condition), or the amelioration of one or more symptoms resulting from the administration of one or more therapies (including, but not limited to, the administration of one or more prophylactic or therapeutic agents).

The term "tumor antigen" as used herein refers to a molecule on a tumor cell that can be specifically recognized by immune T cells or antibodies. A tumor antigen includes those present only on tumor cells (tumor specific antigens) as well as those present on normal cells but expressed preferentially or aberrantly on tumor cells (tumor associated antigens). Examples of tumor antigens include, but are not limited to, antigens of sarcoids, prostate cancer, fibrosarcoma, self-differentiation antigens such as oncofetal, or differentiation, antigens which are expressed by malignant cells, including but not limited to oncofetal antigens such as carcinoembryonio antigens (CEA) of the colon, alpha-fetoprotein, the human antigenic counterpart or functional equivalent of the 175 kDa murine antigen of transitional cell bladder carcinomas, the melanoma associated antigen p97 or GD3, and differentiation antigens of human lung carcinomas such as L6 and L20.

As used herein, the phrase "wild-type swine influenza virus" refers to the types of an swine virus that are prevalent, circulating naturally and producing typical outbreaks of disease. Examples of wild-type swine influenza viruses include, but are not limited to, A/Swine/Colorado/1/77, A/Swine/Colorado/23619/99, A/Swine/Cote d'Armor/3633/84, A/Swine/Cote d'Armor/3633/84, A/Swine/England/195852/92, A/Swine/Finistere/2899/82, A/Swine/Hong Kong/10/98, A/Swine/Hong Kong/9/98, A/Swine/Hong Kong/81/78, A/Swine/Illinois/100084/01, A/Swine/Illinois/100085A/01, A/Swine/Illinois/21587/99, A/Swine/Indiana/1726/88, A/Swine/Indiana/9K035/99, A/Swine/Indiana/P12439/00, A/Swine/Iowa/30, A/Swine/Iowa/15/30, A/Swine/Iowa/533/99, A/Swine/Iowa/569/99, A/Swine/Iowa/3421/90, A/Swine/Iowa/8548-1/98, A/Swine/Iowa/930/01, A/Swine/Iowa/17672/88, A/Swine/Italy/1513-1/98, A/Swine/Italy/1523/98, A/Swine/Korea/CY02/02, A/Swine/Minnesota/55551/00, A/Swine/Minnesota/593/99, A/Swine/Minnesota/9088-2/98, A/Swine/Nebraska/1/92, A/Swine/Nebraska/209/98, A/Swine/Netherlands/12/85, A/Swine/North Carolina/16497/99, A/Swine/North Carolina/35922/

98, A/Swine/North Carolina/93523/01, A/Swine/North Carolina/98225/01, A/Swine/Oedenrode/7C/96, A/Swine/Ohio/891/01, A/Swine/Oklahoma/18717/99, A/Swine/Oklahoma/18089/99, A/Swine/Ontario/01911-1/99, A/Swine/Ontario/01911-2/99, A/Swine/Ontario/41848/97, A/Swine/Ontario/97, A/Swine/Quebec/192/81, A/Swine/Quebec/192/91, A/Swine/Quebec/5393/91, A/Swine/Taiwan/7310/70, A/Swine/Tennessee/24/77, A/Swine/Texas/4199-2/98, A/Swine/Wisconsin/125/97, A/Swine/Wisconsin/136/97, A/Swine/Wisconsin/163/97, A/Swine/Wisconsin/164/97, A/Swine/Wisconsin/166/97, A/Swine/Wisconsin/168/97, A/Swine/Wisconsin/235/97, A/Swine/Wisconsin/238/97, A/Swine/Wisconsin/457/98, A/Swine/Wisconsin/458/98, A/Swine/Wisconsin/464/98 and A/Swine/Wisconsin/14094/99.

4. DESCRIPTION OF THE FIGURES

Figure 1B:
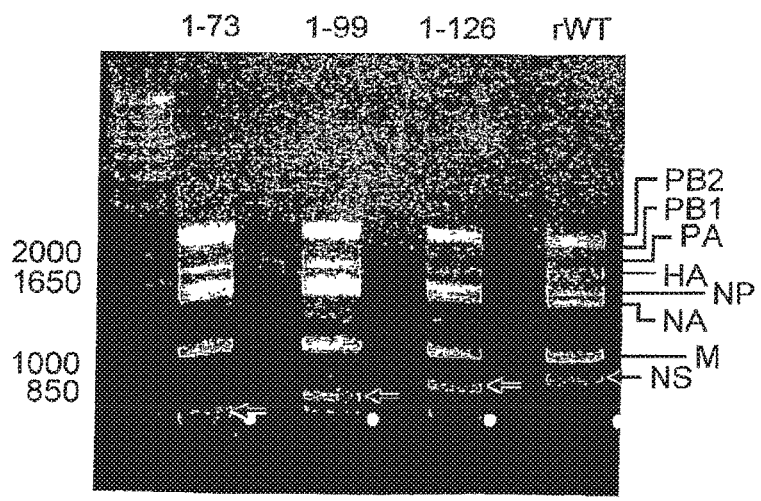

FIGS. 1A-1B. Generation of plasmid-derived Sw/Tx/98 influenza viruses with NS1 mutated proteins. FIG. 1A depicts a schematic diagram of the wild type and mutated NS influenza gene segments. The NS gene segment was modified to create mutated NS1 genes encoding 73, 99 and 126 aa, respectively. NS1 mutations did not affect the sequence of the NEP protein. Underlined sequences were introduced to generate stop codons (in bold) (SEQ ID NOs: 19, 20 and 21, respectively). FIG. 1B depicts RT-PCR analysis of the rWT and NS1 deletion mutant viruses. Influenza viral RNA segments were amplified using primers specific for the non-coding regions of all 8 influenza viral segments. Arrows indicate the decreasing size of the NS segment. Dots indicate a product corresponding to the 3' end of the HA gene segment due to internal binding of the forward primer.

FIGS. 2A-2D. Characterization of plasmid-derived wild-type and NS1 mutant Sw/TX/98 viruses in tissue culture. FIG. 2A shows multi-cycle growth curves of wild-type and NS1 deletion mutants in PK-15 cells. FIG. 2B shows single cycle growth curves of wild-type and NS1 deletion mutants in PK-15 cells. FIG. 2C shows plaque size in MDCK cells at 3 days post infection. FIG. 2D shows a time course of viral protein expression. PK-15 cells infected with rWT and NS1 mutant viruses (MOI=2) and labeled with $[^{35}S]$Met-Cys at the indicated times p.i. Cell extracts were subjected to SDS-PAGE and analyzed by autoradiography.

FIGS. 3A-3C. Induction of type I IFN in PK-15 cells infected with plasmid-derived wild-type and NS1 mutant Sw/TX/98 viruses. FIG. 3A shows a schematic representation of the IFN-bioassay levels of IFN secreted by virus infected cells in a fluorescent assay. FIG. 3B shows a time course of type I IFN synthesis. Fresh PK-15 cells were treated for 24 hours with UV-inactivated supernatants (harvested at different times p.i.) from PK-15 cells which were infected with the indicated viruses, followed by VSV-GFP infection. Sixteen hours post infection, cells expressing GFP were visualized by fluorescence microscopy. the induction of IFN and TNF-α. FIG. 3C shows a RT-PCR analysis of TNF-α, IFN-β- and β-actin-specific mRNAs in virus-infected PK-15 cells.

FIGS. 4A-4C. Infection of 4-week-old pigs with plasmid-derived wild-type and NS1 mutant Sw/TX/98 viruses. FIG. 4A shows a bar chart depicting the histopathological scores of lungs from pigs infected with plasmid-derived TX/98 deletion viruses. Mean percentage (±SEM) of lung surface with macroscopic lesions on day 5 p.i. FIG. 4B shows microscopic lesions in the medium bronchioles on day 5 p.i. FIG. 4C shows virus titers in bronchoalveolar lavage fluid on day 5 p.i.

FIGS. 5A-5D. Histopathological examination of lungs from pigs infected with plasmid-derived wild-type and NS1 mutant Sw/TX/98 viruses, magnification 200×. FIG. 5A shows medium-sized bronchiole from the lung of a non-infected control pig. Epithelial lining is intact, and surrounding alveoli are normal. FIG. 5B shows severe acute necrotizing bronchiolitis and interstitial pneumonia characteristic of the widespread lesion induced by infection with rWT TX/98 virus. FIG. 5C shows one normal bronchiole and one affected bronchiole in early recovery from infection with deletion mutant 1-99 virus, representative of the less extensive injury induced by infection with this virus. FIG. 5D shows normal bronchiole and surrounding alveoli from the lung of a pig inoculated with 1-126 virus. No lesions were induced by this virus.

FIGS. 6A-D. Histopathological examination of lungs from pigs infected with plasmid-derived wild-type and NS1 mutant Sw/TX/98 viruses, magnification 200×. FIG. 6A shows the epithelial lining of a larger bronchiole from the lung of a non-infected control pig. Epithelial cells are tall columnar with pseudo-stratified basal nuclei and prominent surface cilia. FIG. 6B shows the epithelial lining from a larger bronchiole from the lung of a pig infected with TX/98 rWT virus. Epithelial lining is in total disarray due to necrosis and regenerative proliferation of the epithelial cells. FIG. 6C shows a large bronchiole and smaller branching airway from the lung of a pig infected with deletion mutant 1-99 virus, representative of the less extensive injury induced by this virus. FIG. 6D shows a normal epithelial lining from the lung of a pig inoculated with 1-126 virus. No bronchiolar injury resulted.

FIG. 7. Histopathology of TX/98/del 126-vaccinated pigs. FIG. 7 shows a bar chart depicting the histopathological scores of lungs from pigs vaccinated with TX/98/del126. Mock=non vaccinated, sham-inoculated pigs; H3N2=non vaccinated pigs inoculated with $2\times10^5$ PFU per pig with A/Swine/Texas/4199-2/98; H1N1=non-vaccinated pigs inoculated with $2\times10^5$ PFU per pig with A/Swine/MN/37866/99; MLV+Mock=TX/98/del 126 vaccinated, sham inoculated pigs; MLV+H3N2=TX/98/del 126 vaccinated pigs inoculated with $2\times10^5$ PFU per pig with A/Swine/Texas/4199-2/98; MLV+H1N1=TX/98/del 126 vaccinated pigs inoculated with $2\times10^5$ PFU per pig with A/Swine/MN/37866/99.

FIG. 8: Immunohistochemistry for SIV-antigen in TX/98/del 126-vaccinated pigs. FIG. 8 shows a bar chart depicting the immunohistological scores for pigs vaccinated with TX/98/del126. Mock=non vaccinated, sham-inoculated pigs; H3N2=non vaccinated pigs inoculated with $2\times10^5$ PFU per pig with A/Swine/Texas/4199-2/98; H1N1=non-vaccinated pigs inoculated with $2\times10^5$ PFU per pig with A/Swine/MN/37866/99; MLV+Mock=TX/98/del 126 vaccinated, sham inoculated pigs; MLV+H3N2=TX/98/del 126 vaccinated pigs inoculated with $2\times10^5$ PFU per pig with A/Swine/Texas/4199-2/98; MLV+H1N1=TX/98/del 126 vaccinated pigs inoculated with $2\times10^5$ PFU per pig with A/Swine/MN/37866/99.

FIG. 9: Virus titers in lung lavage of TX/98/del 126-immunized pigs challenged with H3N2 and H1N1 SIVs. FIG. 9 shows a bar chart depicting the viral titers in lung lavage from pigs vaccinated with TX/98/del126. Mock=non vaccinated, sham-inoculated pigs; H3N2=non vaccinated pigs inoculated with $2\times10^5$ PFU per pig with A/Swine/Texas/4199-2/98; H1N1=non-vaccinated pigs inoculated with 2×10⁵ PFU per pig with A/Swine/MN/37866/99; MLV+Mock=TX/98/del 126 vaccinated, sham inoculated pigs; MLV+H3N2=TX/98/del 126 vaccinated pigs inoculated with 2×10⁵ PFU per pig with A/Swine/Texas/4199-2/98; MLV+H1N1=TX/98/del 126 vaccinated pigs inoculated with 2×10⁵ PFU per pig with A/Swine/MN/37866/99. The limit of virus detection was $10^{15}$ $TCID_{50}$/ml.

5. DETAILED DESCRIPTION OF THE INVENTION

The present invention provides attenuated swine influenza viruses having an impaired ability to antagonize the cellular interferon (IFN) response, methods for producing such attenuated swine influenza viruses, and the use of such viruses in vaccine and pharmaceutical formulations. Such viruses are capable of generating an immune response and creating immunity but not causing illness, or causing fewer and/or less severe symptoms, i.e., the viruses have decreased virulence. Therefore, they are ideal candidates for live virus vaccines. Moreover, the attenuated swine influenza viruses can induce a robust IFN response which has other biological consequences in vivo, affording protection against subsequent infectious diseases and/or inducing antitumor responses. Therefore, the attenuated swine influenza viruses can be used pharmaceutically, for the prevention or treatment of other infectious diseases and/or IFN-treatable diseases.

The invention is based, in part, on the Applicants' discovery that swine influenza viruses engineered to contain or containing a deletion(s) in the NS1 gene have impaired replication relative to wild-type swine influenza viruses as demonstrated by fewer lung lesions upon infection of pigs, reduced viral titers in bronchoalveolar lavage fluid (BALF) and reduced detection of virus on nasal swabs. Surprisingly, and contrary to results seen with human influenza virus in mouse models, the length of the NS1 protein does not correlate with the level of attenuation of the swine influenza virus. Applicants have discovered that with swine influenza, a mutant virus with the shortest NS1 protein is the least attenuated. In other words, swine influenza viruses containing shorter deletions in the NS1 gene exhibit a greater attenuation in vivo than swine influenza viruses containing longer deletions in their NS1 gene, or wild-type swine influenza viruses. Applicants have further discovered that the recombinant swine influenza viruses are impaired in their ability to inhibit IFN production in vitro, and they do not replicate as efficiently as the parental recombinant strain in 10-day old embryonated hen eggs, in MDCK cells, in PK-15 cells or in an in vivo pig model. While not intending to be bound to any theory or explanation for the mechanism of action of the swine influenza virus NS1 deletion mutants in vivo, the attenuated features of such viruses are presumably due to their levels of NS1 protein expression, their ability to induce a robust cellular IFN response, and their impaired ability to antagonize such a response. However, the beneficial features of such viruses may not be solely attributable to their effect on the cellular interferon response. Indeed, alterations in other activities associated with NS1, such as, alteration of pre-mRNA splicing, inhibition of cellular mRNA polyadenylation, poly(A)-containing mRNA nucleocytoplasmic transport, and stimulation of viral protein synthesis, may contribute to the desired attenuated phenotype achieved by the introduction of mutations in the NS1 gene of swine influenza virus.

An attenuated swine influenza of the present invention comprises a mutation in a swine influenza NS1 gene that diminishes the ability of the NS1 gene product to antagonize the cellular interferon response. In one embodiment, an attenuated swine influenza virus of the invention comprises a genome comprising a mutation in a swine influenza virus NS1 gene that diminishes the ability of the NS1 gene product to antagonize a cellular interferon response, and permits the attenuated virus, at a multiplicity of infection (MOI) of between 0.0005 and 0.001, 0.001 and 0.01, 0.01 and 0.1, or 0.1 and 1, or a MOI of 0.0005, 0.0007, 0.001, 0.005, 0.01, 0.05, 0.1, 0.5, 1.0, 1.5, 2.0, 2.5, 3.0, 3.5, 4.0, 4.5, 5.0, 5.5, or 6.0, to grow to titers between approximately 1 to approximately 100 fold, approximately 5 to approximately 80 fold, approximately 20 to approximately 80 fold, or approximately 40 to approximately 80 fold, approximately 1 to approximately 10 fold, approximately 1 to approximately 5 fold, approximately 1 to approximately 4 fold, approximately 1 to approximately 3 fold, approximately 1 to approximately 2 fold, or approximately 1, 2, 3, 4, 5, 6, 7, 8, 10, 15, 20, 25, 30, 35, 40, 45, 50, 55, 60, 65, 70, 75, 80, 85, 90, 95 or 100 fold lower than wild-type swine influenza virus in cells (e.g., cells of a human (e.g., PerC6, a producer cell line derived from human embryonic retinoblasts transformed with the E1 region of Adenovirus 5), mouse, chicken (e.g., chicken embryo fibroblasts), rat, birds, or pig (e.g., PK(D1) cells, PK(15) cells, PK13 cells, NSK cells, LLC-PK1 cells, LLC-PK1A cells, ESK-4 cells, ST cells, PT-K75 cells, PK-2a/CL 13 or SJPL cells)), as determined approximately 2 to 10 days, 3 to 7 days, 3 to 5 days, or 2, 3, 4, 5, 6, 7, 8, 9, 10 days post-infection when propagated under the same conditions. The titers of attenuated and wild-type swine influenza viruses can be determined utilizing any technique well-known in the art or described herein, (e.g., hemagglutination assays, plaque assays, egg infectious doses (EID50), tissue culture infectious doses (TCID50), etc.) and the viruses can be propagated under conditions described herein or well-known in the art (e.g., in pig cells, MDCK cells (e.g., in MEM, 10% v/v fetal calf serum (FCS), 1% penicillin/streptomycin at 37° C. in a 5% $CO_2$ humidified incubator) or embryonated chicken eggs (e.g., in a stationary incubator at 37° C. with 55% relative humidity). Alternatively, the viruses can be propagated in cells (e.g., in pig cells, MDCK cells, etc.) that are grown in serum-free or serum reduced (e.g., TPCK trypsin) medium. In one embodiment, the growth of an attenuated swine influenza virus of the invention is compared to a particular standard or reference, e.g., wild-type swine influenza virus A/Swine/Texas/4199-2/98.

In a specific embodiment, an attenuated swine influenza virus of the invention comprises a genome comprising a mutation in a swine influenza virus NS1 gene that diminishes the ability of the NS1 gene product to antagonize a cellular interferon response, and permits the attenuated virus, at a multiplicity of infection (MOI) of between 0.0005 and 0.001, 0.001 and 0.01, 0.01 and 0.1, or 0.1 and 1, or a MOI of 0.0005, 0.0007, 0.001, 0.005, 0.01, 0.05, 0.1, 0.5, 1.0, 1.5, 2.0, 2.5, 3.0, 3.5, 4.0, 4.5, 5.0, 5.5, or 6.0, to grow to titers between approximately 1 to approximately 100 fold, approximately 5 to approximately 80 fold, approximately 20 to approximately 80 fold, or approximately 40 to approximately 80 fold, approximately 1 to approximately 10 fold, approximately 1 to approximately 5 fold, approximately 1 to approximately 4 fold, approximately 1 to approximately 3 fold, approximately 1 to approximately 2 fold, or approximately 1, 2, 3, 4, 5, 6, 7, 8, 10, 15, 20, 25, 30, 35, 40, 45, 50, 55, 60, 65, 70, 75, 80, 85, 90, 95 or 100 fold lower than wild-type swine influenza virus in pig cells, as determined approximately 2 to 10 days, 3 to 7 days, 3 to 5 days, or 2, 3, 4, 5, 6, 7, 8, 9, 10 days post-infection when propagated under the same conditions. The titers of attenuated and wild-type swine influenza viruses can be determined utilizing any technique well-known in the art or described herein, (e.g., hemagglutination assays, plaque assays, egg infectious doses (EID50), tissue culture infectious doses (TCID50), etc.) and the viruses can be propagated under conditions described herein or well-known in the art (e.g., in pig cells, MDCK cells (e.g., in MEM, 10% v/v fetal calf serum (FCS), 1% penicillin/streptomycin at 37° C. in a 5% $CO_2$ humidified incubator) or embryonated chicken eggs (e.g., in a stationary incubator at 37° C. with 55% relative humidity). Alternatively, the viruses can be propagated in cells (e.g., in pig cells, MDCK cells, etc.) that are grown in serum-free or serum reduced (e.g., TPCK trypsin) medium.

An attenuated swine influenza virus having the desired phenotype can itself be used as the active ingredient in vaccine, pharmaceutical or immunogenic formulations. Alternatively, the attenuated swine influenza virus can be used as the vector or "backbone" of recombinantly produced vaccines or immunogenic formulations. To this end, the "reverse genetics" technique can be used to engineer mutations or introduce foreign epitopes into the attenuated swine influenza virus, which would serve as the "parental" strain. In this way, vaccines can be designed for immunization against strain variants, or in the alternative, against completely different infectious agents or disease antigens (e.g., tumor antigens). For example, the attenuated virus can be engineered to express neutralizing epitopes of other preselected strains. Alternatively, epitopes of other viruses can be built into the attenuated swine influenza virus. Alternatively, epitopes of non-viral infectious pathogens (e.g., parasites, bacteria, fungi) can be engineered into the attenuated swine influenza virus.

The present invention provides methods for vaccinating a subject comprising administering the vaccine formulations of the invention. In one embodiment, the present invention provides a method comprising administering to a subject an effective amount of a vaccine formulation of the invention. In certain embodiments, the dose of the vaccine formulation administered to the subject is between about $10^2$ to about $10^8$, about $10^3$ to about $10^7$, or about $10^4$ to about $5 \times 10^6$ pfu. In other embodiments, the dose of the vaccine formulation administered is $10^2$, $5 \times 10^2$, $10^3$, $5 \times 10^3$, $10^4$, $5 \times 10^4$, $10^5$, $5 \times 10^5$, $10^6$, $5 \times 10^6$, $10^7$, $5 \times 10^7$ or $10^8$ pfu. In other embodiments, the dose of an immunogenic formulation of the invention administered to a subject is $10^2$ to about $10^8$, about $10^3$ to about $10^7$, or about $10^4$ to about $5 \times 10^6$ pfu. In yet other embodiments, the dose of an immunogenic formulation of the invention administered to a subject is $10^2$, $5 \times 10^2$, $10^3$, $5 \times 10^3$, $10^4$, $5 \times 10^4$, $10^5$, $5 \times 10^5$, $10^6$, $5 \times 10^6$, $10^7$, $5 \times 10^7$ or $10^8$ pfu. In specific embodiments, the subject is a donkey, zebra, camel, dog, avian (e.g., a duck). In a preferred embodiment, the subject is a pig.

The present invention provides immunogenic formulations comprising an attenuated swine influenza virus of the invention and methods for inducing an immune response for the treatment, management or prevention of a swine influenza virus infection or a condition or symptom associated therewith, an infection other than a swine influenza virus infection or a condition or symptom associated therewith, or a condition in which the attenuated swine influenza viruses can be used as a vector to induce an immune response to a particular antigen associated with the condition, comprising administering to a subject an immunogenic formulation of the invention. In one embodiment, the present invention provides a method for inducing an immune response for the treatment, management or prevention of a swine influenza virus infection or a condition or symptom associated therewith, an infection other than a swine influenza virus infection or a condition or symptom associated therewith, or a condition in which the attenuated swine influenza viruses can be used as a vector to induce an immune response to a particular antigen associated with the condition, comprising administering to a subject an effective amount of an immunogenic formulation of the invention. In certain embodiments, the dose of the immunogenic formulation administered to the subject is between about $10^2$ to about $10^8$, about $10^3$ to about $10^7$, about $10^4$ to about $5 \times 10^6$ pfu or about $10^4$ to about $10^7$ pfu. In other embodiments, the dose of an immunogenic formulation of the invention administered to a subject is $10^2$, $5 \times 10^2$, $10^3$, $5 \times 10^3$, $10^4$, $5 \times 10^4$, $10^5$, $5 \times 10^5$, $10^6$, $5 \times 10^6$, $10^7$, $5 \times 10^7$ or $10^8$ pfu. In specific embodiments, the subject is a donkey, zebra, camel, dog, avian (e.g., a duck). In a preferred embodiment, the subject is a pig.

The attenuated swine influenza viruses, which induce robust IFN responses in subjects, may also be used in pharmaceutical formulations for the prophylaxis or treatment of other infections, or IFN-treatable diseases such as cancer. In this regard, the tropism of the attenuated swine influenza virus can be altered to target the virus to a desired target organ, tissue or cells in vivo or ex vivo. Using this approach, the IFN response can be induced locally, at the target site, thus avoiding or minimizing the side effects of systemic IFN treatments. To this end, the attenuated swine influenza virus can be engineered to express a ligand specific for a receptor of the target organ, tissue or cells.

The present invention provides methods for preventing, managing or treating an infection or IFN-treatable disease in a subject, other than a swine influenza viral infection or IFN-treatable disease caused by swine influenza virus, comprising administering a pharmaceutical formulation of the invention. In one embodiment, the present invention provides a method for preventing, managing or treating an infection or IFN-treatable disease in a subject, other than a swine influenza viral infection or IFN-treatable disease caused by swine influenza virus, comprising administering an effective amount of a pharmaceutical formulation of the invention. In certain embodiments, the dose of the pharmaceutical formulation administered to the subject is between about $10^2$ to about $10^8$, about $10^3$ to about $10^7$, about $10^4$ to about $5 \times 10^6$ pfu or about $10^4$ to about $10^{12}$ pfu. In other embodiments, the dose of the pharmaceutical formulation administered to the subject is $10^2$, $5 \times 10^2$, $10^3$, $5 \times 10^3$, $10^4$, $5 \times 10^4$, $10^5$, $5 \times 10^5$, $10^6$ $5 \times 10^6$ $10^7$ $5 \times 10^7$ $10^8$ $5 \times 10^8$ $1 \times 10^9$ $5 \times 10^9$ $1 \times 10^{10}$, $5 \times 10^{10}$, $1 \times 10^{11}$, $5 \times 10^{11}$ or $10^{12}$ pfu. In specific embodiments, the subject is a donkey, zebra, camel, dog, avian (e.g., a duck). In a preferred embodiment, the subject is a pig.

The present invention provides methods for preventing, managing or treating cancer in a subject comprising administering a pharmaceutical composition of the invention. In one embodiment, the present invention provides a method for preventing, managing or treating cancer in a subject comprising administering an effective amount of a pharmaceutical composition of the invention. In certain embodiments, the dose of the pharmaceutical formulation administered to the subject is between about $10^2$ to about $10^8$, about $10^3$ to about $10^7$, about $10^4$ to about $5 \times 10^6$ pfu or about $10^4$ to about $10^{12}$ pfu. In other embodiments, the dose of the pharmaceutical formulation administered to the subject is $10^2$, $5 \times 10^2$, $10^3$, $5 \times 10^3$, $10^4$, $5 \times 10^4$, $10^5$, $5 \times 10^5$, $10^6$, $5 \times 10^6$, $10^7$, $5 \times 10^7$, $10^8$, $5 \times 10^8$, $1 \times 10^9$, $5 \times 10^9$, $1 \times 10^{10}$, $5 \times 10^{10}$, $1 \times 10^{11}$, $5 \times 10^{11}$ or $10^{12}$ pfu.

Applicants demonstrated that attenuated swine influenza viruses with impaired interferon antagonist activity were shown to replicate in vivo generating titers that are lower than than detected with wild-type swine influenza viruses, but that are sufficient to induce immunological and cytokine responses. Thus, mutations which diminish but do not abolish the IFN antagonist activity of the swine influenza virus are preferred for vaccine formulations. Such viruses can be selected for growth in both conventional and non-conventional substrates, and for intermediate virulence.

The present invention provides cells containing (alternatively, comprising) swine influenza viruses of the present invention. In a specific embodiment, a cell contains/comprises a swine influenza virus that is genetically engineered. In certain embodiments, the attenuated swine influenza virus contained in the cell is engineered to encode an epitope derived from another virus or a tumor antigen. In accordance with this embodiment, the genome of the attenuated swine influenza virus may comprise at least one segment derived from a different virus. Any cell can be infected with, contain or comprise an attenuated swine influenza virus of the invention including, but not limited to, MDCK cells, PK cells, Vero cells, primary human umbilical vein endothelial cells (HUVEC), H292 human epithelial cell line, HeLa cells, and swine embryonic kidney cells RES. In a preferred embodiment, the cell is a pig cell or a pig cell line. In certain embodiments, the cell (e.g., a pig cell or pig cell line) is interferon deficient.

The invention encompasses the use of substrates such as cells, cell lines and embryonated eggs, to propagate the attenuated swine influenza viruses of the invention. In one embodiment, the invention provides methods for vaccine production, immunogenic formulation production and pharmaceutical production comprising propagating in a substrate an attenuated swine influenza virus of the present invention and collecting progeny virus, wherein the substrate is a cell, cell line or embryonated egg. In certain embodiments, the substrate is an IFN deficient system. Exemplary IFN-deficient systems include, but are not limited to, young embryonated eggs (e.g., 6 to 10 days old, 6 to 9 days old, 6 to 8 days old or 6 to 7 days old embryonated eggs), IFN-deficient cell lines (such as VERO cells or genetically engineered cell lines such as STAT1 knockouts). Embryonated eggs or cell lines pretreated with compounds that inhibit the IFN system (including drugs, antibodies, antisense, ribozymes, etc.) can also be used as an IFN-deficient system. Further, eggs deficient in the IFN system, e.g., eggs produced by STAT1 negative birds, especially fowl, including but not limited to transgenic chickens, ducks or turkeys, may be used as an IFN-deficient system.

5.1 Generation of Mutants with Altered IFN Antagonist Activity

Any mutant swine influenza virus or strain which has a decreased IFN antagonist activity can be selected and used in accordance with the invention. In one embodiment, naturally occurring mutants or variants, or spontaneous swine influenza mutants can be selected that have an impaired ability to antagonize the cellular IFN response. In another embodiment, mutant swine influenza viruses can be generated by exposing the virus to mutagens, such as ultraviolet irradiation or chemical mutagens, or by multiple passages and/or passage in non-permissive hosts. Screening in a differential growth system can be used to select for those mutants having impaired IFN antagonist function. Since swine influenza virus A has a segmented genome, the attenuated phenotype can be transferred to another strain having a desired antigen by reassortment, (i.e., by coinfection of the attenuated virus and the desired strain, and selection for reassortants displaying both phenotypes). In a specific embodiment, the swine influenza viruses of the invention are not naturally occurring viruses. In another specific embodiment, the swine influenza viruses of the invention are genetically engineered viruses. In yet another specific embodiment, a swine influenza virus with naturally occurring mutations in the NS1 gene are not encompassed by the invention. In yet another specific embodiment, known swine influenza viruses with mutations in the NS1 gene are not encompassed by the invention. In specific embodiments, the swine influenza viruses of the invention contain all or a portion of the NS1 gene derived from human influenza viruses.

Mutations can be engineered into swine influenza virus using "reverse genetics" approaches. In this way, natural or other mutations which confer the attenuated phenotype can be engineered into vaccine strains. For example, deletions, insertions or substitutions of the coding region of the swine influenza virus gene for IFN antagonist activity (i.e., the NS1 of swine influenza virus) can be engineered. Deletions, substitutions or insertions in the non-coding region of the swine influenza virus gene responsible for IFN antagonist activity are also contemplated. To this end, mutations in the signals responsible for the transcription, replication, polyadenylation and/or packaging of the gene responsible or the IFN-antagonist activity can be engineered. Such mutations, for example to the promoter, could down-regulate the expression of the swine influenza virus gene responsible for IFN antagonist activity. Mutations in the promoter can be made, for example, by promoter shuffling (e.g., of the influenza B virus promoter), or in the noncoding regions of the NS1 gene. Mutations in swine influenza virus genes which may regulate the expression of the swine influenza virus gene responsible for IFN antagonist activity (i.e., the swine influenza virus NS1 gene) are also within the scope of viruses that can be used in accordance with the invention.

The present invention also provides swine influenza viruses comprising genomes comprising mutations to the NS1 gene segment that may not result in an altered IFN antagonist activity or an IFN-inducing phenotype but rather results in altered viral functions and an attenuated phenotype, e.g., altered inhibition of nuclear export of poly(A)-containing mRNA, altered inhibition of pre-mRNA splicing, altered inhibition of the activation of PKR by sequestering of dsRNA, altered effect on translation of viral RNA and altered inhibition of polyadenylation of host mRNA (e.g., see Krug in Textbook of Influenza, Nicholson et al. Ed. 1998, 82-92, and references cited therein).

The reverse genetics technique involves the preparation of synthetic recombinant viral RNAs that contain the non-coding regions of the swine influenza virus RNA which are essential for the recognition by viral polymerases and for packaging signals necessary to generate a mature virion. The recombinant RNAs are synthesized from a recombinant DNA template and reconstituted in vitro with purified viral polymerase complex to form recombinant ribonucleoproteins (RNPs) which can be used to transfect cells. A more efficient transfection is achieved if the viral polymerase proteins are present during transcription of the synthetic RNAs either in vitro or in vivo. The synthetic recombinant RNPs can be rescued into infectious virus particles. The foregoing techniques are described in U.S. Pat. No. 5,166,057 issued Nov. 24, 1992; in U.S. Pat. No. 5,854,037 issued Dec. 29, 1998; in European Patent Publication EP 0702085A1, published Feb. 20, 1996; in U.S. patent application Ser. No. 09/152,845; in International Patent Publications PCT WO97/12032 published Apr. 3, 1997; WO96/34625 published Nov. 7, 1996; in European Patent Publication EP-A780475; WO 99/02657 published Jan. 21, 1999; WO 98/53078 published Nov. 26, 1998; WO 98/02530 published Jan. 22, 1998; WO 99/15672 published Apr. 1, 1999; WO 98/13501 published Apr. 2, 1998; WO 97/06270 published Feb. 20, 1997; and EPO 780 475A1 published Jun. 25, 1997, each of which is incorporated by reference herein in its entirety.

The helper-free plasmid technology can also be utilized to engineer an attenuated swine influenza virus. For a description of helper-free plasmid technology see, e.g., International Publication No. WO 01/04333; U.S. Pat. No. 6,649,372; Fodor et al., 1999, J. Virol. 73:9679-9682; Hoffmann et al., 2000, Proc. Natl. Acad. Sci. USA 97:6108-6113; and Neumann et al., 1999, Proc. Natl. Acad. Sci. USA 96:9345-9350, which are incorporated herein by reference in their entireties.

Attenuated viruses generated by the reverse genetics approach or helper-free plasmid technology can be used in the vaccine, immunogenic and pharmaceutical formulations described herein. Reverse genetics techniques or helper-free plasmid technology can also be used to engineer additional mutations to other viral genes important for vaccine, immunogenic and pharmaceutical formulation production—i.e., the epitopes of useful vaccine strain variants can be engineered into the attenuated swine influenza virus. Alternatively, completely foreign epitopes, including antigens derived from other viral or non-viral pathogens can be engineered into the attenuated strain. For example, antigens of non-related viruses, parasite antigens, bacterial or fungal antigens or tumor antigens can be engineered into the attenuated strain (e.g., epitopes of porcine reproductive and respiratory syndrome virus, porcine cytomegalo virus, porcine respiratory corona virus, porcine encephalomyocarditis virus, porcine epidemic diarrhea and antigenic determinants of non-viral swine pathogens such as bacteria, including, but not limited to, *Brucella suis*, and parasites, including, but not limited to, roundworms (*Ascaris suum*), whipworms (*Trichuris suis*), or a tumor antigen such as carcinoembryonic antigen (CEA), breast cancer antigen such as EGFR (Epidermal growth factor receptor), HER2 antigen (p185$^{HER2}$), HER2 neu epitope, cancer antigen-50 (CA-50), cancer antigen 15-3 (CA15-3) associated with breast cancer, carcinoma associated antigen (CAA), melanoma antigen, and melanoma associated antigens 100, 25, and 150). Alternatively, epitopes which alter the tropism of the virus in vivo can be engineered into the chimeric attenuated viruses of the invention.

In a specific embodiment, a combination of reverse genetics techniques or helper-free technology and reassortant techniques can be used to engineer attenuated viruses having the desired epitopes in swine influenza viruses. For example, an attenuated swine influenza virus (generated by, e.g., reverse genetics techniques, helper-free plasmid technology or a combination thereof) and a strain carrying the desired vaccine epitope (generated by, e.g., natural selection, mutagenesis, by reverse genetics techniques, helper-free plasmid technology or a combination thereof) can be co-infected in hosts that permit reassortment of the segmented genomes. Reassortants that display both the attenuated phenotype and the desired epitope can then be selected. In a particular embodiment, reassortant techniques can be used to transfer the attenuated phenotype from a parental swine influenza virus strain (a natural mutant, a mutagenized virus, or a genetically engineered virus) to a different virus strain (a wild-type virus, a natural mutant, a mutagenized virus, or a genetically engineered virus).

In a specific embodiment, the present invention provides an attenuated swine influenza virus comprising a genome comprising a mutation in the swine influenza virus NS1 gene that diminishes the ability of the NS1 gene product to antagonize a cellular interferon response. In accordance with this embodiment, the attenuated swine influenza virus is preferably genetically engineered.

The attenuated swine influenza viruses of the invention may have one or more or a combination of any of the following characteristics: the ability to induce interferon activity at a level less than (e.g., 5%, 10%, 15%, 20%, 25%, 30%, 35%, 40%, 45%, 50%, 55%, 60%, 65%, 70%, 75%, 80%, 85%, 90%, 95% or 98% less than) that of wild-type swine influenza virus, e.g., A/Swine/Texas/4199-2/98, as measured by standard interferon assays; a viral titer 1 to 50, 2 to 25, 2 to 10 or 3 to 7 fold lower than wild-type swine influenza virus, e.g., A/Swine/Texas/4199-2/98, when grown under the same conditions (e.g., inoculated at a MOI of 0.0001, 0.0005, 0.001, 0.005, 0.01, 0.05, 0.1, 0.5, 1, 5 or 10 and grown in PK cells, PK(D1) cells, PK(15) cells, PK13 cells, NSK cells, LLC-PK1 cells, LLC-PK1A cells, ESK-4 cells, ST cells, PT-K75 cells, PK-2a/CL 13 cells or SJPL cells and assayed in MDCK cells); a viral titer 1 to 10 fold, 1 to 5 fold, 5-10 fold, 10 to 500, 20 to 250, 20 to 100 or 40 to 80 fold lower than wild-type swine influenza virus, e.g., A/Swine/Texas/4199-2/98, when isolated from BALF of infected pigs as assayed in a plaque assay performed on MDCK cells; or a reduced ability to cause lung lesions in infected pigs.

In a specific embodiment, an attenuated swine influenza virus of the invention comprises a genome comprising a mutation in a swine influenza virus NS1 gene that diminishes the ability of the NS1 gene product to antagonize a cellular interferon response, and permits the attenuated virus, at a multiplicity of infection (MOI) of between 0.0005 and 0.001, 0.001 and 0.01, 0.01 and 0.1, 0.1 and 1, or 0.1 and 1, or a MOI of 0.0005, 0.0007, 0.001, 0.005, 0.01, 0.05, 0.1, 0.5, 1.0, 1.5, 2.0, 2.5, 3.0, 3.5, 4.0, 4.5, 5.0, 5.5, or 6.0, to grow to titers between approximately 1 to approximately 100 fold, approximately 5 to approximately 80 fold, approximately 20 to approximately 80 fold, or approximately 40 to approximately 80 fold, approximately 1 to approximately 10 fold, approximately 1 to approximately 5 fold, approximately 1 to approximately 4 fold, approximately 1 to approximately 3 fold, approximately 1 to approximately 2 fold, or approximately 1, 2, 3, 4, 5, 6, 7, 8, or approximately 1, 2, 3, 4, 5, 7, 10, 15, 20, 25, 30, 35, 40, 45, 50, 55, 60, 65, 70, 75, 80, 85, 90, 95 or 100 fold lower than wild-type swine influenza virus in cells (e.g., cells of a human (e.g., PerC6, a producer cell line derived from human embryonic retinoblasts transformed with the E1 region of Adenovirus 5), mouse, chicken (e.g., chicken embryo fibroblasts), rat, birds, or pig (e.g., PK(D1) cells, PK(15) cells, PK13 cells, NSK cells, LLC-PK1 cells, LLC-PK1A cells, ESK-4 cells, ST cells, PT-K75 cells, PK-2a/CL 13 or SJPL cells)) as determined by a hemagglutination assay of BALF obtained from pigs or supernatants of pig cells approximately 2 to 10 days, 3 to 7 days, 3 to 5 days or 2, 3, 5, 6, 7, 8, 9, 10 days post-infection or when the viruses are plagued on MDCK cells. In one embodiment, the growth of an attenuated swine influenza virus of the invention is compared to a particular standard or reference, e.g., wild-type swine influenza virus A/Swine/Texas/4199-2/98. In accordance with these embodiments, the attenuated virus may be genetically engineered to contain or express non-swine influenza virus nucleic acid sequences such, e.g., an epitope of a foreign pathogen or a tumor antigen. Preferably, the non-swine influenza virus sequences do not include a nucleic acid sequence that alters the attenuated phenotype of the virus. Accordingly, nucleic acid sequences encoding proteins, polypeptides or peptides with interferon antagonizing activity are preferably not engineered into swine influenza virus.

The invention provides attenuated swine influenza viruses comprising a genome comprising at least two, at least three, at least four or more mutations in two, three, four or more swine influenza virus genes, wherein at least one of the mutations is in the NS1 gene and contributes to or is responsible (directly or indirectly) for the attenuation of the virus and/or the diminished ability of the virus to antagonize a cellular interferon response. In a specific embodiment, an attenuated swine influenza virus of the invention comprises a genome comprising at least two, at least three, at least four or more mutations in two, three, four or more swine influenza virus genes, wherein at least one of the mutations is in the NS1 gene and is responsible for the diminished ability of the NS1 gene product to antagonize a cellular interferon response, and permits the attenuated virus, at a MOI of between 0.0005 and 0.001, 0.001 and 0.01, 0.01 and 0.1, or 0.1 and 1, or MOI of 0.0005, 0.0007, 0.001, 0.005, 0.01, 0.05, 0.1, 0.5, 1.0, 1.5, 2.0, 2.5, 3.0, 3.5, 4.0, 4.5, 5.0, 5.5, or 6.0, to grow to titers between approximately 1 to approximately 100 fold, approximately 5 to approximately 80 fold, approximately 20 to approximately 80 fold, or approximately 40 to approximately 80 fold, approximately 1 to approximately 10 fold, approximately 1 to approximately 5 fold, approximately 1 to approximately 4 fold, approximately 1 to approximately 3 fold, approximately 1 to approximately 2 fold, or approximately 1, 2, 3, 4, 5, 6, 7, 8, 10, 15, 20, 25, 30, 35, 40, 45, 50, 55, 60, 65, 70, 75, 80, 85, 90, 95 or 100 fold lower than wild-type swine influenza virus, e.g., A/Swine/Texas/4199-2/98, in pig cells, as determined by, e.g., hemagglutination assays, approximately 2 to 10 days, 3 to 7 days, or 2, 3, 5, 6, 7, 8, 9, 10 days post-infection when the viruses are propagated under the same conditions. In another embodiment, an attenuated swine influenza virus of the invention comprises a genome comprising at least two, three, four or more mutations in two, three, four or more swine influenza virus genes, wherein at least one of the mutations is in the NS1 gene and is responsible for the attenuation of the virus, and permits the attenuated virus, at a MOI of between 0.0005 and 0.001, 0.001 and 0.01, 0.01 and 0.1, or 0.1 and 1, or a MOI of 0.0005, 0.0007, 0.001, 0.005, 0.01, 0.05, 0.1, 0.5, 1.0, 1.5, 2.0, 2.5, 3.0, 3.5, 4.0, 4.5, 5.0, 5.5, or 6.0, to grow to titers between approximately 1 to approximately 100 fold, approximately 5 to approximately 80 fold, approximately 20 to approximately 80 fold, or approximately 40 to approximately 80 fold, approximately 1 to approximately 10 fold, approximately 1 to approximately 5 fold, approximately 1 to approximately 4 fold, approximately 1 to approximately 3 fold, approximately 1 to approximately 2 fold, or approximately 1, 2, 3, 4, 5, 6, 7, 8, 10, 15, 20, 25, 30, 35, 40, 45, 50, 55, 60, 65, 70, 75, 80, 85, 90, 95 or 100 fold lower than wild-type swine influenza virus, e.g., A/Swine/Texas/4199-2/98, in pig cells, as determined by, e.g., hemagglutination assays, approximately 2 to 10 days, 3 to 7 days, 3 to 5 days, or 2, 3, 5, 6, 7, 8, 9, 10 days post-infection when the viruses are propagated under the same conditions (e.g., in MDCK cells). In accordance with these embodiments, the attenuated virus have an impaired interferon antagonist phenotype and the viruses may be genetically engineered to contain or express non-swine influenza virus nucleic acid sequences, such as, e.g., an epitope of a foreign pathogen (e.g., epitopes of porcine reproductive and respiratory syndrome virus, porcine cytomegalo virus, porcine respiratory corona virus, porcine encephalomyocarditis virus, porcine epidemic diarrhea and antigenic determinants of non-viral pathogens such as bacteria and parasites, to name but a few) or a tumor antigen. Preferably, the non-swine influenza virus sequences (heterologous sequences) do not include a nucleic acid sequence that alters the attenuated phenotype of the virus. Accordingly, nucleic acid sequences encoding proteins, polypeptides or peptides with interferon antagonizing activity are preferably not engineered into the swine influenza virus.

Any mutation that results in the desired phenotype (preferably, an impaired ability to antagonize a cellular interferon response) can be introduced into the swine influenza virus NS1 gene. Examples of the types of mutations that can be included in or introduced into swine influenza virus NS1 gene include, but are not limited to, deletions, substitutions, insertions and combinations thereof. One or more mutations can be located anywhere throughout the NS1 gene (e.g., the amino-terminus, the carboxy-terminus or somewhere in between) and/or the regulatory element of the NS1 gene. In a specific embodiment, an attenuated swine influenza virus of the invention comprises a genome comprising a swine influenza virus NS1 gene with a mutation (e.g., a deletion or substitution) at the amino-terminus. In a preferred embodiment, an attenuated swine influenza virus of the invention comprises a genome comprising a swine influenza virus with a mutation (e.g., a deletion or substitution, preferably a deletion) at the carboxy-terminus. In another embodiment, an attenuated swine influenza virus of the invention comprises a genome comprising a mutation in a swine influenza virus NS1 gene resulting in a deletion consisting of 5, preferably 10, 15, 20, 25, 30, 35, 40, 45, 50, 55, 60, 65, 70, 73, 75, 80, 85, 90, 95, 99, 100, 105, 110, 115, 120, 125, 126, 130, 135, 140, 145, 150, 155, 160, 165, 170 or 175 amino acid residues from the carboxy terminus of NS1, or a deletion of between 5-170, 25-170, 50-170, 100-170, 100-160 or 105-160 amino acid residues from the carboxy-terminus. In another embodiment, an attenuated swine influenza virus of the invention comprises a genome comprising a mutation in a swine influenza virus NS1 gene resulting in a deletion of all amino acid residues except amino acid residues 1-126, amino acid residues 1-120, amino acid residues 1-115, amino acid residues 1-110, amino acid residues 1-100, amino acid residues 1-99, amino acid residues 1-95, amino acid residues 1-85, amino acid residues 1-80, amino acid residues 1-75, amino acid residues 1-73, amino acid residues 1-70, amino acid residues 1-65 or amino acid residues 1-60, wherein the amino terminal amino acid is number 1. In accordance with these embodiments, the attenuated swine influenza virus is preferably genetically engineered. In a preferred embodiment, an attenuated swine influenza virus of the invention is TX/98/del 126, TX/98/del 99 or TX/98/del 73. In a more preferred embodiment, the attenuated swine influenza virus is TX/98/del 126. In a still more preferred embodiment, the attenuated swine influenza virus is TX/98/del 99.

The attenuated swine influenza virus of the present invention may be a chimeric virus that expresses a heterologous sequence e.g., antigens of other vaccine strains (e.g., using reverse genetics, reassortment or helper-free plasmid technology). Alternatively, the attenuated influenza viruses may be engineered, using reverse genetics, reassortment or helper-free plasmid technology with genetically engineered viruses, to express completely foreign epitopes, e.g., antigens of other infectious pathogens, tumor antigens, or targeting antigens. In certain embodiments, the attenuated swine influenza viruses express a heterologous sequence derived from other swine infectious agents, non-swine infectious agents, swine or other types of tumor antigens (e.g., carcinoembryonic antigen (CEA), breast cancer antigen such as EGFR (epidermal growth factor receptor), HER2 antigen (p185HER2), HER2 neu epitope, cancer antigen-50 (CA-50), cancer antigen 15-3 (CA15-3) associated with breast cancer, carcinoma associated antigen (CAA), melanoma antigen, and melanoma associated antigens 100, 25, and 150). In other embodiments, the attenuated swine influenza virus of the present invention may contain a segment derived from another virus. Since the NS RNA segment is the shortest among the eight viral RNAs, it is possible that the NS RNA will tolerate longer insertions of heterologous sequences than other viral genes. Moreover, the NS RNA segment directs the synthesis of high levels of protein in infected cells, suggesting that it would be an ideal segment for insertions of foreign antigens. Exemplary sequences include epitopes of porcine reproductive and respiratory syndrome virus, porcine cytomegalo virus, porcine respiratory corona virus, porcine encephalomyocarditis virus, porcine epidemic diarrhea and antigenic determinants of non-viral swine pathogens such as bacteria, including, but not limited to, *Brucella suis*, and parasites, including, but not limited to, roundworms (*Ascaris suum*), whipworms (*Trichuris suis*).

Preferably, the heterologous sequence is not a nucleic acid sequence that alters the attenuated phenotype of the virus. Accordingly, preferably, nucleic acid sequences encoding proteins, polypeptides or peptides with interferon antagonizing activity are not engineered into the swine influenza virus. In certain embodiments, the chimeric virus expresses a tumor antigen. In other embodiments, the chimeric virus expresses an epitope of a foreign pathogen.

5.2 Selection of Attenuated Swine Influenza Viruses

The invention encompasses methods of selecting swine influenza viruses which have the desired phenotype, i.e., attenuated swine influenza viruses or swine influenza viruses which have low IFN activity (i.e., a reduction of 5-10%, 10-20%, 20-30%, 30-40%, 40-50%, 50-60%, 60-70%, 70-80%, 80-90% or more when compared to wild-type swine influenza viruses, e.g., A/Swine/Texas/4199-2/98, under the same conditions) or no IFN antagonist activity whether obtained from natural variants, spontaneous variants (i.e., variants which evolve during virus propagation), mutagenized natural variants, reassortants and/or genetically engineered viruses (see, e.g., U.S. Pat. No. 6,635,416). Such viruses can be best screened in differential growth assays that compare growth in IFN-deficient versus IFN-competent host systems. Viruses which demonstrate better growth in the IFN-deficient systems versus IFN competent systems are selected; preferably, viruses which grow to titers at least one log, at least two logs, three logs, or 1 to 50, 1 to 25, 1 to 20, 1 to 10 or 1 to 5 logs greater in IFN-deficient systems as compared to an IFN-competent system are selected. Exemplary IFN-deficient systems include, but are not limited to, young embryonated eggs (e.g., 6 to 10 days old, 6 to 9 days old, 6 to 8 days old or 6 to 7 days old embryonated eggs), IFN-deficient cell lines (such as VERO cells or genetically engineered cell lines such as STAT1 knockouts, PKR knockouts, etc.). Embryonated eggs or cell lines pretreated with compounds that inhibit the IFN system (including drugs, antibodies, antisense, ribozymes, etc.) can also be used as an IFN-deficient system. Further, eggs deficient in the IFN system, e.g., eggs produced by STAT1 negative birds, especially fowl, including but not limited to transgenic chickens, ducks or turkeys, may be used as an IFN-deficient system. Attenuated swine influenza viruses showing at least 1 to 50, 1 to 25, 1 to 20, 1 to 10 or 1 to 5 logs lower titers in 10-days-old eggs versus 6-7, 6-8, or 6-9 days old eggs will be considered impaired in their ability to inhibit the IFN response.

For purposes of screening, transient IFN-deficient systems can be used in lieu of genetically manipulated systems. For example, the host system can be treated with compounds that inhibit IFN production and/or components of the IFN response (e.g., drugs, antibodies against IFN, antibodies against IFN-receptor, inhibitors of PKR, antisense molecules and ribozymes, etc.). Growth of attenuated swine influenza virus can be compared in IFN-competent untreated controls versus IFN-deficient treated systems.

Growth of swine influenza virus (as measured by titer) can, e.g., be compared in a variety of cells, cell lines, or animal model systems that express IFN and the components of the IFN response, versus cells, cell lines, or animal model systems deficient for IFN or components of the IFN response. Techniques which are well known in the art for the propagation of viruses in cell lines can be used (see, for example, the working examples infra). Growth of swine influenza virus in an IFN competent cell line versus an IFN deficient genetically engineered cell line can be compared.

The swine influenza viruses can be screened using IFN assay systems e.g., transcription based assay systems in which reporter gene expression is controlled by an IFN-responsive promoter. Reporter gene expression in infected versus uninfected cells can be measured to identify viruses which efficiently induce an IFN response, but which are unable to antagonize the IFN response. For example, test cells can be engineered to transiently or constitutively express reporter genes such as luciferase reporter gene or chloramphenicol transferase (CAT) reporter gene under the control of an interferon stimulated response element, such as the IFN-stimulated promoter of the ISG-54K gene (Bluyssen et al., 1994, Eur. J. Biochem. 220:395-402). Cells are infected with the test swine influenza virus and the level of expression of the reporter gene compared to that in uninfected cells or cells infected with wild-type swine influenza virus. An increase in the level of expression of the reporter gene following infection with the test attenuated swine influenza virus would indicate that the test swine influenza virus is inducing an IFN response. Alternatively, the induction of IFN responses may be determined by measuring IFN-dependent transcriptional activation following infection with the test attenuated swine influenza virus. The expression of genes known to be induced by IFN, e.g., Mx, PKR, 2-5-oligoadenylatesynthetase, major histocompatibility complex (MHC) class I, etc., can be analyzed by techniques known to those of skill in the art (e.g., northern blots, western blots, PCR, etc.). The induction of IFN responses may also be determined by measuring the phosphorylated state of components of the IFN pathway following infection with a test swine influenza virus, e.g., IRF-3, which is phosphorylated in response to double-stranded RNA. In response to type I IFN, Jak1 kinase and TyK2 kinase, subunits of the IFN receptor, STAT1, and STAT2 are rapidly tyrosine phosphorylated. Thus, in order to determine whether the swine influenza virus induces IFN responses, cells, such as 293 cells, are infected with the test mutant virus and following infection, the cells are lysed. IFN pathway components, such as Jak1 kinase or TyK2 kinase, are immunoprecipitated from the infected cell lysates, using specific polyclonal sera or antibodies, and the tyrosine phosphorylated state of the kinase is determined by immunoblot assays with an anti-phosphotyrosine antibody (e.g., see Krishnan et al. 1997, Eur. J. Biochem. 247: 298-305). An enhanced phosphorylated state of any of the components of the IFN pathway following infection with the swine influenza virus would indicate induction of IFN responses by the swine influenza virus.

Further, the induction of IFN responses following infection with a test swine influenza virus may be determined by measuring the ability to bind specific DNA sequences or the translocation of transcription factors induced in response to viral infection, e.g., IRF3, STAT1, STAT2, etc. In particular, STAT1 and STAT2 are phosphorylated and translocated from the cytoplasm to the nucleus in response to type I IFN. The ability to bind specific DNA sequences or the translocation of transcription factors can be measured by techniques known to those of skill in the art, e.g., electromobility gel shift assays, cell staining, etc. Other assays that can be used are described in U.S. patent application Ser. No. 09/829,711, herein incorporated by reference in its entirety. In a preferred embodiment, however, differential growth assays are used to select viruses having the desired phenotype, since the host system used (IFN-competent versus IFN-deficient) applies the appropriate selection pressure.

The attenuated swine influenza viruses of the present invention are optimally screened in pig cells, including primary, secondary pig cells and pig cell lines. Any pig cell which is capable of growing swine influenza virus can be used. Preferred pig cells include porcine kidney cell lines, porcine testis cells lines and porcine lung. Representative pig cells include, but are not limited to, PK(D1) cells, PK(15) cells, PK13 cells, NSK cells, LLC-PK1 cells, LLC-PK1A cells, ESK-4 cells, ST cells, PT-K75 cells, PK-2a/CL 13 cells or SJPL cells.

The swine influenza viruses of the invention can be screened in pig cells by comparison to wild-type swine influenza viruses, e.g., A/Swine/Texas/4199-2/98, under the same growth conditions. Attenuated swine influenza viruses are selected based on characteristics such as slower growth rates, fewer lung lesions upon infection of pigs, reduced viral titers in bronchoalveolar lavage fluid (BALF) and reduced detection of virus on nasal swabs when compared to wild-type swine influenza virus. Such attenuated swine influenza viruses have decreased virulence because they have a reduced ability to replicate in interferon competent systems compared to wild-type swine influenza viruses but can generate an immune response.

Pig cells can be infected with wild-type swine influenza viruses, e.g., A/Swine/Texas/4199-2/98, and NS1 mutants at a specific MOI and viral titers in the supernatant can be determined at specific times post-infection. Infection of pig cells at MOIs from between 0.0005 and 0.001, 0.001 and 0.01, 0.01 and 0.1, 0.1 and 1, or 1 and 10, or a MOI of 0.0005, 0.001, 0.005, 0.01, 0.05, 0.1, 0.5, 1, 5 or 10 can be used. In one embodiment, an MOI of 0.001 is used. Viral titers can be determined from approximately 2 to 10 days, 3 to 7 days, 3 to 5 days or 2, 3, 4, 5, 6, 7, 8, 9 or 10 days post-infection. In a specific embodiment, viral titers are determined 5 days post-infection. After growing virus in pig cells, viral titers can be assessed in the supernatant. Any system for measuring titers of influenza virus can be used. Representative systems are described in Section 5.7. In a particular embodiment, viral titers in the supernatant are determined by plaquing various time points on MDCK cells.

The selection systems of the invention encompass measuring IFN induction by determining whether an extract from the cell or egg infected with the test attenuated swine influenza virus is capable of conferring protective activity against viral infection. More specifically, groups of 10-day old embryonated chicken eggs are infected with the test mutant swine influenza virus or the wild-type swine influenza virus. Approximately 15 to 20 hours post infection, the allantoic fluid is harvested and tested for IFN activity by determining the highest dilution with protective activity against swine influenza virus infection in tissue culture cells.

The pathogenesis of mutant swine influenza viruses of the invention can also be assessed in pigs in vivo. Useful assays include assessing lung lesions in lung lobes, nasal swabs and determination of viral titers in bronchoalveolar lavage fluid (BALF) by any method known in the art.

5.3 Propagation of Attenuated Swine Influenza Virus

The present invention provides methods for propagating attenuated swine influenza viruses in cells (e.g., pig cells), embryonated eggs, and animals. The attenuated swine influenza viruses of the present invention can be propagated in any substrate that allows the virus to grow to titers that permit a use of the attenuated swine influenza virus described herein. In a specific embodiment, the attenuated swine influenza viruses of the present invention are propagated in any substrate that allows the virus to grow to titers comparable to those determined for wild type swine influenza virus strains in IFN-competent substrates. In another embodiment, the attenuated swine influenza viruses of the invention are propagated in IFN-deficient substrates. Substrates which are useful for selection of the attenuated swine influenza viruses of the invention do not have to be used for propagation and vice versa.

In accordance with the methods of the present invention, the attenuated swine influenza viruses which may be grown in cells (e.g., pig cells), embryonated eggs, and animals are selected from naturally occurring strains, variants or mutants, mutagenized virus, reassortants and/or genetically engineered viruses. The methods of the present invention encompass growing the attenuated swine influenza viruses, preferably using appropriate growth conditions (see e.g., growth conditions set forth in Section 6 below), and collecting the progeny virus.

In a specific embodiment, the attenuated swine influenza viruses of the invention are propagated in pig cells. In accordance with this embodiment, the pig cells may or may not be IFN-deficient or produce lower levels of IFN. Preferred pig cells include porcine kidney cell lines, porcine testis cell lines and porcine lung cell lines. Representative pig cells include, but are not limited to, PK(D1) cells, PK(15) cells, PK13 cells, SJPL cells, NSK cells, LLC-PK1 cells, LLC-PK1A cells, ESK-4 cells, ST cells, PT-K75 cells, and PK-2a/CL 13 cells. In another specific embodiment, the attenuated swine influenza viruses are propagated in chicken cells, e.g., chicken embryo fibroblasts derived from 6-day-old embryonated eggs.

In certain embodiments, the invention provides methods of propagating the attenuated swine influenza viruses of the invention in embryonated eggs, e.g., from 6 to 14 days old. In other embodiments, young or immature embryonated eggs can be used to propagate attenuated swine influenza viruses of the invention. In accordance with the present invention, immature embryonated eggs encompass eggs which are less than ten-day-old eggs, preferably six to nine day old eggs, six to eight day old, six to seven day old eggs or six days old eggs. Immature embryonated eggs of the present invention also encompass eggs which artificially mimic immature eggs up to, but less than ten-day-old, as a result of alterations to the growth conditions, e.g., changes in incubation temperatures; treating with drugs; or any other alteration which results in an egg with a retarded development, such that the IFN system is not fully developed as compared with ten- to twelve-day-old eggs. The swine influenza viruses can be propagated in different locations of the embryonated egg, e.g., the allantoic cavity. In certain embodiments, the embryonated eggs are chick eggs.

The invention also encompasses methods and IFN-deficient substrates for the growth and isolation of attenuated swine influenza viruses of the present invention. See, e.g., U.S. Pat. No. 6,573,079, which is expressly incorporated by reference in its entirety. IFN-deficient substrates which can be used to support the growth of the attenuated swine influenza viruses include, but are not limited to, naturally occurring cells, cell lines, embryonated eggs, and IFN-deficient systems, e.g., Vero cells, young embryonated eggs; recombinant cells or cell lines that are engineered to be IFN deficient, e.g., IFN-deficient cell lines derived from STAT1 knockouts, IRF3 knockouts, IRF7 knockouts, PKR knockouts, etc.; embryonated eggs obtained from IFN deficient birds, especially fowl (e.g., chickens, ducks, turkeys) including flock that are bred to be IFN-deficient or transgenic birds (e.g., STAT1 knockouts). In certain embodiments, the IFN-deficient substrate is not Vero cells and/or not a STAT1 deficient cell line.

The host system, cells, cell lines, eggs or animals can be genetically engineered to express transgenes encoding inhibitors of the IFN system, e.g., dominant-negative mutants, such as STAT1 lacking the DNA binding domain, antisense RNA, ribozymes, inhibitors of IFN production, inhibitors of IFN signaling, and/or inhibitors of antiviral genes induced by IFN. It should be recognized that animals that are bred or genetically engineered to be IFN deficient will be somewhat immunocompromised, and should be maintained in a controlled, disease free environment. Thus, appropriate measures (including the use of dietary antibiotics) should be taken to limit the risk of exposure to infectious agents of transgenic IFN deficient animals, such as mice, flocks of breeding hens, ducks, turkeys etc. Alternatively, the host system, e.g., cells, cell lines, eggs or animals can be treated with a compound which inhibits IFN production and/or the IFN pathway e.g., drugs, antibodies, antisense molecules, ribozyme molecules targeting the STAT1 gene, and/or antiviral genes induced by IFN.

The present invention encompasses methods of growing and isolating swine influenza viruses having altered IFN antagonist activity in cells and cell lines which naturally do not have an IFN pathway or have a deficient IFN pathway or have a deficiency in the IFN system e.g., low levels of IFN expression as compared to wild-type cells. In a particular embodiment, the present invention encompasses methods of growing the attenuated swine influenza viruses of the invention in chicken embryo fibroblasts derived from 6-day-old embryonated eggs, or Vero cells, or IFN-compromised embryonated eggs (e.g., immature embryonated eggs such as 6-, 7- or 8-day old embryonated eggs). In another embodiment, the present invention encompasses methods of growing the attenuated swine influenza viruses of the invention in cells where the cells are not Vero cells.

The present invention provides methods of growing and isolating the swine influenza viruses of the invention from a genetically engineered IFN deficient substrate. The present invention encompasses transgenic pigs and avians in which a gene essential to the IFN system is mutated, e.g., STAT1, which would lay eggs that are IFN deficient. The present invention further encompasses avian transgenics which express dominant-negative transcription factors, e.g., STAT1 lacking the DNA binding domain, ribozymes, antisense RNA, inhibitors of IFN production, inhibitors of IFN signaling, and inhibitors of antiviral genes induced in response to IFN.

The invention provides recombinant cell lines or animals, in particular pigs and avians, in which one or more genes essential for IFN synthesis, the IFN pathway, and/or an antiviral gene induced by IFN, e.g. interferon receptor, STAT1, PKR, IRF3, IRF7, etc. has been mutated (e.g., disrupted, i.e., is a "knockout"). The recombinant animal can be any animal (such as a mouse, a pig or an avian, e.g., chicken, turkey, hen, duck, etc. (see, e.g., Sang, 1994, Trends Biotechnol. 12:415; Perry, et al., 1993, Transgenic Res. 2:125; Stern, C. D., 1996, Curr Top Microbiol Immunol 212:195-206; and Shuman, 1991, Experientia 47:897 for reviews regarding the production of avian transgenics each of which is incorporated by reference herein in its entirety)). In a specific embodiment, the recombinant animal is a pig. Such a cell line or animal can be generated by any method known in the art for disrupting a gene on the chromosome of the cell or animal. Such techniques include, but are not limited to pronuclear microinjection (Hoppe & Wagner, 1989, U.S. Pat. No. 4,873,191); retrovirus mediated gene transfer into germ lines (Van der Putten et al., 1985, Proc. Natl. Acad. Sci., USA 82:6148-6152); gene targeting in embryonic stem cells (Thompson et al., 1989, Cell 56:313); electroporation of embryos (Lo, 1983, Mol Cell. Biol. 3:1803); and sperm-mediated gene transfer (Lavitrano et al., 1989, Cell 57:717); etc. For a review of such techniques, see Gordon, 1989, Transgenic Animals, Intl. Rev. Cytol. 115: 171, which is incorporated by reference herein in its entirety.

In particular, a STAT1 knockout animal can be produced by promoting homologous recombination between a STAT1 gene in its chromosome and an exogenous STAT1 gene that has been rendered biologically inactive (preferably by insertion of a heterologous sequence, e.g., an antibiotic resistance gene). Homologous recombination methods for disrupting genes in the mouse genome are described, for example, in Capecchi (1989, Science 244:1288) and Mansour et al. (1988, Nature 336:348-352).

Briefly, all or a portion of a STAT1 genomic clone is isolated from genomic DNA from the same species as the knock-out cell or animal. The STAT1 genomic clone can be isolated by any method known in the art for isolation of genomic clones (e.g. by probing a genomic library with a probe derived from a STAT1 sequence such as pig STAT1 (Genbank Accession Nos. AB116564 and NM 213769) and those sequences provided in see Meraz et al. 1996, Cell 84: 431-442; Durbin et al. 1996, Cell 84: 443-450, and references cited therein). Once the genomic clone is isolated, all or a portion of the clone is introduced into a recombinant vector. Preferably, the portion of the clone introduced into the vector contains at least a portion of an exon of the STAT1 gene, i.e., contains a STAT1 protein coding sequence. A sequence not homologous to the STAT1 sequence, preferably a positive selectable marker, such as a gene encoding an antibiotic resistance gene, is then introduced into the STAT1 gene exon. The selectable marker is preferably operably linked to a promoter, more preferably a constitutive promoter. The non-homologous sequence is introduced anywhere in the STAT1 coding sequence that will disrupt STAT1 activity, e.g., at a position where point mutations or other mutations have been demonstrated to inactivate STAT1 protein function. For example, but not by way of limitation, the non-homologous sequence can be inserted into the coding sequence for the portion of the STAT1 protein containing all or a portion of the kinase domain (e.g., the nucleotide sequence coding for at least 50, 100, 150, 200 or 250 amino acids of the kinase domain).

The positive selectable marker is preferably a neomycin resistance gene (neo gene) or a hygromycin resistance gene (hygro gene). The promoter may be any promoter known in the art; by way of example the promoter may be the phosphoglycerate kinase (PGK) promoter (Adra et al., 1987, Gene 60:65-74), the PolII promoter (Soriano et al., 1991, Cell 64:693-701), or the MC1 promoter, which is a synthetic promoter designed for expression in embryo-derived stem cells (Thomas & Capecchi, 1987, Cell 51:503-512). Use of a selectable marker, such as an antibiotic resistance gene, allows for the selection of cells that have incorporated the targeting vector (for example, the expression of the neo gene product confers resistance to G418, and expression of the hygro gene product confers resistance to hygromycin).

In a preferred embodiment, a negative selectable marker for a counterselection step for homologous, as opposed to non-homologous, recombination of the vector is inserted outside of the STAT1 genomic clone insert. For example, such a negative selectable marker is the HSV thymidine kinase gene (HSV-tk), the expression of which makes cells sensitive to ganciclovir. The negative selectable marker is preferably under the control of a promoter such as, but not limited to the PGK promoter, the PolII promoter or the MC1 promoter.

When homologous recombination occurs, the portions of the vector that are homologous to the STAT1 gene, as well as the non-homologous insert within the STAT1 gene sequences, are incorporated into the STAT1 gene in the chromosome, and the remainder of the vector is lost. Thus, since the negative selectable marker is outside the region of homology with the STAT1 gene, cells in which homologous recombination has occurred (or their progeny), will not contain the negative selectable marker. For example, if the negative selectable marker is the HSV-tk gene, the cells in which homologous recombination has occurred will not express thymidine kinase and will survive exposure to ganciclovir. This procedure permits the selection of cells in which homologous recombination has occurred, as compared to non-homologous recombination in which it is likely that the negative selectable marker is also incorporated into the genome along with the STAT1 sequences and the positive selectable marker. Thus, cells in which non-homologous recombination has occurred would most likely express thymidine kinase and be sensitive to ganciclovir.

Once the targeting vector is prepared, it is linearized with a restriction enzyme for which there is a unique site in the targeting vector, and the linearized vector is introduced into embryo-derived stem (ES) cells (Gossler et al., 1986, Proc. Natl. Acad. Sci. USA 83:9065-9069) by any method known in the art, for example by electroporation. If the targeting vector includes a positive selectable marker and a negative, counterselectable marker, the ES cells in which homologous recombination has occurred can be selected by incubation in selective media. For example, if the selectable markers are the neo resistance gene and the HSV-tk gene, the cells are exposed to G418 (e.g., approximately 300 µg/ml) and ganciclovir (e.g., approximately 2 µM).

Any technique known in the art for genotyping, for example but not limited to Southern blot analysis or the polymerase chain reaction, can be used to confirm that the disrupted STAT1 sequences have homologously recombined into the STAT1 gene in the genome of the ES cells. Because the restriction map of the STAT1 genomic clone is known and the sequence of the STAT1 coding sequence is known (see Meraz et al. 1996, Cell 84:431, Durbin et al. 1996, Cell 84:443-450, all references cited therein), the size of a particular restriction fragment or a PCR amplification product generated from DNA from both the disrupted and non-disrupted alleles can be determined. Thus, by assaying for a restriction fragment or PCR product, the size of which differs between the disrupted and non-disrupted STAT1 gene, one can determine whether homologous recombination has occurred to disrupt the STAT1 gene.

The ES cells with the disrupted STAT1 locus can then be introduced into blastocysts by microinjection and then the blastocysts can be implanted into the uteri of pseudopregnant mice using routine techniques. The animal that develop from the implanted blastocysts are chimeric for the disrupted allele. The chimeric males can be crossed to females, and this cross can be designed such that germline transmission of the allele is linked to transmission of a certain coat color. The germline transmission of the allele can be confirmed by Southern blotting or PCR analysis, as described above, of genomic DNA isolated from tissue samples.

Any gene whose product is important for interferon regulation can be used. Other mutations in the interferon pathway which may be used in accordance with the present invention include kinase deficient versions of Jak1, TyK2 or transcription factors lacking DNA binding domains STAT1, and STAT2 (see, e.g., Krishnan et al., 1997, Eur. J. Biochem. 247: 298-305).

For virus purification, the attenuated swine influenza virus is removed from cell culture and separated from cellular components, typically by well known clarification procedures, e.g., such as gradient centrifugation and column chromatography, and may be further isolated as desired using procedures well known to those skilled in the art, e.g., plaque assays.

5.4 Uses of Attenuated Viruses

The attenuated swine influenza viruses of the invention can be used as viral vectors for production of heterologous proteins as described in U.S. Pat. Nos. 6,635,416 and 6,635,416.

The attenuated swine influenza viruses of the invention can be used as viral vectors for production of heterologous proteins as described in U.S. Pat. No. 5,820,871, which is herein incorporated by reference in its entirety.

The attenuated swine influenza viruses of the invention can be used in screening assays to identify viral proteins with interferon antagonizing function, for identifying viral proteins that have the ability to complement replication of an attenuated virus with impaired ability to antagonize cellular interferon responses and screening assays to identify antiviral agents which inhibit interferon antagonist activity and inhibit viral replication as described in U.S. Pat. No. 6,635,416, which is herein incorporated by reference in its entirety.

The attenuated swine influenza viruses of the invention can be used to produce antibodies which can be used in diagnostic immunoassays, passive immunotherapy, and generation of antiidiotypic antibodies. For example, an attenuated swine influenza virus comprising a genome comprising a mutation in the NS1 gene and a heterologous sequence (e.g., a tumor antigen) can be administered to a subject (e.g., a pig) to generate antibodies which can then be isolated and used in diagnostic assays, passive immunotherapy and generation of antiidiotypic antibodies. The generated antibodies may be isolated by standard techniques known in the art (e.g., immunoaffinity chromatography, centrifugation, precipitation, etc.) and used in diagnostic immunoassays, passive immunotherapy and generation of antiidiotypic antibodies. The isolated antibodies before being used in passive immunotherapy may be modified, e.g., the antibodies may be chimerized or humanized. See, e.g., U.S. Pat. Nos. 4,444,887 and 4,716,111; and International Publication Nos. WO 98/46645, WO 98/50433, WO 98/24893, WO98/16654, WO 96/34096, WO 96/33735, and WO 91/10741; each of which is incorporated herein by reference in its entirety, for reviews on the generation of chimeric and humanized antibodies.

The antibodies isolated from subjects administered an attenuated swine influenza virus of the invention may also be used to monitor treatment and/or disease progression. Any immunoassay system known in the art may be used for this purpose including but not limited to competitive and noncompetitive assay systems using techniques such as radioimmunoassays, ELISA (enzyme-linked immunosorbent assays), "sandwich" immunoassays, precipitin reactions, gel diffusion precipitin reactions, immunodiffusion assays, agglutination assays, complement-fixation assays, immunoradiometric assays, fluorescent immunoassays, protein A immunoassays and immunoelectrophoresis assays, to name but a few.

The antibodies generated by the attenuated swine influenza viruses of the invention can also be used in the production of antiidiotypic antibody. The antiidiotypic antibody can then in turn be used for immunization, in order to produce a subpopulation of antibodies that bind the initial antigen of the pathogenic microorganism (Jerne, 1974, Ann. Immunol. (Paris) 125c:373; Jerne et al., 1982, EMBO J. 1:234).

In immunization procedures, the amount of immunogen to be used and the immunization schedule will be determined by a physician skilled in the art and will be administered by reference to the immune response and antibody titers of the subject.

5.5 Vaccine Formulations/Immunogenic Formulations

The invention encompasses vaccine formulations and immunogenic formulations comprising an attenuated swine influenza virus having an impaired ability to antagonize the cellular IFN response (i.e., swine influenza viruses with mutations in the NS1 gene that impair the ability of the virus to induce a cellular IFN response), and a suitable excipient. The attenuated swine influenza virus used in the vaccine formulation or immunogenic formulation may be selected from naturally occurring mutants or variants, mutagenized viruses or genetically engineered viruses. In a preferred embodiment, the attenuated swine influenza virus is genetically engineered. In another preferred embodiment, the attenuated swine influenza virus is isolated or purified. Attenuated strains of swine influenza viruses can also be generated via reassortment techniques, helper-free plasmid technology or by using a combination of the reverse genetics approach or helper-free plasmid technology and reassortment techniques. Naturally occurring variants include viruses isolated from nature as well as spontaneous occurring variants generated during virus propagation, having an impaired ability to antagonize the cellular IFN response. The attenuated swine influenza virus can itself be used as the active ingredient in the vaccine formulation or immunogenic formulation. Alternatively, the attenuated swine influenza virus can be used as the vector or "backbone" of recombinantly produced vaccines or immunogenic formulations. To this end, recombinant techniques such as reverse genetics (or, for segmented viruses, combinations of the reverse genetics and reassortment techniques) may be used to engineer mutations or introduce foreign antigens into the attenuated swine influenza virus used in the vaccine formulation or immunogenic formulation. In this way, vaccines can be designed for immunization against strain variants, or in the alternative, against completely different infectious agents or disease antigens.

Virtually any heterologous gene sequence may be constructed into the attenuated swine influenza viruses of the invention for use in vaccines or immunogenic formulations. Preferably, epitopes that induce a protective immune response to any of a variety of pathogens, or antigens that bind neutralizing antibodies may be expressed by or as part of the viruses. For example, heterologous gene sequences that can be constructed into the viruses of the invention for use in vaccines and immunogenic formulations include but are not limited to antigenic determinants of non-viral pathogens such as bacteria and parasites. In another embodiment, all or portions of immunoglobulin genes may be expressed. For example, variable regions of anti-idiotypic immunoglobulins that mimic such epitopes may be constructed into the viruses of the invention. In yet another embodiment, tumor associated antigens may be expressed. Examples of tumor antigens include, but are not limited to, KS 1/4 pan-carcinoma antigen, ovarian carcinoma antigen (CA125), prostatic acid phosphate, prostate specific antigen, melanoma-associated antigen p97, melanoma antigen gp75, high molecular weight melanoma antigen (HMW-MAA), prostate specific membrane antigen, carcinoembryonic antigen (CEA), polymorphic epithelial mucin antigen, milk fat globule antigen, colorectal tumor-associated antigens (such as: CEA, TAG-72, CO17-1A; GICA 19-9, CTA-1 and LEA), Burkitt's lymphoma antigen-38.13, CD19, B-lymphoma antigen-CD20, CD33, melanoma specific antigens (such as ganglioside GD2, ganglioside GD3, ganglioside GM2, ganglioside GM3), tumor-specific transplantation type of cell-surface antigen (TSTA) (such as virally-induced tumor antigens including T-antigen DNA tumor viruses and Envelope antigens of RNA tumor viruses), oncofetal antigen-alpha-fetoprotein such as CEA of colon, bladder tumor oncofetal antigen, differentiation antigen (such as human lung carcinoma antigen L6 and L20), antigens of fibrosarcoma, leukemia T cell antigen-Gp37, neoglycoprotein, sphingolipids, breast cancer antigens (such as EGFR (Epidermal growth factor receptor), HER2 antigen (p185$^{HER2}$) and HER2 neu epitope), polymorphic epithelial mucin (PEM), malignant human lymphocyte antigen-APO-1, differentiation antigen (such as I antigen found in fetal erythrocytes, primary endoderm, I antigen found in adult erythrocytes, preimplantation embryos, I(Ma) found in gastric adenocarcinomas, M18, M39 found in breast epithelium, SSEA-1 found in myeloid cells, VEP8, VEP9, Myl, VIM-D5, $D_1$56-22 found in colorectal cancer, TRA-1-85 (blood group H), C14 found in colonic adenocarcinoma, F3 found in lung adenocarcinoma, AH6 found in gastric cancer, Y hapten, Le$^y$ found in embryonal carcinoma cells, TL5 (blood group A), EGF receptor found in A431 cells, $E_1$ series (blood group B) found in pancreatic cancer, FC10.2 found in embryonal carcinoma cells, gastric adenocarcinoma antigen, CO-514 (blood group Le$^a$) found in Adenocarcinoma, NS-10 found in adenocarcinomas, CO-43 (blood group Le$^b$), G49 found in EGF receptor of A431 cells, MH2 (blood group ALe$^b$/Le$^y$) found in colonic adenocarcinoma, 19.9 found in colon cancer, gastric cancer mucins, $T_5A_7$ found in myeloid cells, $R_{24}$ found in melanoma, 4.2, $G_{D3}$, D1.1, OFA-1, $G_{M2}$, OFA-2, $G_{D2}$, and M1:22:25:8 found in embryonal carcinoma cells, and SSEA-3 and SSEA-4 found in 4 to 8-cell stage embryos), T cell receptor derived peptide from a Cutaneous T cell Lymphoma, C-reactive protein (CRP), cancer antigen-50 (CA-50), cancer antigen 15-3 (CA15-3) associated with breast cancer, cancer antigen-19

(CA-19) and cancer antigen-242 associated with gastrointestinal cancers, carcinoma associated antigen (CAA), chromogranin A, epithelial mucin antigen (MC5), human epithelium specific antigen (HEA), Lewis(a)antigen, melanoma antigen, melanoma associated antigens 100, 25, and 150, mucin-like carcinoma-associated antigen, multidrug resistance related protein (MRPm6), multidrug resistance related protein (MRP41), Neu oncogene protein (C-erbB-2), neuron specific enolase (NSE), P-glycoprotein (mdr1 gene product), multidrug-resistance-related antigen, p170, multidrug-resistance-related antigen, prostate specific antigen (PSA), CD56, and NCAM.

Either a live recombinant swine influenza virus vaccine or immunogenic formulation or an inactivated recombinant swine influenza virus vaccine or immunogenic formulation can be formulated. A swine influenza virus can be inactivated by methods well known to those of skill in the art. Common methods use formalin and heat for inactivation. See, e.g., U.S. Pat. No. 6,635,246, which is herein incorporated by reference in its entirety. Other methods include those described in U.S. Pat. Nos. 5,891,705; 5,106,619 and 4,693,981, which are herein incorporated by reference in their entireties.

A live vaccine or immunogenic formulation may be preferred because multiplication in the host leads to a prolonged stimulus of similar kind and magnitude to that occurring in natural infections, and therefore, confers substantial, long-lasting immunity. Production of such live recombinant swine influenza virus vaccine formulations and immunogenic formulations may be accomplished using conventional methods involving propagation of the swine influenza virus in cell culture or in the allantois of the chick embryo followed by purification. Moreover, the attenuated swine influenza viruses can induce a robust IFN response which has other biological consequences in vivo, affording protection against subsequent infectious diseases and/or inducing antitumor responses.

Vaccine formulations and immunogenic formulations may include genetically engineered swine influenza viruses that have mutations in the NS1 gene including but not limited to the truncated NS1 influenza mutants described in the working examples, infra. They may also be formulated using natural variants. When formulated as a live virus vaccine, a range of about $10^2$ to $10^8$ can be used, preferably from about $10^3$ to $10^7$, more preferably $10^4$ pfu to about $5 \times 10^6$, and most preferably from $10^4$ to $10^7$ pfu per dose should be used.

In certain embodiments, swine influenza virus contain mutations to the NS1 gene segment that may not result in an altered IFN antagonist activity or an IFN-inducing phenotype but rather result in altered viral functions and an attenuated phenotype e.g., altered inhibition of nuclear export of poly(A)-containing mRNA, altered inhibition of pre-mRNA splicing, altered inhibition of the activation of PKR by sequestering of dsRNA, altered effect on translation of viral RNA and altered inhibition of polyadenylation of host mRNA (e.g., see Krug in Textbook of Influenza, Nicholson et al. Ed. 1998, 82-92, and references cited therein).

Many methods may be used to introduce the vaccine formulations and immunogenic formulations described above, these include but are not limited to intranasal, intratracheal, oral, intradermal, intramuscular, intraperitoneal, intravenous, and subcutaneous routes. It may be preferable to introduce the swine influenza virus vaccine formulation or immunogenic formulation via the natural route of infection of the pathogen for which the vaccine is designed, or via the natural route of infection of the wild-type virus. Where a live attenuated swine influenza virus vaccine preparation or immunogenic formulation is used, it may be preferable to introduce the formulation via the natural route of infection for influenza virus. The ability of influenza virus to induce a vigorous secretory and cellular immune response can be used advantageously. For example, infection of the respiratory tract by attenuated swine influenza viruses may induce a strong secretory immune response, for example in the urogenital system, with concomitant protection against a particular disease causing agent.

In a specific embodiment, it may be desirable to administer the compositions of the invention locally to the area in need of treatment; this may be achieved by, for example, and not by way of limitation, local infusion during surgery, by injection, by means of a catheter, or by means of an implant, said implant being of a porous, non-porous, or gelatinous material, including membranes, such as sialastic membranes, or fibers. In one embodiment, administration can be by direct injection at the site (or former site) or infection.

A vaccine or immunogenic formulation of the present invention, comprising $10^2$ to $10^8$ pfu can be used, preferably from about $10^3$ to $10^7$, more preferably $10^4$ pfu to about $5 \times 10^6$ pfu of attenuated swine influenza virus with altered IFN antagonist activity, could be administered once to a subject. Alternatively, a vaccine or immunogenic formulation of the present invention, comprising $10^2$ to $10^8$ can be used, preferably from about $10^3$ to $10^7$, more preferably $10^4$ to about $5 \times 10^6$ pfu of mutant viruses with altered IFN antagonist activity, could be administered twice, three times, four times, five times, six times, seven times, eight times, nine times, or ten times to a subject with an interval of 2 to 6 months, 2 to 8 months, 2 to 10 months, or 2 to 12 months between doses. Alternatively, a vaccine or immunogenic formulation of the present invention, comprising $10^2$ to $10^8$ can be used, preferably from about $10^3$ to $10^7$, more preferably $10^4$ pfu to about $5 \times 10^6$ pfu of mutant viruses with altered IFN antagonist activity, could be administered as often as needed to a subject. In a specific embodiment, the subject is a pig.

In certain embodiments, a vaccine formulation or an immunogenic formulation of the invention does not result in complete protection from an infection (e.g., a viral infection), but results in a lower titer or reduced number of the pathogen (e.g., a virus) compared to an untreated subject. Benefits include, but are not limited to, less severity of symptoms of the infection and a reduction in the length of the disease or condition associated with a the infection In certain embodiments, the vaccine formulation or immunogenic formulation of the invention is used to protect against infections by swine influenza virus. In other embodiments, a vaccine formulation of the invention is used to protect against infection by another swine virus, including, but not limited to, porcine reproductive and respiratory syndrome virus, porcine cytomegalo virus, porcine respiratory corona virus, porcine encephalomyocarditis virus, porcine epidemic diarrhea. In yet other embodiments, the vaccine formulation or immunogenic formulation of the invention is used to protect against infections by pathogens other than a swine virus.

In certain embodiments, an immunogenic formulation of the invention is used for preventing, treating, managing or ameliorating conditions in which the induction of an immune response to a particular antigen is beneficial.

5.6 Pharmaceutical Formulations

The present invention encompasses pharmaceutical formulations comprising swine influenza viruses with altered IFN antagonist activity to be used as anti-viral agents or anti-tumor agents or as agents against IFN-treatable diseases. In one embodiment, the pharmaceutical formulations have utility as an anti-viral prophylactic and may be administered to a pig at risk of getting infected or is expected to be exposed to a virus, e.g., swine influenza virus. In another embodiment, the pharmaceutical formulations have utility as a therapeutic or prophylatic for an IFN-treatable disease and thus, can be used for treating, preventing, managing or ameliorating an IFN-treatable disorders. In a preferred embodiment, the pharmaceutical formulations have utility as a therapeutic or prophylatic for a swine IFN-treatable disease and thus, can be used for treating, preventing, managing or ameliorating a swine IFN-treatable disorders. In specific embodiments, the pharmaceutical formulations of the invention have utility as a therapeutic or prophylactic for an IFN-treatable disease and thus, can be used for treating, preventing, managing or ameliorating an IFN-treatable disorders in donkeys, zebras, camels, dogs, avians (e.g., ducks). In a preferred embodiment, the pharmaceutical formulations of the invention have utility as a therapeutic or prophylactic for an IFN-treatable disease and thus, can be used for treating, preventing, managing or ameliorating an IFN-treatable disorders in pigs.

In certain embodiments, a pharmaceutical formulation of the invention comprises a chimeric attenuated swine influenza virus comprising a heterologous sequence. The heterologous sequence can encode an epitope from a foreign or tumor antigen. A foreign antigen can be selected from another virus, a bacteria or a parasite. In one embodiment, the pharmaceutical formulations may be used to treat tumors or prevent tumor formation, e.g., in pigs who have cancer or in those who are at high risk for developing neoplasms or cancer. For example, a subject (e.g., a pig, donkey, or other animal that can be infected with swine influenza virus or in which swine influenza virus can replicate) with cancer can be treated to prevent further tumorigenesis. Alternatively, pigs who are or are expected to be exposed to carcinogens can be treated. Alternatively, pigs who are to be exposed to radiation can be treated prior to exposure and thereafter. Specific cancers that can be treated with the methods and compostions of the present invention include, but are not limited to, cancers of the uterus, mammary gland, pancreas, skin, lymph gland, vulva and testicle.

The antitumor properties of the invention can be at least partially related to their ability to induce IFN and IFN responses. Alternatively, the antitumor properties of the attenuated swine influenza viruses of the invention can be related to their ability to specifically grow in and kill tumor cells, many of which are known to have deficiencies in the IFN system. Regardless of the molecular mechanism(s) responsible for the antitumor properties, the attenuated swine influenza viruses of the invention may be used to treat tumors or to prevent tumor formation.

The present invention further encompasses the swine influenza viruses with an altered IFN-antagonist phenotype which are targeted to specific organs, tissues and/or cells in the body in order to induce therapeutic or prophylactic effects locally. One advantage of such an approach is that the IFN-inducing swine influenza viruses of the invention are targeted to specific sites, e.g. the location of a tumor, to induce IFN in a site specific manner for a therapeutic effect rather than inducing IFN systemically which may have toxic effects.

The IFN-inducing swine influenza viruses of the invention may be engineered using the methods described herein to express proteins or peptides which would target the viruses to a particular site. In a specific embodiment, the IFN-inducing swine influenza viruses would be targeted to sites of tumors. In such an embodiment, the swine influenza viruses can be engineered to express the antigen combining site of an antibody which recognizes a tumor specific antigen, thus targeting the IFN-inducing swine influenza virus to the tumor. In another embodiment, where the tumor to be targeted expresses a hormone receptor, such as breast or ovarian tumors which express estrogen receptors, the IFN-inducing swine influenza virus may be engineered to express the appropriate hormone. In yet another embodiment, where the tumor to be targeted expresses a receptor to a growth factor, e.g. VEGF, EGF, or PDGF, the IFN-inducing virus may be engineered to express the appropriate growth factor or fragment thereof. Thus, in accordance with the invention, the IFN-inducing swine influenza viruses may be engineered to express any target gene product, including peptides, proteins, such as enzymes, hormones, growth factors, antigens or antibodies, which will function to target the swine influenza virus to a site in need of treatment (e.g., anti-viral, antibacterial, anti-microbial or anti-cancer therapy).

Methods of introduction include but are not limited to intradermal, intramuscular, intraperitoneal, intravenous, subcutaneous, intranasal, epidural, and oral routes. The pharmaceutical formulations of the present invention may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, in a preferred embodiment it may be desirable to introduce the pharmaceutical formulations of the invention into the lungs by any suitable route. Pulmonary administration can also be employed, e.g., by use of an inhaler or nebulizer, and formulation with an aerosolizing agent.

In a specific embodiment, it may be desirable to administer the pharmaceutical formulations of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of a malignant tumor or neoplastic or pre-neoplastic tissue.

In another embodiment, the pharmaceutical formulation can be delivered in a biological matrix. An example of a biological matrix is described in U.S. Pat. No. 5,962,427, and U.S. Patent Application Publication U.S. 2002/0193338, herein incorporated by reference in their entireties.

In yet another embodiment, the pharmaceutical formulation can be delivered in a controlled release system. In one embodiment, a pump may be used (see Langer, supra; Sefton, 1987, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger & Peppas, 1983, J. Macromol. Sci. Rev. Macromol. Chem. 23:61; see also Levy et al., 1985, Science 228:190; During et al., 1989, Ann. Neurol. 25:351 (1989); Howard et al., 1989, J. Neurosurg. 71:105).

In yet another embodiment, a controlled release system can be placed in proximity of the composition's target, i.e., the lung, thus requiring only a fraction of the systemic dose (see, e.g., Goodson, 1984, in Medical Applications of Controlled Release, supra, vol. 2, pp. 115-138). Other controlled release systems are discussed in the review by Langer (1990, Science 249:1527-1533).

In a preferred embodiment, the pharmaceutical formulations of the present invention comprise an effective amount of an attenuated swine influenza virus of the invention, and a pharmaceutically acceptable carrier. The term "pharmaceutically acceptable" means approved by a regulatory agency of the Federal or a state government or listed in the U.S. Pharmacopeia or other generally recognized pharmacopeiae for use in animals, and more particularly in humans. The term "carrier" refers to a diluent, adjuvant, excipient, or vehicle with which the pharmaceutical formulation is administered. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. These compositions can take the form of solutions, suspensions, emulsion, tablets, pills, capsules, powders, sustained-release formulations and the like. The composition can be formulated as a suppository. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain an effective amount of the therapy, preferably in purified form, together with a suitable amount of carrier so as to provide the form for proper administration to the patient. The formulation should suit the mode of administration. The particular formulation may also depend on whether swine influenza virus is live or inactivated.

The amount of the pharmaceutical formulation of the invention which will be effective in the treatment, prevention, management, or amelioration of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. However, suitable dosage ranges for administration are generally about $10^2$, $5 \times 10^2$, $10^3$, $5 \times 10^3$, $10^4$, $5 \times 10^4$, $10^5$, $5 \times 10^5$, $10^6$, $5 \times 10^6$, $10^7$, $5 \times 10^7$, $10^8$, $5 \times 10^8$, $1 \times 10^9$, $5 \times 10^9$, $1 \times 10^{10}$, $5 \times 10^{10}$, $1 \times 10^{11}$, $5 \times 10^{11}$ or $10^{12}$ pfu, and most preferably about $10^4$ to about $10^{12}$ pfu, and can be administered to a subject once, twice, three or more times with intervals as often as needed. Pharmaceutical formulations of the present invention comprising $10^2$, $5 \times 10^2$, $10^3$, $5 \times 10^3$, $10^4$, $5 \times 10^4$, $10^5$, $5 \times 10^5$, $10^6$, $5 \times 10^6$, $10^7$, $5 \times 10^7$, $10^8$, $5 \times 10^8$, $1 \times 10^9$, $5 \times 10^9$, $1 \times 10^{10}$, $5 \times 10^{10}$, $1 \times 10^{11}$, $5 \times 10^{11}$ or $10^{12}$ pfu, and most preferably about $10^4$ to about $10^{12}$ pfu of an attenuated swine influenza virus with altered IFN antagonist activity, can be administered to a subject intranasally, intratracheally, intramuscularly or subcutaneously Effective doses may be extrapolated from dose-response curves derived from in vitro or animal model test systems.

In certain embodiments, the pharmaceutical formulation of the invention is used to prevent, manage, treat or ameliorate infections by viruses, bacteria or parasites. In other embodiments, the pharmaceutical formulation of the invention is used to prevent, manage, treat or ameliorate cancer in a pig. In other embodiments, the pharmaceutical formulation of the invention is used to prevent, manage, treat or ameliorate other IFN-treatable diseases.

5.7 Therapies Useful in Combination with Swine Influenza Virus

The present invention also provides methods for preventing, managing, treating, and/or ameliorating diseases and disorders including, but not limited to, swine influenza virus infections, conditions associated with swine influenza virus infection, infections other than swine influenza virus infections, conditions associated with infections other than swine influenza virus infections, IFN-treatable disorders (e.g., cancer) and conditions in which an attenuated swine influenza virus of the invention is used as a vector to induce an immune response to an antigen associated with the condition comprising administering to a subject in need thereof an effective amount of one or more attenuated swine influenza viruses of the present invention and an effective amount of one or more therapies (e.g., prophylactic or therapeutic agents) other than attenuated swine influenza viruses. Therapies include, but are not limited to, small molecules, synthetic drugs, peptides, polypeptides, proteins, nucleic acids (e.g., DNA and RNA nucleotides including, but not limited to, antisense nucleotide sequences, triple helices, RNAi, and nucleotide sequences encoding biologically active proteins, polypeptides or peptides) antibodies, synthetic or natural inorganic molecules, mimetic agents, and synthetic or natural organic molecules.

Any therapy (e.g., prophylactic or therapeutic agents) which is known to be useful, or which has been used or is currently being used for the prevention, management, treatment, or amelioration of a swine influenza virus infection, infections other than swine influenza virus infections, conditions associated with infections other than swine influenza virus infections, IFN-treatable disorders, conditions in which an attenuated swine influenza virus of the invention is used as a vector to induce an immune response to an antigen associated with the condition, or any other pig disease can be used in combination with an attenuated swine influenza virus in accordance with the invention described herein. See, e.g., Taylor, *Pig Diseases,* 6$^{th}$ Ed., Diamond Farm Book Pubns, 1995; Straw et al., *Diseases of Swine,* 8$^{th}$ Ed., Iowa State University Press, 1999, for information regarding therapies, in particular prophylactic or therapeutic agents, which have been or are currently being used for preventing, treating, managing, and/or ameliorating pig diseases. Examples of prophylactic and therapeutic agents include, but are not limited to, anti-cancer agents; anti-viral agents, anti-inflammatory agents (e.g., adrenocorticoids, corticosteroids (e.g., beclomethasone, budesonide, flunisolide, fluticasone, triamcinolone, methylprednisolone, prednisolone, prednisone, hydrocortisone)) and antibiotics (e.g., dactinomycin (formerly actinomycin), bleomycin, erythromycin, penicillin, mithramycin, and anthramycin (AMC)).

5.7.1 Anti-Cancer Therapies

Any therapy (e.g., therapeutic or prophylactic agent) which is known to be useful, has been used, or is currently being used for the prevention, treatment, management, or amelioration of cancer or one or more symptoms thereof can be used in compositions and method of the invention. Therapies (e.g., therapeutic or prophylactic agents) include, but are not limited to, peptides, polypeptides, fusion proteins, nucleic acid molecules, small molecules, mimetic agents, synthetic drugs, inorganic molecules, and organic molecules. Non-limiting examples of cancer therapies include chemotherapies, radiation therapies, hormonal therapies, and/or biological therapies/immunotherapies.

In particular embodiments, the anti-cancer agent may be, but is not limited to: a chemotherapeutic agent (e.g., acivicin, aclarubicin, acodazole hydrochloride, acronine, adozelesin, aldesleukin, altretamine, ambomycin, ametantrone acetate, aminoglutethimide, amsacrine, anastrozole, anthramycin, asparaginase, azacitidine, azetepa, batimastat, bleomycin, benzodepa, bicalutamide, bisantrene hydrochloride, bisnafide dimesylate, bizelesin, bleomycin sulfate, brequinar sodium, bropirimine, busulfan, cactinomycin, calusterone, campathecin, caracemide, carbetimer, carboplatin, carmustine, carubicin hydrochloride, carzelesin, cedefingol, chlorambucil, cirolemycin, cisplatin, cladribine, crisnatol mesylate, cyclophosphamide, cytarabine, cyclosporin A, combretastatin A4, combretastatin analogue, cytolytic factor, cytostatin, dacliximab, docetaxel, dacarbazine, dactinomycin, daunorubicin hydrochloride, docetaxel, doxorubicin, droloxifene, dromostanolone propionate, duazomycin, edatrexate, eflornithine hydrochloride, elsamitrucin, enloplatin, enpromate, epipropidine, epirubicin hydrochloride, erbulozole, esorubicin hydrochloride, estramustine, etanidazole, etoposide, fazarabine, fenretinide, floxuridine, fluorouracil, flurocitabine, fosquidone, gemcitabine, hydroxyurea, idarubicin, idarubicin hydrochloride, ifosfamide, ilmofosine, iproplatin, ifosfamide, irinotecan hydrochloride, lanreotide acetate, letrozole, leuprolide acetate, liarozole hydrochloride, lometrexol sodium, lomustine, losoxantrone hydrochloride, masoprocol, mercaptopurine, methotrexate, metoprine, meturedepa, mitindomide, mitocarcin, mitocromin, mitomycin, mitoxantrone, mycophenolic acid, nitrosoureas, nocodazole, nogalamycin, ormaplatin, oxisuran, paclitaxel, plicamycin, platinum complex, platinum compounds, platinum-triamine complex, procarbizine, puromycin, taxol, thioguanine, talisomycin, tecogalan sodium, tegafur, teloxantrone hydrochloride, vapreotide, verteporfin, vinblastine sulfate, vincristine sulfate, vindesine, vindesine sulfate, vinepidine sulfate, vinglycinate sulfate, vinleurosine sulfate, vinorelbine tartrate, vinrosidine sulfate, vinzolidine sulfate, vorozole, zeniplatin, and zinostatin), matrix metalloproteinase inhibitors, tyrosine kinase inhibitors, tyrphostins, urokinase receptor antagonists, multiple drug resistance gene inhibitor, multiple tumor suppressor 1-based therapy, plasminogen activator inhibitor, bisphosphonates (e.g., pamidronate (Aredria), sodium clondronate (Bonefos), zoledronic acid (Zometa), alendronate (Fosamax), etidronate, ibandornate, cimadronate, risedromate, and tiludromate), a cytokine (e.g., IL-2, IFN-α, IFN-β, IFN-γ, leukemia inhibiting factor, leukocyte alpha interferon, human chorionic gonadotrophin, and thrombopoietin), a hormone (e.g., thyroid stimulating hormone), an antibody (e.g., an anti-CD2 antibody, an anti-CD20 antibody, and an antibody immunospecific for one or more galanin receptors), vitamin D (e.g., 20-epi-1,25 dihydroxyvitamin D3), an angiogenesis inhibitor, an antisense oligonucleotide, an apoptosis gene modulator, an apoptosis regulator, a BCR/ABL antagonist, a cartilage derived inhibitor, an estrogen agonist, an estrogen antagonist, a gelatinase inhibitor, a glutathione inhibitor, an HMG CoA reductase inhibitor (e.g., atorvastatin, cerivastatin, fluvastatin, lescol, lupitor, lovastatin, rosuvastatin, and simvastatin), an immunostimulant peptide, an insulin-like growth factor-1 receptor inhibitor, an interferon agonist, leuprolide+estrogen+progesterone, leuprorelin, a mismatched double stranded RNA, a proteasome inhibitor, a protein A-based immune modulator, a protein kinase C inhibitor, a protein tyrosine phosphatase inhibitor, a raf antagonist, a ras farnesyl protein transferase inhibitor, a ribozyme, RNAi, a signal transduction modulator, a stem cell inhibitor, a stem-cell division inhibitor, a telomerase inhibitor, a thymopoietin receptor agonist, and a translation inhibitor.

In specific embodiments, radiation therapy comprising the use of x-rays, gamma rays and other sources of radiation to destroy the cancer cells is used in combination with the attenuated swine influenza viruses of the invention. In preferred embodiments, the radiation treatment is administered as external beam radiation or teletherapy, wherein the radiation is directed from a remote source. In other preferred embodiments, the radiation treatment is administered as internal therapy or brachytherapy wherein a radioactive source is placed inside the body close to cancer cells or a tumor mass.

Cancer therapies and their dosages, routes of administration and recommended usage are known in the art and have been described in such literature as the *Physicians' Desk Reference* (58th ed., 2004) and Merck Veterinary Manual (8th ed., 1998).

5.7.2 Anti-Angiogenesis Therapies

Any anti-angiogenic agent well-known to one of skill in the art can be used in the compositions and methods of the invention. Non-limiting examples of anti-angiogenic agents include proteins, polypeptides, peptides, fusion proteins, antibodies (e.g., chimeric, monoclonal, polyclonal, Fvs, ScFvs, Fab fragments, $F(ab)_2$ fragments, and antigen-binding fragments thereof) such as antibodies that immunospecifically bind to TNFα, nucleic acid molecules (e.g., antisense molecules or triple helices), organic molecules, inorganic molecules, and small molecules that reduce or inhibit or neutralizes the angiogenesis. In particular, examples of anti-angiogenic agents, include, but are not limited to, endostatin, angiostatin, apomigren, anti-angiogenic antithrombin III, the 29 kDa N-terminal and a 40 kDa C-terminal proteolytic fragments of fibronectin, a uPA receptor antagonist, the 16 kDa proteolytic fragment of prolactin, the 7.8 kDa proteolytic fragment of platelet factor-4, the anti-angiogenic 24 amino acid fragment of platelet factor-4, the anti-angiogenic factor designated 13.40, the anti-angiogenic 22 amino acid peptide fragment of thrombospondin I, the anti-angiogenic 20 amino acid peptide fragment of SPARC, RGD and NGR containing peptides, the small anti-angiogenic peptides of laminin, fibronectin, procollagen and EGF, integrin $\alpha_v\beta_3$ antagonists (e.g., anti-integrin $\alpha_v\beta_3$ antibodies), acid fibroblast growth factor (aFGF) antagonists, basic fibroblast growth factor (bFGF) antagonists, vascular endothelial growth factor (VEGF) antagonists (e.g., anti-VEGF antibodies), and VEGF receptor (VEGFR) antagonists (e.g., anti-VEGFR antibodies).

5.7.3 Anti-Viral Therapies

Any anti-viral agent well-known to one of skill in the art can be used in the compositions and the methods of the invention. Non-limiting examples of anti-viral agents include proteins, polypeptides, peptides, fusion proteins antibodies, nucleic acid molecules, organic molecules, inorganic molecules, and small molecules that inhibit and/or reduce the attachment of a virus to its receptor, the internalization of a virus into a cell, the replication of a virus, or release of virus from a cell. In particular, anti-viral agents include, but are not limited to, nucleoside analogs (e.g., zidovudine, acyclovir, gangcyclovir, vidarabine, idoxuridine, trifluridine, and ribavirin), foscarnet, amantadine, rimantadine, saquinavir, indinavir, ritonavir, alpha-interferons and other interferons, and AZT.

In specific embodiments, the anti-viral agent is an immunomodulatory agent that is immunospecific for a viral antigen. As used herein, the term "viral antigen" includes, but is not limited to, any viral peptide, polypeptide and protein (e.g., 3AB, 3ABC of foot-and-mouth disease virus, GP5 of porcine reproductive and respiratory syndrome virus, pseudorabies virus gE, swine transmissible gastroenteritis virus nucleoprotein, influenza virus neuraminidase, influenza virus hemagglutinin, herpes simplex virus glycoprotein (e.g., gB, gC, gD, and gE) and hepatitis B surface antigen) that is capable of eliciting an immune response. Antibodies useful in this invention for treatment of a viral infectious disease include, but are not limited to, antibodies against antigens of pathogenic viruses, including as examples and not by limitation: adenovirdiae (e.g., mastadenovirus and aviadenovirus), herpesviridae (e.g., herpes simplex virus 1, herpes simplex virus 2, herpes simplex virus 5, and herpes simplex virus 6), leviviridae (e.g., levivirus, enterobacteria phase MS2, allolevirus), poxviridae (e.g., chordopoxvirinae, parapoxvirus, avipoxvirus, capripoxvirus, leporiipoxvirus, suipoxvirus, molluscipoxvirus, and entomopoxvirinae), papovaviridae (e.g., polyomavirus and papillomavirus), paramyxoviridae (e.g., paramyxovirus, parainfluenza virus 1, mobillivirus (e.g., measles virus), rubulavirus (e.g., mumps virus), pneumovirinae (e.g., pneumovirus, human respiratory synctial virus), and metapneumovirus (e.g., avian pneumovirus and human metapneumovirus)), picornaviridae (e.g., enterovirus, rhinovirus, hepatovirus (e.g., human hepatits A virus), cardiovirus, and apthovirus), reoviridae (e.g., orthoreovirus, orbivirus, rotavirus, cypovirus, fijivirus, phytoreovirus, and oryzavirus), retroviridae (e.g., mammalian type B retroviruses, mammalian type C retroviruses, avian type C retroviruses, type D retrovirus group, BLV-HTLV retroviruses, lentivirus (e.g., human immunodeficiency virus 1 and human immunodeficiency virus 2), spumavirus), flaviviridae (e.g., hepatitis C virus), hepadnaviridae (e.g., hepatitis B virus), togaviridae (e.g., alphavirus (e.g., sindbis virus) and rubivirus (e.g., rubella virus)), rhabdoviridae (e.g., vesiculovirus, lyssavirus, ephemerovirus, cytorhabdovirus, and necleorhabdovirus), arenaviridae (e.g., arenavirus, lymphocytic choriomeningitis virus, Ippy virus, and lassa virus), and coronaviridae (e.g., coronavirus and torovirus).

Specific examples of antibodies available useful for the treatment of a viral infectious disease include, but are not limited to, PRO542 (Progenics) which is a CD4 fusion antibody useful for the treatment of HIV infection; Ostavir (Protein Design Labs, Inc., CA) which is a human antibody useful for the treatment of hepatitis B virus; and Protovir (Protein Design Labs, Inc., CA) which is a humanized IgG1 antibody useful for the treatment of cytomegalovirus (CMV).

Anti-viral therapies and their dosages, routes of administration and recommended usage are known in the art and have been described in such literature as the *Physicians' Desk Reference* (58th ed., 2004) and Merck Veterinary Manual (8th ed., 1998). Additional information on viral infections is available in *Cecil Textbook of Medicine* (18th ed., 1988).

5.7.4 Antibiotic Therapies

Any antibiotic agent well-known to one of skill in the art can be used in the compositions and the methods of the invention. Antibacterial agents or antibiotics that can be used in combination with the complexes of the invention include but are not limited to: aminoglycoside antibiotics (e.g., apramycin, arbekacin, bambermycins, butirosin, dibekacin, neomycin, neomycin, undecylenate, netilmicin, paromomycin, ribostamycin, sisomicin, and spectinomycin), amphenicol antibiotics (e.g., azidamfenicol, chloramphenicol, florfenicol, and thiamphenicol), ansamycin antibiotics (e.g., rifamide and rifampin), carbacephems (e.g., loracarbef), carbapenems (e.g., biapenem and imipenem), cephalosporins (e.g., cefaclor, cefadroxil, cefamandole, cefatrizine, cefazedone, cefozopran, cefpimizole, cefpiramide, and cefpirome), cephamycins (e.g., cefbuperazone, cefmetazole, and cefminox), monobactams (e.g., aztreonam, carumonam, and tigemonam), oxacephems (e.g., flomoxef, and moxalactam), penicillins (e.g., amdinocillin, amdinocillin pivoxil, amoxicillin, bacampicillin, benzylpenicillinic acid, benzylpenicillin sodium, epicillin, fenbenicillin, floxacillin, penamccillin, penethamate hydriodide, penicillin o-benethamine, penicillin 0, penicillin V, penicillin V benzathine, penicillin V hydrabamine, penimepicycline, and phencihicillin potassium), lincosamides (e.g., clindamycin, and lincomycin), macrolides (e.g., azithromycin, carbomycin, clarithomycin, dirithromycin, erythromycin, and erythromycin acistrate), amphomycin, bacitracin, capreomycin, colistin, enduracidin, enviomycin, tetracyclines (e.g., apicycline, chlortetracycline, clomocycline, and demeclocycline), 2,4-diaminopyrimidines (e.g., brodimoprim), nitrofurans (e.g., furaltadone, and furazolium chloride), quinolones and analogs thereof (e.g., cinoxacin, ciprofloxacin, clinafloxacin, flumequine, and grepagloxacin), sulfonamides (e.g., acetyl sulfamethoxypyrazine, benzylsulfamide, noprylsulfamide, phthalylsulfacetamide, sulfachrysoidine, and sulfacytine), sulfones (e.g., diathymosulfone, glucosulfone sodium, and solasulfone), cycloserine, mupirocin and tuberin.

Additional examples of antibacterial agents include but are not limited to Acedapsone; Acetosulfone Sodium; Alamecin; Alexidine; Amdinocillin; Amdinocillin Pivoxil; Amicycline; Amifloxacin; Amifloxacin Mesylate; Amikacin; Amikacin Sulfate; Aminosalicylic acid; Aminosalicylate sodium; Amoxicillin; Amphomycin; Ampicillin; Ampicillin Sodium; Apalcillin Sodium; Apramycin; Aspartocin; Astromicin Sulfate; Avilamycin; Avoparcin; Azithromycin; Azlocillin; Azlocillin Sodium; Bacampicillin Hydrochloride; Bacitracin; Bacitracin Methylene Disalicylate; Bacitracin Zinc; Bambermycins; Benzoylpas Calcium; Berythromycin; Betamicin Sulfate; Biapenem; Biniramycin; Biphenamine Hydrochloride; Bispyrithione Magsulfex; Butikacin; Butirosin Sulfate; Capreomycin Sulfate; Carbadox; Carbenicillin Disodium; Carbenicillin Indanyl Sodium; Carbenicillin Phenyl Sodium; Carbenicillin Potassium; Carumonam Sodium; Cefaclor; Cefadroxil; Cefamandole; Cefamandole Nafate; Cefamandole Sodium; Cefaparole; Cefatrizine; Cefazaflur Sodium; Cefazolin; Cefazolin Sodium; Cefbuperazone; Cefdinir; Cefepime; Cefepime Hydrochloride; Cefetecol; Cefixime; Cefmnenoxime Hydrochloride; Cefinetazole; Cefinetazole Sodium; Cefonicid Monosodium; Cefonicid Sodium; Cefoperazone Sodium; Ceforanide; Cefotaxime Sodium; Cefotetan; Cefotetan Disodium; Cefotiam Hydrochloride; Cefoxitin; Cefoxitin Sodium; Cefpimizole; Cefpimizole Sodium; Cefpiramide; Cefpiramide Sodium; Cefpirome Sulfate; Cefpodoxime Proxetil; Cefprozil; Cefroxadine; Cefsulodin Sodium; Ceftazidime; Ceftibuten; Ceftizoxime Sodium; Ceftriaxone Sodium; Cefuroxime; Cefuroxime Axetil; Cefuroxime Pivoxetil; Cefuroxime Sodium; Cephacetrile Sodium; Cephalexin; Cephalexin Hydrochloride; Cephaloglycin; Cephaloridine; Cephalothin Sodium; Cephapirin Sodium; Cephradine; Cetocycline Hydrochloride; Cetophenicol; Chloramphenicol; Chloramphenicol Palmitate; Chloramphenicol Pantothenate Complex; Chloramphenicol Sodium Succinate; Chlorhexidine Phosphanilate; Chloroxylenol; Chlortetracycline Bisulfate;

Chlortetracycline Hydrochloride; Cinoxacin; Ciprofloxacin; Ciprofloxacin Hydrochloride; Cirolemycin; Clarithromycin; Clinafloxacin Hydrochloride; Clindamycin; Clindamycin Hydrochloride; Clindamycin Palmitate Hydrochloride; Clindamycin Phosphate; Clofazimine; Cloxacillin Benzathine; Cloxacillin Sodium; Cloxyquin; Colistimethate Sodium; Colistin Sulfate; Coumermycin; Coumermycin Sodium; Cyclacillin; Cycloserine; Dalfopristin; Dapsone; Daptomycin; Demeclocycline; Demeclocycline Hydrochloride; Demecycline; Denofungin; Diaveridine; Dicloxacillin; Dicloxacillin Sodium; Dihydrostreptomycin Sulfate; Dipyrithione; Dirithromycin; Doxycycline; Doxycycline Calcium; Doxycycline Fosfatex; Doxycycline Hyclate; Droxacin Sodium; Enoxacin; Epicillin; Epitetracycline Hydrochloride; Erythromycin; Erythromycin Acistrate; Erythromycin Estolate; Erythromycin Ethylsuccinate; Erythromycin Gluceptate; Erythromycin Lactobionate; Erythromycin Propionate; Erythromycin Stearate; Ethambutol Hydrochloride; Ethionamide; Fleroxacin; Floxacillin; Fludalanine; Flumequine; Fosfomycin; Fosfomycin Tromethamine; Fumoxicillin; Furazolium Chloride; Furazolium Tartrate; Fusidate Sodium; Fusidic Acid; Gentamicin Sulfate; Gloximonam; Gramicidin; Haloprogin; Hetacillin; Hetacillin Potassium; Hexedine; Ibafloxacin; Imipenem; Isoconazole; Isepamicin; Isoniazid; Josamycin; Kanamycin Sulfate; Kitasamycin; Levofuraltadone; Levopropylcillin Potassium; Lexithromycin; Lincomycin; Lincomycin Hydrochloride; Lomefloxacin; Lomefloxacin Hydrochloride; Lomefloxacin Mesylate; Loracarbef; Mafenide; Meclocycline; Meclocycline Sulfosalicylate; Megalomicin Potassium Phosphate; Mequidox; Meropenem; Methacycline; Methacycline Hydrochloride; Methenamine; Methenamine Hippurate; Methenamine Mandelate; Methicillin Sodium; Metioprim; Metronidazole Hydrochloride; Metronidazole Phosphate; Mezlocillin; Mezlocillin Sodium; Minocycline; Minocycline Hydrochloride; Mirincamycin Hydrochloride; Monensin; Monensin Sodium; Nafcillin Sodium; Nalidixate Sodium; Nalidixic Acid; Natamycin; Nebramycin; Neomycin Palmitate; Neomycin Sulfate; Neomycin Undecylenate; Netilmicin Sulfate; Neutramycin; Nifuradene; Nifuraldezone; Nifuratel; Nifuratrone; Nifurdazil; Nifurimide; Nifurpirinol; Nifurquinazol; Nifurthiazole; Nitrocycline; Nitrofurantoin; Nitromide; Norfloxacin; Novobiocin Sodium; Ofloxacin; Ormetoprim; Oxacillin Sodium; Oximonam; Oximonam Sodium; Oxolinic Acid; Oxytetracycline; Oxytetracycline Calcium; Oxytetracycline Hydrochloride; Paldimycin; Parachlorophenol; Paulomycin; Pefloxacin; Pefloxacin Mesylate; Penamecillin; Penicillin G Benzathine; Penicillin G Potassium; Penicillin G Procaine; Penicillin G Sodium; Penicillin V; Penicillin V Benzathine; Penicillin V Hydrabamine; Penicillin V Potassium; Pentizidone Sodium; Phenyl Aminosalicylate; Piperacillin Sodium; Pirbenicillin Sodium; Piridicillin Sodium; Pirlimycin Hydrochloride; Pivampicillin Hydrochloride; Pivampicillin Pamoate; Pivampicillin Probenate; Polymyxin B Sulfate; Porfiromycin; Propikacin; Pyrazinamide; Pyrithione Zinc; Quindecamine Acetate; Quinupristin; Racephenicol; Ramoplanin; Ranimycin; Relomycin; Repromicin; Rifabutin; Rifametane; Rifamexil; Rifamide; Rifampin; Rifapentine; Rifaximin; Rolitetracycline; Rolitetracycline Nitrate; Rosaramicin; Rosaramicin Butyrate; Rosaramicin Propionate; Rosaramicin Sodium Phosphate; Rosaramicin Stearate; Rosoxacin; Roxarsone; Roxithromycin; Sancycline; Sanfetrinem Sodium; Sarmoxicillin; Sarpicillin; Scopafungin; Sisomicin; Sisomicin Sulfate; Sparfloxacin; Spectinomycin Hydrochloride; Spiramycin; Stallimycin Hydrochloride; Steffimycin; Streptomycin Sulfate; Streptonicozid; Sulfabenz; Sulfabenzamide; Sulfacetamide; Sulfacetamide Sodium; Sulfacytine; Sulfadiazine; Sulfadiazine Sodium; Sulfadoxine; Sulfalene; Sulfamerazine; Sulfameter; Sulfamethazine; Sulfamethizole; Sulfamethoxazole; Sulfamonomethoxine; Sulfamoxole; Sulfanilate Zinc; Sulfanitran; Sulfasalazine; Sulfasomizole; Sulfathiazole; Sulfazamet; Sulfisoxazole; Sulfisoxazole Acetyl; Sulfisoxazole Diolamine; Sulfomyxin; Sulopenem; Sultamicillin; Suncillin Sodium; Talampicillin Hydrochloride; Teicoplanin; Temafloxacin Hydrochloride; Temocillin; Tetracycline; Tetracycline Hydrochloride; Tetracycline Phosphate Complex; Tetroxoprim; Thiamphenicol; Thiphencillin Potassium; Ticarcillin Cresyl Sodium; Ticarcillin Disodium; Ticarcillin Monosodium; Ticlatone; Tiodonium Chloride; Tobramycin; Tobramycin Sulfate; Tosufloxacin; Trimethoprim; Trimethoprim Sulfate; Trisulfapyrimidines; Troleandomycin; Trospectomycin Sulfate; Tyrothricin; Vancomycin; Vancomycin Hydrochloride; Virginiamycin; Zorbamycin.

Antibiotic therapies and their dosages, routes of administration and recommended usage are known in the art and have been described in such literature as the *Physicians' Desk Reference* (58th ed., 2004) and Merck Veterinary Manual (8th ed., 1998).

5.7.5 Immunomodulatory Therapies

Any immunomodulatory agent well-known to one of skill in the art may be used in the methods and compositions of the invention. Immunomodulatory agents can affect one or more or all aspects of the immune response in a subject. Aspects of the immune response include, but are not limited to, the inflammatory response, the complement cascade, leukocyte and lymphocyte differentiation, proliferation, and/or effector function, monocyte and/or basophil counts, and the cellular communication among cells of the immune system. In certain embodiments of the invention, an immunomodulatory agent modulates one aspect of the immune response. In other embodiments, an immunomodulatory agent modulates more than one aspect of the immune response. In a preferred embodiment of the invention, the administration of an immunomodulatory agent to a subject inhibits or reduces one or more aspects of the subject's immune response capabilities. In certain embodiments, an immunomodulatory agent is not an anti-inflammatory agent. In certain embodiments, an immunomodulatory agent is not an anti-angiogneic agent. In certain embodiments, an immunomodulatory agent is a chemotherapeutic agent. In certain embodiments, an immunomodulatory agent is not a chemotherapeutic agent.

Examples of immunomodulatory agents include, but are not limited to, proteinaceous agents such as cytokines, peptide mimetics, and antibodies (e.g., human, humanized, chimeric, monoclonal, polyclonal, Fvs, ScFvs, Fab or F(ab)2 fragments or epitope binding fragments), nucleic acid molecules (e.g., antisense nucleic acid molecules and triple helices), small molecules, organic compounds, and inorganic compounds. In particular, immunomodulatory agents include, but are not limited to, methotrexate, leflunomide, cyclophosphamide, cytoxan, Immuran, cyclosporine A, minocycline, azathioprine, antibiotics (e.g., FK506 (tacrolimus)), methylprednisolone (MP), corticosteroids, steroids, mycophenolate mofetil, rapamycin (sirolimus), mizoribine, deoxyspergualin, brequinar, malononitriloamindes (e.g., leflunamide), T cell receptor modulators, and cytokine receptor modulators.

Examples of T cell receptor modulators include, but are not limited to, anti-T cell receptor antibodies (e.g., anti-CD4 antibodies (e.g., cM-T412 (Boeringer), IDEC-CE9.1®

(IDEC and SKB), mAB 4162W94, Orthoclone and OKTcdr4a (Janssen-Cilag)), anti-CD2 antibodies, anti-CD3 antibodies (e.g., Nuvion (Product Design Labs), OKT3 (Johnson & Johnson), or Rituxan (IDEC)), anti-CD5 antibodies (e.g., an anti-CD5 ricin-linked immunoconjugate), anti-CD7 antibodies (e.g., CHH-380 (Novartis)), anti-CD8 antibodies, anti-CD40 ligand monoclonal antibodies (e.g., IDEC-131 (IDEC)), anti-CD52 antibodies (e.g., CAMPATH 1H (Ilex)), anti-CD2 antibodies, anti-CD11a antibodies (e.g., Xanelim (Genentech)), and anti-B7 antibodies (e.g., IDEC-114) (IDEC))), CTLA4-immunoglobulin, and LFA-3TIP (Biogen, International Publication No. WO 93/08656 and U.S. Pat. No. 6,162,432).

Examples of cytokine receptor modulators include, but are not limited to, soluble cytokine receptors (e.g., the extracellular domain of a TNF-α receptor or a fragment thereof, the extracellular domain of an IL-1β receptor or a fragment thereof, and the extracellular domain of an IL-6 receptor or a fragment thereof), cytokines or fragments thereof (e.g., interleukin IL-2, IL-3, IL-4, IL-5, IL-6, IL-7, IL-8, IL-9, IL-10, IL-11, IL-12, IL-13, IL-15, IL-23, TNF-α, TNF-β, interferon (IFN)-α, IFN-β, IFN-γ, and GM-CSF), anti-cytokine receptor antibodies (e.g., anti-IFN receptor antibodies, anti-IL-2 receptor antibodies (e.g., Zenapax (Protein Design Labs)), anti-IL-3 receptor antibodies, anti-IL-4 receptor antibodies, anti-IL-6 receptor antibodies, anti-IL-9 receptor antibodies anti-IL-10 receptor antibodies, anti-IL-12 receptor antibodies, anti-IL-13 receptor antibodies, anti-IL-15 receptor antibodies, and anti-IL-23 receptor antibodies), anti-cytokine antibodies (e.g., anti-IFN antibodies, anti-TNF-α antibodies, anti-IL-1β antibodies, anti-IL-3 antibodies, anti-IL-6 antibodies, anti-IL-8 antibodies (e.g., ABX-IL-8 (Abgenix)), anti-IL-9 antibodies anti-IL-12 antibodies, anti-IL-13 antibodies, anti-IL-15 antibodies, and anti-IL-23 antibodies).

In a specific embodiment, a cytokine receptor modulator is IL-3, IL-4, IL-10, or a fragment thereof. In another embodiment, a cytokine receptor modulator is an anti-IL-1β antibody, anti-IL-6 antibody, anti-IL-12 receptor antibody, or anti-TNF-α antibody. In another embodiment, a cytokine receptor modulator is the extracellular domain of a TNF-α receptor or a fragment thereof.

In certain embodiments, an immunomodulatory agent is a B cell receptor modulator. Examples of B cell receptor modulators include, but are not limited to, CD19. Targeting B cell receptors provides one means for modulating B cells.

In a preferred embodiment, proteins, polypeptides or peptides (including antibodies) that are utilized as immunomodulatory agents are derived from the same species as the recipient of the proteins, polypeptides or peptides so as to reduce the likelihood of an immune response to those proteins, polypeptides or peptides. In another preferred embodiment, when the subject is a pig, the proteins, polypeptides, or peptides that are utilized as immunomodulatory agents are derived from pig.

In accordance with the invention, one or more immunomodulatory agents are administered to a subject prior to, subsequent to, or concomitantly with an attenuated swine influenza virus. Any technique well-known to one skilled in the art can be used to measure one or more aspects of the immune response in a particular subject, and thereby determine when it is necessary to administer an immunomodulatory agent to said subject. In a preferred embodiment, a mean absolute lymphocyte count of approximately 500 cells/mm$^3$, preferably 600 cells/mm$^3$, 650 cells/mm$^3$, 700 cells/mm$^3$, 750 cells/mm$^3$, 800 cells/mm$^3$, 900 cells/mm$^3$, 1000 cells/mm$^3$, 1100 cells/mm$^3$, or 1200 cells/mm$^3$ is maintained in a subject.

Preferably, agents that are commercially available and known to function as immunomodulatory agents are used in accordance with the methods of the invention. The immunomodulatory activity of an agent can be determined in vitro and/or in vivo by any technique well-known to one skilled in the art, including, e.g., by CTL assays, proliferation assays, and immunoassays (e.g. ELISAs) for the expression of particular proteins such as co-stimulatory molecules and cytokines.

5.8 Dosage & Frequency of Administration

The amount of a prophylactic or therapeutic agent or a composition of the invention which will be effective in the prevention, treatment, management, and/or amelioration of a swine influenza virus infection or a condition associated therewith, an infection other than a swine influenza virus infection or a condition associated therewith, an IFN-treatable disease or a condition in which an attenuated swine influenza virus of the invention is used as a vector to induce an immune response to an antigen associated with the condition, or the prevention of the recurrence, onset, or development of one or more symptoms of a swine influenza virus infection or a condition associated therewith, an infection other than a swine influenza virus infection or a condition associated therewith, an IFN-treatable disease, or a condition in which an attenuated swine influenza virus of the invention is used as a vector to induce an immune response to an antigen associated with the condition, can be determined by standard clinical methods. The frequency and dosage will vary also according to factors specific for each patient depending on the specific therapies (e.g., the specific therapeutic or prophylactic agent or agents) administered, the severity of the disorder, disease, or condition, the route of administration, as well as age, body, weight, response, and the past medical history of the patient. For example, the dosage of a prophylactic or therapeutic agent or a composition of the invention which will be effective in the treatment, prevention, management, and/or amelioration of a swine influenza virus infection or a condition associated therewith, a viral infection other than a swine influenza virus infection or a condition associated therewith, or an IFN-treatable disease, or the prevention of the recurrence, onset, or development of one or more symptoms of a swine influenza virus infection or a condition associated therewith, a viral infection other than a swine influenza virus infection or a condition associated therewith, or an IFN-treatable disease, can be determined by animal models such as those known to those skilled in the art. In addition, in vitro assays may optionally be employed to help identify optimal dosage ranges. Suitable regimens can be selected by one skilled in the art by considering such factors and by following, for example, dosages are reported in literature and recommended in the *Physician's Desk Reference* (58th ed., 2004), Merck Veterinary Manual (8th ed., 1998), or Straw et al., Diseases of the Swine, Iowa State University Press (1999).

Exemplary doses of a vaccine or immunogenic formulation include $10^2$ to about $10^8$, about $10^3$ to about $10^7$, about $10^4$ to about $5 \times 10^6$ pfu or $10^4$ to about $10^7$ pfu. In other embodiments, the dose of a vaccine or immunogenic formulation of the invention administered to a subject is $10^2$, $5 \times 10^2$, $10^3$, $5 \times 10^3$, $10^4$, $5 \times 10^4$, $10^5$, $5 \times 10^5$, $10^6$, $5 \times 10^6$, $10^7$, $5 \times 10^7$ or $10^8$ pfu. Exemplary doses of a pharmaceutical formulation include $10^2$, $5 \times 10^2$, $10^3$, $5 \times 10^3$, $10^4$, $5 \times 10^4$, $10^5$, $5 \times 10^5$, $10^6$, $5 \times 10^6$, $10^7$, $5 \times 10^7$, $10^8$, $5 \times 10^8$, $1 \times 10^9$, $5 \times 10^9$, $1 \times 10^{10}$, $5 \times 10^{10}$, $1 \times 10^{11}$, $5 \times 10^{11}$ or $10^{12}$ pfu. In certain embodiments, the dose of the pharmaceutical formulation administered to the subject is between about $10^2$ to about $10^{12}$, about $10^2$ to about $10^{10}$, about $10^2$ to about $10^8$, about $10^3$ to about $10^9$, about $10^3$ to about $10^7$, about $10^4$ to about $10^8$, about $10^4$ to about $5 \times 10^6$ pfu or about $10^4$ to about $10^{12}$ pfu.

Exemplary doses of a small molecule include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram).

For antibodies, proteins, polypeptides, peptides and fusion proteins encompassed by the invention, the dosage administered to a patient is typically 0.0001 mg/kg to 100 mg/kg of the patient's body weight. Preferably, the dosage administered to a patient is between 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg to 0.25 mg/kg, 0.0001 to 0.15 mg/kg, 0.0001 to 0.10 mg/kg, 0.001 to 0.5 mg/kg, 0.01 to 0.25 mg/kg or 0.01 to 0.10 mg/kg of the patient's body weight. Generally, pig antibodies have a longer half-life within the pig than antibodies from other species due to the immune response to the foreign polypeptides. Thus, lower dosages of pig antibodies and less frequent administration to pigs is often possible. Further, the dosage and frequency of administration of antibodies or fragments thereof may be reduced by enhancing uptake and tissue penetration of the antibodies by modifications such as, for example, lipidation.

Preferably, the dosages of prophylactic or therapeutic agents used in combination therapies of the invention are lower than those which have been or are currently being used to prevent, treat, manage, and/or ameliorate a swine influenza virus infection or a condition or symptoms associated therewith, an infection other than a swine influenza virus infection or a condition or symptom associated therewith, an IFN treatable disease, or a condition in which an attenuated swine influenza virus of the invention is used as a vector to induce an immune response to an antigen associated with the condition. The recommended dosages of agents currently used for the prevention, treatment, management, or amelioration of a swine influenza virus infection or a condition or symptoms associated therewith, an infection other than a swine influenza virus infection or a condition or symptom associated therewith, an IFN treatable disease, or a condition in which an attenuated swine influenza virus of the invention is used as a vector to induce an immune response to an antigen associated with the condition, can be obtained from any reference in the art including, but not limited to, Hardman et al., eds., 2001, Goodman & Gilman's The Pharmacological Basis Of Basis Of Therapeutics, 10th ed., Mc-Graw-Hill, New York; Physicians' Desk Reference (PDR) 58th ed., 2004, Medical Economics Co., Inc., Montvale, N.J., and Merck Veterinary Manual (8th ed., 1998); Taylor, *Pig Diseases,* $6^{th}$ Ed., Diamond Farm Book Pubns, 1995; and Straw et al., *Diseases of Swine,* $8^{th}$ Ed., Iowa State University Press, 1999, which are incorporated by reference herein in their entireties.

In various embodiments, the therapies (e.g., prophylactic or therapeutic agents) are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In preferred embodiments, two or more therapies are administered within the same patent visit.

In certain embodiments, one or more compositions of the invention and one or more other therapies (e.g., prophylactic or therapeutic agents) are cyclically administered. Cycling therapy involves the administration of a first therapy (e.g., a first prophylactic or therapeutic agent) for a period of time, followed by the administration of a second therapy (e.g., a second prophylactic or therapeutic agent) for a period of time, optionally, followed by the administration of a third therapy (e.g., prophylactic or therapeutic agent) for a period of time and so forth, and repeating this sequential administration, i.e., the cycle in order to reduce the development of resistance to one of the therapies, to avoid or reduce the side effects of one of the therapies, and/or to improve the efficacy of the therapies.

In a certain other embodiments, a vaccine or immunogenic composition of the invention is administered to a subject at a single dose followed by a second dose 3 to 6 weeks later. In accordance with these embodiments, booster vaccinations are administered to the subject at 6 to 12 month intervals following the second vaccination. In a preferred embodiment, the subject is a mammal. In a more preferred embodiment, the subject is a pig with an swine influenza A infection.

In certain embodiments, the administration of the same compostions of the invention may be repeated and the administrations may be separated by at least 1 day, 2 days, 3 days, 5 days, 10 days, 15 days, 30 days, 45 days, 2 months, 75 days, 3 months, or at least 6 months. In other embodiments, the administration of the same therapy (e.g., prophylactic or therapeutic agent) other than a composition of the invention may be repeated and the administration may be separated by at least at least 1 day, 2 days, 3 days, 5 days, 10 days, 15 days, 30 days, 45 days, 2 months, 75 days, 3 months, or at least 6 months.

5.9 Biological Assays 5.9.1 In Vitro Assays

Growth of the attenuated swine influenza viruses of the present invention can be assessed in pig cells, e.g., PK cells, other pig cells as described herein, and other IFN-competent and IFN-deficient cells. In a specific embodiment, PK cells are infected at a MOI of 0.0005 and 0.001, 0.001 and 0.01, 0.01 and 0.1, 0.1 and 1, or 1 and 10, or a MOI of 0.0005, 0.001, 0.005, 0.01, 0.05, 0.1, 0.5, 1, 5 or 10 and incubated with serum free media supplemented with 5% allantoic fluid (F. Cook, University of Kentucky, Lexington, Ky.). Viral titers are determined in the supernatant by HA plagued in MDCK cells as described below. Other cells in which viral titers can be assessed include, but are not limited to, PK cells, Vero cells, primary human umbilical vein endothelial cells (HUVEC), H292 human epithelial cell line, HeLa cells, and swine embryonic kidney cells RES.

Viral assays include those that measure altered viral replication (as determined, e.g., by plaque formation) or the production of viral proteins (as determined, e.g., by western blot analysis) or viral RNAs (as determined, e.g., by RT- PCR or northern blot analysis) in cultured cells in vitro using methods which are well known in the art.

Induction of IFN responses may be determined by measuring the phosphorylated state of components of the IFN pathway following infection with the test mutant virus, e.g., IRF-3, which is phosphorylated in response to double-stranded RNA. In response to type I IFN, Jak1 kinase and TyK2 kinase, subunits of the IFN receptor, STAT1, and STAT2 are rapidly tyrosine phosphorylated. Thus, in order to determine whether the attenuated swine influenza virus induces IFN responses, cells, such as 293 cells, are infected with the test mutant virus and following infection, the cells are lysed. IFN pathway components, such as Jak1 kinase or TyK2 kinase, are immunoprecipitated from the infected cell lysates, using specific polyclonal sera or antibodies, and the tyrosine phosphorylated state of the kinase is determined by immunoblot assays with an anti-phosphotyrosine antibody (e.g., see Krishnan et al. 1997, Eur. J. Biochem. 247: 298-305). An enhanced phosphorylated state of any of the components of the IFN pathway following infection with the attenuated swine influenza virus would indicate induction of IFN responses by the attenuated swine influenza virus.

Induction of IFN responses may be determined by measuring IFN-dependent transcriptional activation following infection with the test attenuated swine influenza virus. In this embodiment, the expression of genes known to be induced by IFN, e.g., Mx, PKR, 2-5-oligoadenylatesynthetase, major histocompatibility complex (MHC) class I, etc., can be analyzed by techniques known to those of skill in the art (e.g., northern blots, western blots, PCR, etc.). Alternatively, test cells such as embryonic kidney cells or osteogenic sarcoma cells, are engineered to transiently or constitutively express reporter genes such as luciferase reporter gene or chloramphenicol transferase (CAT) reporter gene under the control of an interferon stimulated response element, such as the IFN-stimulated promoter of the ISG-54K gene (Bluyssen et al., 1994, Eur. J. Biochem. 220:395-402). Cells are infected with the test attenuated swine influenza virus and the level of expression of the reporter gene compared to that in uninfected cells or cells infected with wild-type virus. An increase in the level of expression of the reporter gene following infection with the test virus would indicate that the test attenuated swine influenza virus is inducing an IFN response.

Measuring IFN induction can also be assessed by determining whether an extract from the cell or egg infected with the test attenuated swine influenza virus is capable of conferring protective activity against viral infection. More specifically, groups of 10-12 day old embryonated chicken eggs or 10-day old embryonated chicken eggs are infected with the test attenuated swine influenza virus or the wild-type virus. Approximately 15 to 20 hours post infection, the allantoic fluid is harvested and tested for IFN activity by determining the highest dilution with protective activity against swine influenza virus infection in tissue culture cells, such as MDCK cells.

5.9.2 In Vivo Assays

The decreased virulence of the attenuated swine influenza viruses of the present invention can be assessed in a subject, in particular, pigs. In one example, the ability to induce lung lesions and cause infection in swine is compared to wild-type swine influenza virus and mock virus. Lung lesions can be assessed as a percentage of lung lobes that are healthy by visual inspection. Animals are euthanized 5 days p.i. by intravenous administration of pentobarbital, and their lungs are removed in toto. The percentage of the surface of each pulmonary lobe that is affected by macroscopic lesions is estimated visually. The percentages are averaged to obtain a mean value for the 7 pulmonary lobes of each animal.

In other assays, nasal swabs and BALF can be tested to determine virus burden or titer. Nasal swabs can be taken during necropsy to determine viral burden post-infection. Samples can also be taken with care from live pigs to determine viral burden post-infection. BALF can be obtained after the lungs are removed from the thoracic cavity by rinsing the lungs (via trachea) with about 30 ml of McCoy's medium without serum.

For quantitation of virus in tissue samples, tissue samples are homogenized in phosphate-buffered saline (PBS), and dilutions of clarified homogenates adsorbed for 1 h at 37° C. onto monolayers of MDCK cells. Infected monolayers are then overlaid with a solution of minimal essential medium containing 0.1% bovine serum albumin (BSA), 0.01% DEAE-dextran, 0.1% $NaHCO_3$, and 1% agar. Plates are incubated 2 to 3 days until plaques could be visualized. Tissue culture infectious dose (TCID) assays to titrate virus from PR8-infected samples are carried out as follows. Confluent monolayers of MDCK cells in 96-well plates are incubated with log dilutions of clarified tissue homogenates in media. Two to three days after inoculation, 0.05-ml aliquots from each well are assessed for viral growth by hemagglutination assay (HA assay).

In yet other assays, histopathologic evaluations are performed after infection. The nasal turbinates and trachea are examined for epithelial changes and subepithelial inflammation. The lungs are examined for bronchiolar epithelial changes and peribronchiolar inflammation in large, medium, and small or terminal bronchioles. The alveoli are also evaluated for inflammatory changes. The medium bronchioles are graded on a scale of 0 to 3+ as follows: 0 (normal: lined by medium to tall columnar epithelial cells with ciliated apical borders and basal pseudostratified nuclei; minimal inflammation); 1+ (epithelial layer columnar and even in outline with only slightly increased proliferation; cilia still visible on many cells); 2+ (prominent changes in the epithelial layer ranging from attenuation to marked proliferation; cells disorganized and layer outline irregular at the luminal border); 3+ (epithelial layer markedly disrupted and disorganized with necrotic cells visible in the lumen; some bronchioles attenuated and others in marked reactive proliferation).

The trachea is graded on a scale of 0 to 2.5+ as follows: 0 (normal: Lined by medium to tall columnar epithelial cells with ciliated apical border, nuclei basal and pseudostratified. Cytoplasm evident between apical border and nucleus. Occasional small focus with squamous cells); 1+ (focal squamous metaplasia of the epithelial layer); 2+ (diffuse squamous metaplasia of much of the epithelial layer, cilia may be evident focally); 2.5+ (diffuse squamous metaplasia with very few cilia evident).

Swine influenza virus immunohistochemistry is performed using a NP-specific monoclonal antibody. Staining is graded 0 to 3+ as follows: 0 (no infected cells); 0.5+ (few infected cells); 1+ (few infected cells, as widely separated individual cells); 1.5+ (few infected cells, as widely separated singles and in small clusters); 2+ (moderate numbers of infected cells, usually affecting clusters of adjacent cells in portions of the epithelial layer lining bronchioles, or in small sublobular foci in alveoli); 3+ (numerous infected cells, affecting most of the epithelial layer in bronchioles, or widespread in large sublobular foci in alveoli).

5.9.3 Determining Viral Titer

Viral titer is determined by inoculating serial dilutions of swine influenza virus into cell cultures (e.g., pig cultures), chick embryos, or live animals (e.g., pigs). After incubation of the virus for a specified time, the virus is isolated using standard methods.

Physical quantitation of the virus titer can be performed using PCR applied to viral supernatants (Quinn & Trevor, 1997; Morgan et al., 1990), hemagglutination assays, tissue culture infectious doses (TCID50) or egg infectious doses (EID50).

The HA assay is carried out in V-bottom 96-well plates. Serial twofold dilutions of each sample in PBS were incubated for 1 h on ice with an equal volume of a 0.5% suspension of chicken erythrocytes in PBS. Positive wells contained an adherent, homogeneous layer of erythrocytes; negative wells contain a nonadherent pellet.

5.9.4 Determining Hemagglutination Inhibiting Antibody Titers

In one method, HA inhibition assay, the levels of hemagglutination (HA)-inhibiting (HI) antibodies in samples are determined as described previously (Palmer et al., 1975, Advanced laboratory techniques for influenza diagnosis. U.S. Department of Health, Education and Welfare Immunology Series. U.S. Department of Health, Education and Welfare, Washington, D.C.). Briefly, samples are incubated overnight at 37° C. with 4 volumes of receptor-destroying enzyme (Denka Seiken Co., Tokyo, Japan) prepared from *Vibrio cholerae*. After inactivation of the receptor-destroying enzyme by incubation of the samples at 56° C. for 60 min, twofold serial dilutions of sera are mixed with 4 HA units of swine influenza virus. The assays are developed by adding 0.5% (vol/vol) chicken red blood cells, and the HI antibody titers are defined as the reciprocal of the highest dilution causing complete inhibition of agglutination.

5.9.5 Toxicity Studies

The toxicity and/or efficacy of the compositions of the present invention can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Therapies that exhibit large therapeutic indices are preferred. While therapies that exhibit toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage of the therapies for use in subjects (e.g., pigs). The dosage of such agents lies preferably within a range of circulating concentrations that include the ED50 with little or no toxicity. The dosage may vary within this range depending upon the dosage form employed and the route of administration utilized. For any therapy used in the method of the invention, the therapeutically effective dose can be estimated initially from cell culture assays. A dose may be formulated in animal models to achieve a circulating plasma concentration range that includes the IC50 (i.e., the concentration of the test compound that achieves a half-maximal inhibition of symptoms) as determined in cell culture. Such information can be used to more accurately determine useful doses in subjects (e.g., pigs). Levels in plasma may be measured, for example, by high performance liquid chromatography.

Further, any assays known to those skilled in the art can be used to evaluate the prophylactic and/or therapeutic utility of a composition, a combination therapy disclosed herein for swine influenza virus infection or a condition or symptoms associated therewith, an infection other than a swine influenza virus infection or a condition or symptom associated therewith, an IFN treatable disease, or a condition in which an attenuated swine influenza virus of the invention is used as a vector to induce an immune response to an antigen associated with the condition.

The following examples are provided to further illustrate the current invention but are not provided to in any way limit the scope of the current invention.

6. EXAMPLES

6.1 Example 1: Generation of Plasmid-Derived Sw/Tx98 Viruses Encoding Truncated NS1

Site directed mutagenesis was used to generate different deletions in the swine influenza virus NS segment in such a way that the NEP was expressed without any alteration while the NS1 was partially deleted. This was achieved by inserting a stop codon in the NS1 ORF followed by a deletion in the NS1 ORF encompassing nucleotides not involved in NEP expression.

Cells and Viruses.

Pig kidney-15 (PK-15), Swine Testis (ST) and Madin-Darby canine kidney (MDCK) type II cells were grown in minimal essential medium (MEM) supplemented with 10% fetal bovine serum (FBS). Baby hamster kidney (BHK), 293T and A549 cells were grown in DMEM with 10% FBS. All cells were maintained at 37° C. and 5% $CO_2$. The A/Swine/Texas/4199-2/98 (TX/98, H3N2 subtype) influenza virus was obtained from the repository at St. Jude Children's Research Hospital, Memphis, Tenn. Influenza viruses were grown in the allantoic cavities of embryonated chicken eggs or in MDCK cells. Recombinant vesicular stomatitis virus expressing GFP (VSV-GFP) (Stojdl, 2003, Cancer Cell 4:263-75) was grown and titrated in BHK cells for use in IFN bioassays.

Construction of Plasmids.

MDCK cells were infected with TX/98 virus and total RNA was extracted by using Trizol reagent according to the manufacturer's instructions (Invitrogen). The eight reverse genetics plasmids pHW-Sw-PB2, pHW-Sw-PB1, pHW-Sw-PA, pHW-Sw-HA, pHW-Sw-NP, pHW-Sw-NA, pHW-Sw-M and pHW-Sw-NS (corresponding to the eight influenza viral segments listed in Table 1) were constructed by RT-PCR amplification of single viral RNA segments and cloning of the resulting cDNAs into the vector pHW2000 (Hoffmann et al., 2000, Proc. Natl. Acad. Sci. USA 97:6108-6113). The insert sequences for pHW-Sw-PB2, pHW-Sw-PB1, pHW-Sw-PA, pHW-Sw-HA, pHW-Sw-NP, pHW-Sw-NA, pHW-Sw-M and pHW-Sw-NS are provided in SEQ ID NOS: 1-8, respectively. In this system, influenza viral cDNA is inserted between the RNA polymerase I (polI) promoter and terminator sequences. This entire RNA polI transcription unit is flanked by an RNA polymerase II (polII) promoter and a polyadenylation site. The orientation of the two promoters allows the synthesis of negative-sense viral RNA and positive-sense mRNA from one viral cDNA template. pHW-Sw-NS-73, pHW-Sw-NS-99 and pHW-Sw-NS-126 are derivatives of pHW-Sw-NS. These NS1 mutant plasmids were constructed by trimolecular ligation: Two PCR products were ligated into SalI/NgoIV digested pHW2000-Sw-NS.

The first PCR product was common for all three NS1 mutant plasmids, and was obtained using oligo pHW-3' (reverse, annealing in the plasmid pHW2000 backbone) GGGTCAAGGAAGGCACGGGGGAGGGGC (SEQ ID NO: 9) and oligo 5'NS-PacI (forward, annealing in the NS1 gene) GCGCTTAATTAAGAGGGAGCAATCGTTGGAG (SEQ ID NO: 10) and pHW2000-Sw-NS as template. This PCR product was digested with NgoIV and PacI.

The second PCR product was specific for each NS1 mutant plasmid, and was obtained using: a common forward primer, CMV5' (annealing in the CMV promoter of pHW2000 plasmid) GCCCCATTGACGCAAATGGGCGGTAGGCGTG (SEQ ID NO: 11), and a specific reverse primer (annealing in the NS1 gene): NS73-BglII-PacI-3' GCGCTTAATTAATCAAGATCTAGGATTCCTCTTTCAAAATCC (SEQ ID NO: 12), NS99-BglII-PacI-3' GCTTAATTAATCAAGATCTATGACATTTCCTCGAGGGTCATG (SEQ ID NO: 13) or NS126-BglII-PacI-3' GCGCTTAATTAATCAAGATCTACTTTTCCATGATCGCCTGGTCC (SEQ ID NO: 14). The three corresponding PCR products were digested with SalI and PacI, and used in trimolecular ligation together with the PacI/NgoIV digested first PCR product and SalI/NgoIV digested pHW2000-Sw-NS, to generate: pHW-Sw-Tx-73, pHW-Sw-Tx-99 and pHW-Sw-Tx-126. These constructs contain a deletion in the NS1 sequence, plus the insertion of 4 stop codons in the 3 frames after this deletion. See FIG. 1A. While the nuclear export protein (NEP) ORF is not altered in these constructs, the NS1 ORF encodes only the first 73, 99 and 126 amino acids of the wild-type NS1 protein (total length of wild type NS1 is 219 amino acids), respectively.

The viral strains are described below:

Sw/TX/98 wt: contains wild-type NS1 gene and represents a triple-reassortant H3N2 swine influenza virus.

Sw/TX/98/del126: expresses the N-terminal 126 amino acids of the wild-type NS1 protein.

Sw/TX/98/del99: expresses the N-terminal 99 amino acids of the wild-type NS1 protein.

Sw/TX/98/del73: expresses the N-terminal 72 amino acids of the wild-type NS1 protein.

Transfection-Mediated Recovery of Recombinant SIV.

Rescue of influenza viruses from plasmid DNA was performed as described in Fodor et al. (1999, J Virol 73:9679-82) and Neumann et al. (1999, Proc Natl Acad Sci USA 96:9345-50) using an eight-plasmid system (Hoffmann et al., 2000, Proc. Natl. Acad. Sci. USA 97:6108-6113). To generate the recombinant wild type (rWT) TX/98 virus 0.5 µg of each of the 8 pHW plasmids were transfected into $10^6$ 293 T cells in suspension using the Lipofectamine 2000 reagent (Invitrogen). The NS1 truncated mutant viruses were generated in the same way but substituting the pHW-Sw-NS plasmid by the corresponding mutant one to recover the del73, del99 or del126 virus mutants. The resulting viruses were passaged and cloned by plaque purification into MDCK cells. Virus stocks were grown in 7-day-old embryonated chicken eggs. The identity of the recombinant viruses SIV was verified by gel electrophoretic analyses of RT-PCR products derived from viral RNA using oligonucleotides specific for the common non-coding regions. The wild type NS gene or the deleted versions were further confirmed by sequencing.

Results.

To generate SIV using reverse genetics, the eight viral RNAs from Tx/98 virus were cloned into ambisense expression plasmids for viral rescue (Hoffmann et al., 2000, Proc. Natl. Acad. Sci. USA 97:6108-6113). Upon transfection of these plasmids in 293T cells, infectious viruses were recovered. The parental (WT) and the plasmid-derived wild type (rWT) SIVs grew to similar titers in MDCK cells and embryonated eggs. When inoculated into pigs, the rWT virus produced similar lesions as the parental WT virus. Three NS1-truncated SIV mutants were generated encoding NS1 proteins of 73, 99 and 126 amino acids, as compared to the full length, 219 amino acids long, NS1 protein (FIG. 1A). RT-PCR and sequencing analyses confirmed the presence of the truncated NS1 genes in the rescued virus preparations (FIG. 1B).

6.2 Example 2: Characterization of the Swine Influenza Virus NS1 Deletion Mutants and Wild Type A/Swine/Texas/4199-2/98

To characterize the impact of the NS1 gene deletion on the replicative properties of swine influenza virus, the growth of the wild-type and the different deletion mutants described in Section 6.1 was compared. Also, the effect of these mutants on IFN production was compared.

Virus Growth Curves.

To analyze viral replication, confluent PK-15 cells were infected at the indicated multiplicity of infection (MOI) and incubated for different periods of times at 37° C. in MEM containing 0.3% bovine albumin (MEM/BA) and 5% allantoic fluid. Virus titers were determined by plaque assay on MDCK cells in MEM/BA supplemented with 1 µg/ml of TPCK trypsin. Titers were expressed as plaque forming units (PFU) per ml.

Figure 2A:
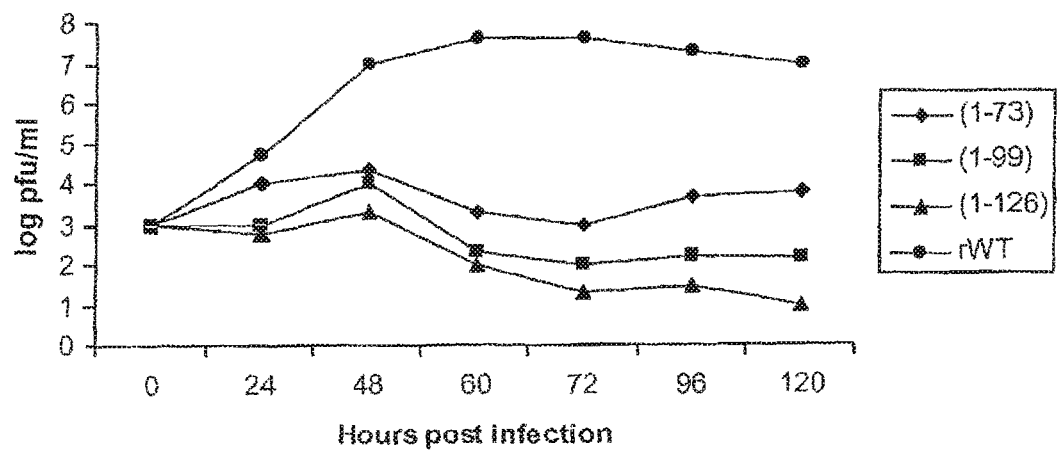
Figure 2B:
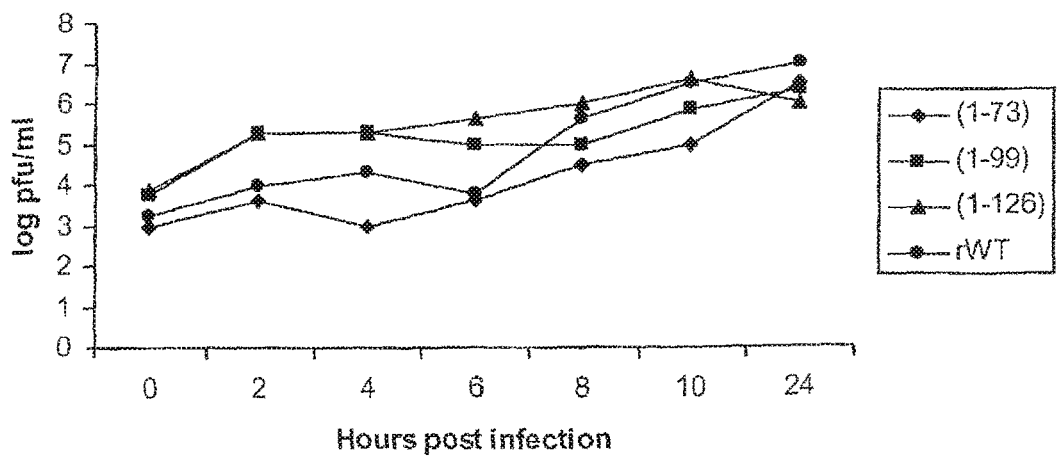
Figure 2C:
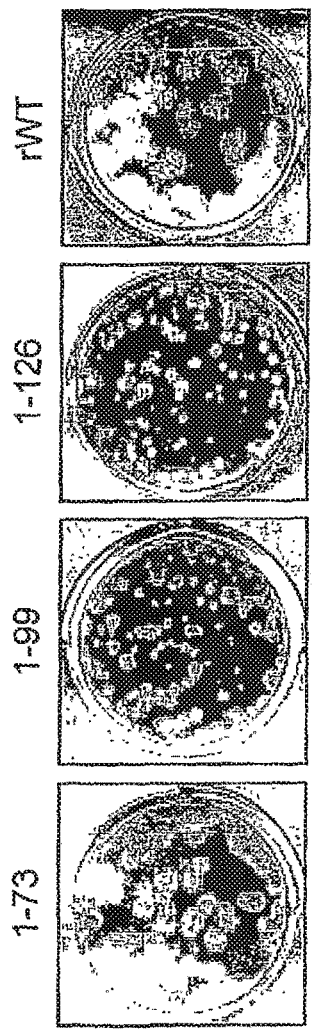

In order to investigate the multicycle growth properties of the mutant NS1 viruses confluent pig epithelial cells (PK-15) were infected at a low MOI (MOI=0.001). Supernatants from infected cells were titrated at different time points post infection by plaque assay on MDCK cells. The growth kinetics of the NS1 deletion mutants in PK-15 cells were clearly different when compared to the wild type virus. Interestingly, the 1-126 mutant virus was the most compromised in growth, followed by the 1-99 and the 1-73 mutants (FIG. 2A). Plaque sizes in MDCK cells correlated with the growth differences in PK-15 cells (FIG. 2C). These results indicate that deletions in the NS1 protein of Sw/TX/98 virus result in attenuation of viral growth, both in PK-15 and MDCK cells. In contrast, when NS1 mutant viruses were grown at a high MOI (MOI=2) in PK-15 cells major differences in growth kinetics were not detected (FIG. 2B). This most likely indicates that virus replication of the NS1 mutant viruses is not restricted during the first cycle of replication, suggesting that infected cells secrete antiviral cytokines, such as IFN, that inhibit subsequent rounds of replication.

Metabolic Labeling.

Confluent PK-15 cells seeded in 22-mm dishes were either mock-infected or infected with rWT, 1-73, 1-99 or 1-126 viruses at an MOI of 2. Cells were incubated in MEM/BA at 37° C. for various time points, and subsequently labeled for 2 h with 10 µCi [$^{35}$S]Met-Cys in MEM lacking Met-Cys. Cells were washed with ice-cold phosphate-buffered saline (PBS), lysed and total cell extracts were separated by sodium dodecyl sulfate-polyacrylamide gel electrophoresis (SDS-PAGE). The proteins were visualized by autoradiography.

Figure 2D:
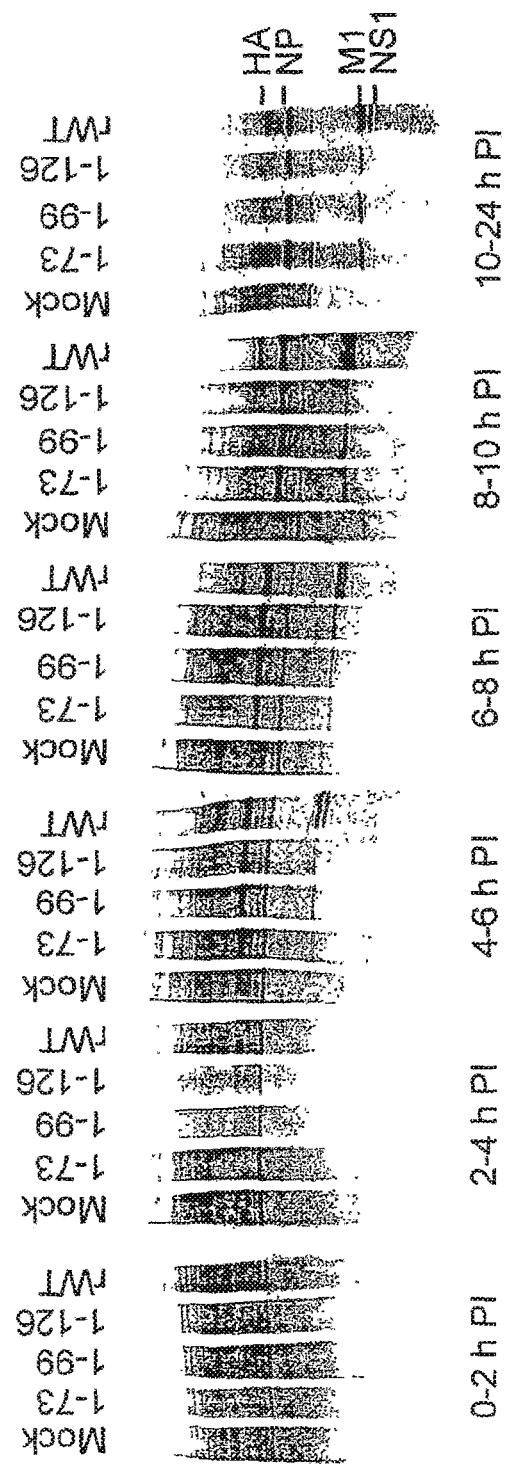

Metabolic labeling of virus-infected PK cells (MOI=2) with [$^{35}$S]-Met-Cys, revealed no differences in the kinetics of NP protein synthesis among rWT and 1-73, 1-99 and 1-126 mutant viruses (FIG. 2D). The NS1 mutant proteins could not be detected by labeling.

Bioassay to Measure IFN Production.

Levels of IFN secreted by virus infected cells were determined as previously described (Park et al., 2003, J. Virol. 70:9522-9532; Donelan, 2003, J Virol 77:13257-66), with some variations. Confluent PK-15 cells seeded in 22-mm dishes were either mock-treated or infected with rWT, del73, del99 or del126 viruses at an MOI of 2. Following infection, cells were incubated with MEM/BA containing 5% allantoic fluid, and at different time points post-infection, supernatants were harvested. Viruses present in the supernatant were UV inactivated by placing samples on ice 6 inches below an 8-W UV lamp (Fisher) for 15 min with constant stirring. New PK-15 cells were seeded in 96-well plates the day before and incubated with the UV-inactivated supernatants for 24 h. The preincubated PK-15 cells were then infected with VSV-GFP (MOI=0.1). The cells expressing GFP were visualized by fluorescence microscopy 16 hours post infection.

Figure 3A:
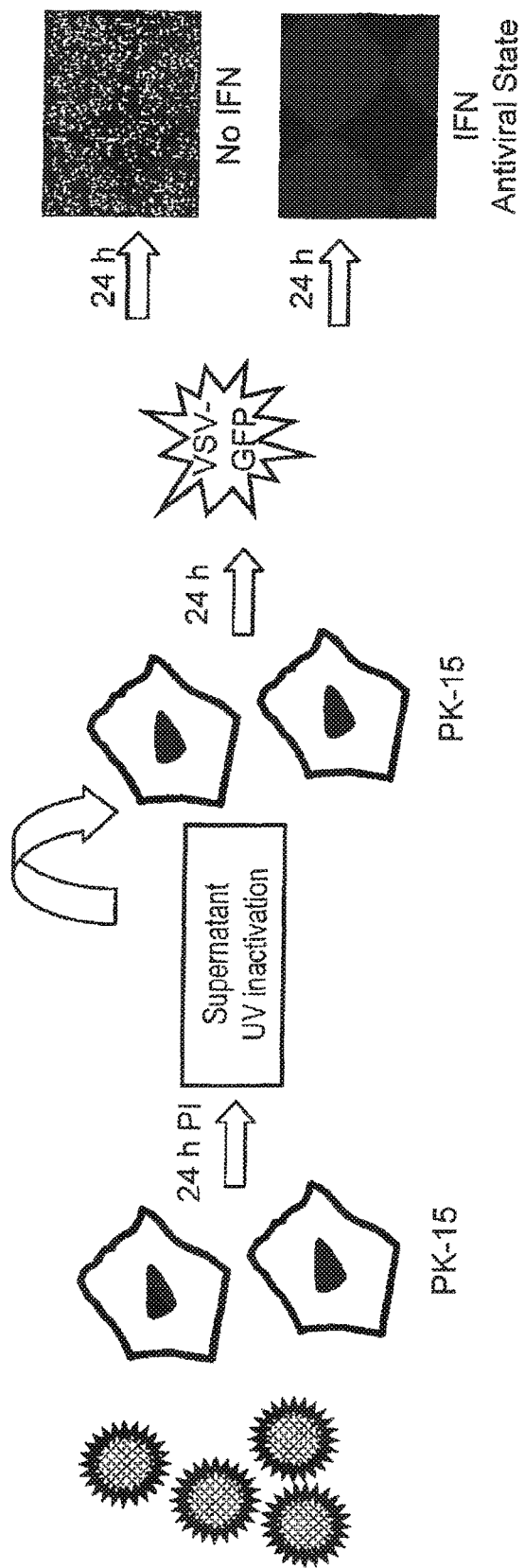
Figure 3B:
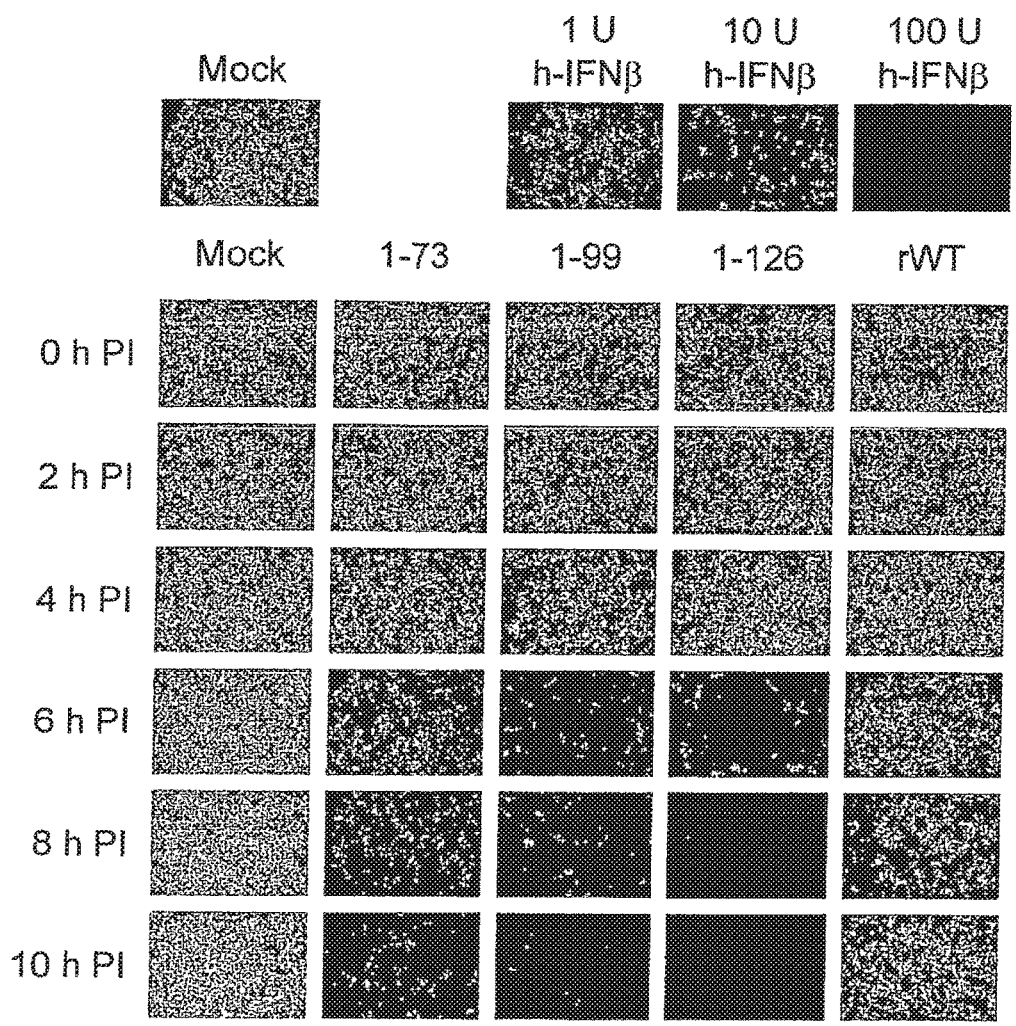

In order to see whether the observed attenuation of growth in vitro of the NS1-truncated viruses was directly correlated with the ability of these viruses to inhibit the IFN-α/0 system, the induction of IFN in cells infected with the recombinant Sw/Tx/98 viruses was investigated. Supernatants of infected PK-15 cells were used to determine the levels of secreted IFN-α/β using a bioassay based on inhibition of VSV-GFP replication FIG. 3A). For this purpose, PK-15 cells were infected (MOI=2) with rWT and NS1 mutant SIVs and supernatants were collected for IFN determinations every two hours for 10 h. The results are shown in FIG. 3B. Supernatants from mock-infected cells caused no inhibition of GFP expression by VSV-GFP in PK-15 cells. In contrast, VSV-GFP replication was completely abolished in cells pretreated with the supernatant of del126 virus-infected cells at 10 h post infection. No IFN-α/0 was detected by this assay in supernatants of cells infected with rWT virus. All NS1-truncated viruses induced detectable levels of IFN-α/0 by 6 h post infection, with 1-126 virus being the stronger IFN-α/0 inducer, followed by del99 and del73 viruses. Similar experiments were performed using other virus-infected swine (ST) and human (A549) cell lines with basically identical results.

Analysis of IFN-β and TNF-α mRNA by RT-PCR.

PK-15 cells were infected at an MOI of 2, and at 24 hours post infection, total RNA was extracted using Absolutely RNA RT-PCR Miniprep Kit (Stratagene). RT was performed by using oligodT as the primer. PCR was done using specific pairs of primers for swine IFN-β (5-SWIFNB+GGCCATG-GCTAACAAGTGCATCC (SEQ ID NO: 15), 3-SWIFNB–CCGGTCAGTTCCGGAGGTAATC (SEQ ID NO: 16)) and TNF-α (5' SW-TNFA ATGAGCACTGAGAGCATG (SEQ ID NO: 17), 3' SW-TNFA TCACAGGGCAATGATCCC (SEQ ID NO: 18)) mRNAs (Genbank accession numbers M86762 and X57321). As control, specific primers for β-actin (Donelan, 2003 J Virol 77:13257-66) were used to amplify a 550-bp fragment of swine β-actin. The products were sequenced and confirmed to be derived from the expected mRNAs.

Figure 3C:
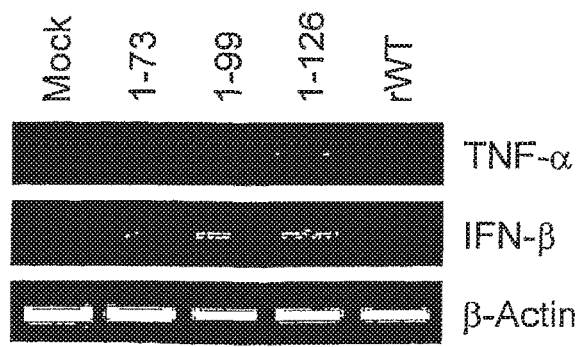

RT-PCR analysis of IFN-β- and TNF-α-transcripts revealed the induction of the expression of the mRNA of these cytokines in PK-15 cells infected with NS1 mutant viruses, especially in 1-126 virus-infected cells (FIG. 3C). These data indicate that the potency of inhibition of IFN production by the recombinant Sw/Tx/98 viruses is as follows: rWT>del73>del99>del126.

6.3 Example 3: Pathogenesis of Plasmid-Derived TX/98 Mutant/Deletion Viruses Pathogenesis of the specific swine influenza viruses described in Section 6.1 were assessed in pigs. The ability of Sw/Tx/98/del126, Sw/Tx/98/del99, and Sw/Tx/98/del73 to induce lung lesions and cause infections in swine were determined and compared to the results obtained for a mock virus and the wild-type virus Sw/Tx/98 wt. Lung lesions were assessed as the percentage of the healthy lung in which lesions occurred with an average of seven lobes of the lung being used for this determination. Viruses or the mock were administered as described in detail below and either nasal swabs or BALF were obtained during necropsy to determine virus burden five days post infection. Histopathologic evaluation was preformed. The nasal turbinates and trachea were examined for epithelial changes and subepithelial inflammation. The alveoli were also evaluated for inflammatory changes.

This example demonstrates that C-terminal deletions of the NS1 gene result in an attenuated phenotype.

6.3.1 Methods

Infection of Pigs.

Out-bred specific pathogen-free pigs were obtained from a commercial hog farm in Iowa (USA). Sera from these pigs was confirmed to be negative for the presence of hemagglutination inhibition antibodies (Palmer, 1975, (U.S. Department of Health, Education, and Welfare, Washington, D.C.), pp. 51-52) against H3N2 (Sw/TX/98 and Sw/CO/99) and H1N1 (Sw/IA/30) SIV. Groups of four to five pigs were housed in separate isolation rooms. At the age of 4 weeks, pigs were anesthetized by intramuscular injection with a mixture of ketamine, xylazine, zolazepam and tiletamine (Mengeling, 1996, Am J Vet Res 57:834-839) before being inoculated intratracheally (via laryngoscope and tracheal tube) with 1 ml of virus solution containing $1\times10^5$PFU. For 5 days, pigs were monitored for clinical signs including lethargy, anorexia, coughing, hyperpnea/dyspnea, nasal and ocular discharge and their body temperature was recorded daily. At day 5, animals were euthanized by intravenous administration of pentobarbital (Fort Dodge Animal Health, Fort Dodge, USA), and their lungs were removed in toto. The percentage of the surface of each pulmonary lobe that was affected by macroscopic lesions was estimated visually. The percentages were averaged to obtain a mean value for the 7 pulmonary lobes of each animal. The nasal turbinates, trachea, and right cardiac lobe were removed and formalin-fixed for further histopathologic evaluation. Blood, bronchoalveolar fluid (BALF) and nasal swabs were also collected during necropsy. BALF was obtained after the lungs were removed from the thoracic cavity by rinsing the lungs (via trachea) with ca. 30 ml of McCoy's medium without serum. All animal experiments were in compliance with the Institutional Animal Care and Use Committee of the National Animal Disease Center.

Clinical Observation and Sampling.

For 5 days, pigs were monitored for clinical signs including lethargy, anorexia, coughing, hyperpnea/dyspnea, nasal and ocular discharge and their body temperature was recorded daily. Blood, BALF, and nasal swabs were collected during necropsy. BALF was obtained after the lungs were removed from the thoracic cavity by rinsing the lungs (via trachea) with ca. 30 ml of McCoy's medium without serum. Nasal swabs and BALF were tested to determine virus burden.

Virus Titrations from Nasal Swabs and BALF.

Nasal swabs and BALF were tested to determine virus burden. Ten-fold serial dilutions were prepared in McCoy's medium without serum, supplemented with 5 μg/ml trypsin. MDCK cells were inoculated with the dilutions and incubated with medium plus trypsin in microtiter plates at 37° C. for 72 h. The plates were examined for cytopathic effects after 72 hours. Virus titers were calculated by the Reed and Muench method (Reed, 1938, Am J Hyg 27:493-497).

Histopathological Evaluation:

The nasal turbinates and trachea were stained with hematoxylin and eosin and examined under the microscope for epithelial changes and subepithelial inflammation. The lungs were examined for bronchiolar epithelial changes and peribronchiolar inflammation in large, medium, and small or terminal bronchioles. The alveoli were also evaluated for inflammatory changes. Because lesions were found most consistently in medium-sized airways, data obtained from the medium bronchioles were used for comparisons. The medium bronchioles were graded on a scale of 0 to 3+ as follows: 0 (normal: lined by medium to tall columnar epithelial cells with ciliated apical borders and basal pseudostratified nuclei; minimal inflammation); 1+ (epithelial layer columnar and even in outline with only slightly increased proliferation; cilia still visible on many cells); 2+ (prominent changes in the epithelial layer ranging from attenuation to marked proliferation; cells disorganized and layer outline irregular at the luminal border); 3+ (epithelial layer markedly disrupted and disorganized with necrotic cells visible in the lumen; some bronchioles attenuated and others in marked reactive proliferation).

The trachea was graded on a scale of 0 to 2.5+ as follows: 0 (normal: Lined by medium to tall columnar epithelial cells with ciliated apical border, nuclei basal and pseudostratified. Cytoplasm evident between apical border and nucleus. Occasional small focus with squamous cells); 1+: (focal squamous metaplasia of the epithelial layer); 2+ (diffuse squamous metaplasia of much of the epithelial layer, cilia may be evident focally); 2.5+ (diffuse squamous metaplasia with very few cilia evident).

SIV immunohistochemistry was performed using mouse NP-specific monoclonal antibody HB65 (American Type Culture Collection, Manassas, Va.). The antibody was produced as mouse ascites fluid. A dilution of 1/1000 of HB65 was used for immunohistochemistry. The assay was performed using the Dako Envision IHC system. Staining was graded 0 to 3+ as follows: 0 (no infected cells); 0.5+ (few infected cells); 1+ (few infected cells, as widely separated individual cells); 1.5+ (few infected cells, as widely separated singles and in small clusters); 2+ (moderate numbers of infected cells, usually affecting clusters of adjacent cells in portions of the epithelial layer lining bronchioles, or in small sublobular foci in alveoli); 3+ (numerous infected cells, affecting most of the epithelial layer in bronchioles, or widespread in large sublobular foci in alveoli).

Statistical Analysis.

Mean body temperatures, extent of gross and histopathologic changes, and virus replication in infected and control groups were compared by using the two-sided Student's t-test. Probability (P) values <0.05 were considered to indicate a statistically significant difference between groups.

6.3.2 Results

Forty seven 4-week-old outbred pigs were purchased from a commercial hog farm in Iowa. Groups of 10 pigs were intratracheally infected with $10^5$ pfu of rWT and NS1 mutant Sw/TX/98 viruses. Seven animals were mock-infected with medium only. The mean rectal temperature of each infected group increased to ≥40° C. 1 to 3 days p.i. in the rWT, 1-73 and 1-99 virus-infected cohorts (data not shown). Not all of the animals infected with NS1 deletion mutant 1-126 exhibited increased temperature. Clinical signs, which comprised respiratory distress, nasal secretion, conjunctivitis, and coughing began on days 2 to 4 p.i. in the rWT-virus infected group. The prevalence of clinical signs differed between the respective viruses. Most clinical signs were consistently observed in the groups infected with the rWT virus while some signs were observed in the 1-99 and 1-73 virus-infected cohorts. Only elevated temperature but no other clinical signs were observed in the 1-126 virus-infected pigs.

Figure 4A:
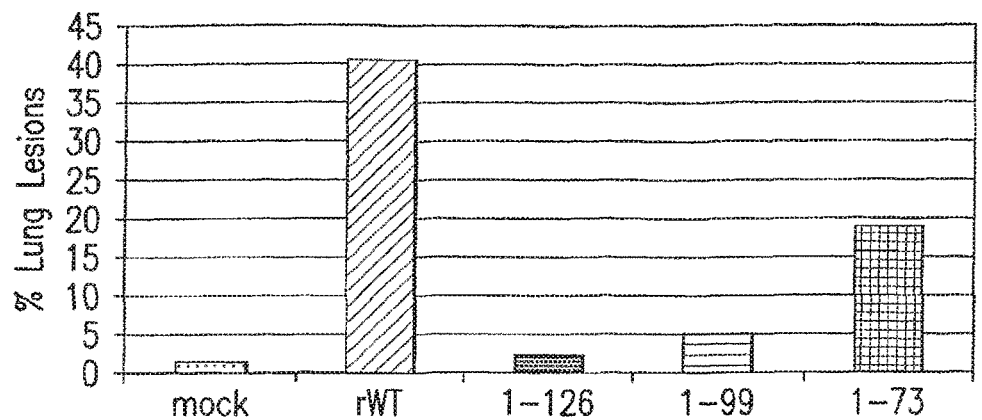

During necropsy at day 5 p.i., the percentage of each lung surface with macroscopic lesions was estimated. As shown in FIG. 4A, mock-infected control animals had no macroscopic lung lesions. Pigs infected with the rWT Sw/Tx/98 virus showed significantly higher percentage of macroscopic lung lesions than pigs infected with the NS1 deletion mutant viruses 1-99 (p=0.006) or 1-126 (p=0.004). Pigs infected with the NS1 deletion mutant virus 1-73 displayed less severe lesions, however, this was not statistically not significant (p>0.05). In general, the gross lesions we observed were marked, plum-colored, consolidated areas on individual lobes. The diaphragmatic lobes were less involved than the other lobes. The mediastinal lymph nodes were usually hyperemic and enlarged.

Figure 4B:
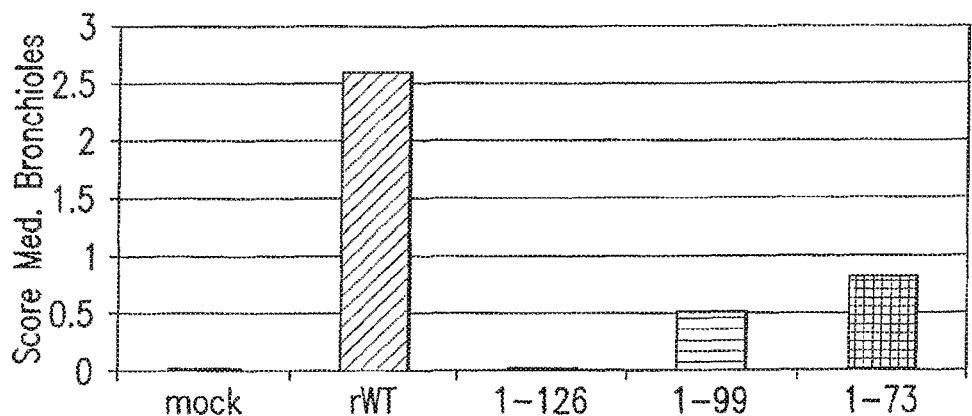

The medium bronchioles were microscopically examined in tissue sections of the right cardiac pulmonary lobe of 4-week-old infected pigs and were histopathologically scored (FIG. 4B). Mock-infected animals as well as 1-126 virus-infected pigs, showed no or minimal lesions, whereas moderate to severe lesions were detected in animals infected with the rWT and the 1-99 and 1-73 Sw/TX/98 viruses (FIGS. 5A-D and 6A-D). All animals infected with the parental wild-type and some infected with the 1-73 and 1-99 viruses had high scores reflecting disruption of the bronchial epithelial cell layer (characterized by acute epithelial necrosis or subsequent attenuation or reactive proliferation). Most animals infected with either 1-73 or 1-99 virus had a moderate score reflecting slightly increased proliferation of the bronchial epithelial layer. The lungs of animals infected with the NS1 deletion mutant 1-126 virus were nearly devoid of lesions. As in the macroscopic lung lesions, 1-126 and 1-99 infected pigs showed significantly less damage than rWT-infected pigs (1-126: p<0.0001; 1-99: p=0.0002). Interestingly, microscopic lesions in bronchioles of pigs infected with the 1-73 mutant virus were also significantly less when compared to the parental rWT virus (p=0.02).

Figure 4C:
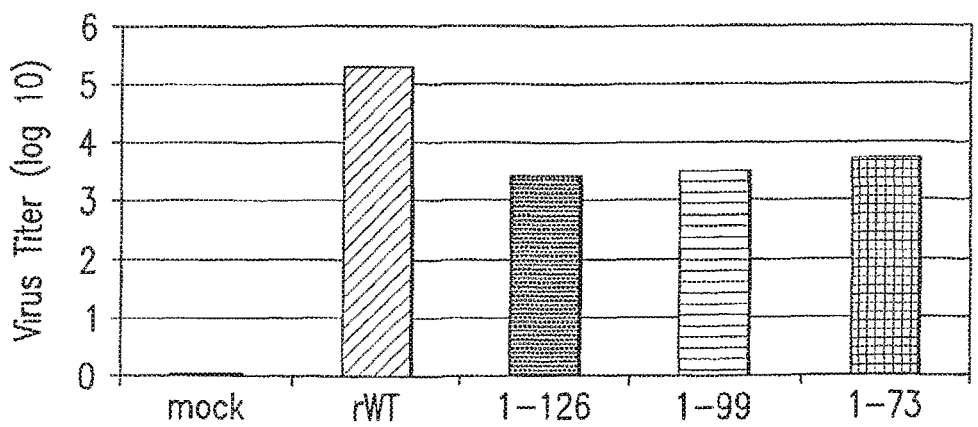
Figure 6A:
Figure 6B:
Figure 6C:
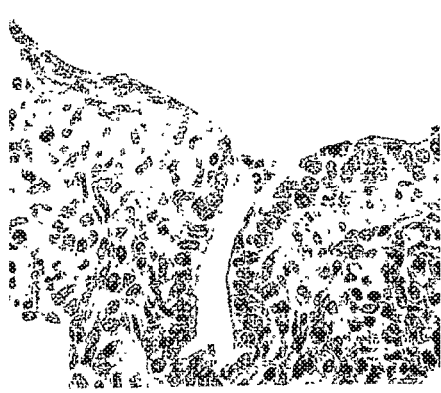
Figure 6D:

Virus titers in the BALF were also analyzed at day 5 p.i. As shown in FIG. 4C, all viruses replicated in the respiratory tract of pigs. BALF virus titers were significantly higher in animals infected with parental rWT virus when compared to the NS1 deletion mutants. This finding correlates with significantly less extensive gross and microscopic disease observed in pigs infected with NS1 deletion mutants versus wild-type Sw/Tx/98 viruses.

6.4 Example 4: Use of TX/98/Del 126 as a Vaccine

The efficacy of the attenuated TX/98/del 126 deletion mutant was tested in a pig vaccination study. Experiments were performed as described in Example 3, except that vaccination with TX/98/del 126 was performed twice on days 0 and day 21 with $1 \times 10^5$ PFU per pig by intratracheal inoculation. The vaccination and challenge was done by intratracheal inoculation (using 1 ml of virus solution/or medium as a control). Animals were challenged 9 days or 10 days later with the following preparations:

$2 \times 10^5$ PFU per pig with wild-type H3N2 virus (A/Swine/Texas/4199-2/98-homologous challenge)

$2 \times 10^5$ PFU per pig with wild-type H1N1 virus (A/Swine/MN/37866/99 classical H1N1-heterologous challenge)

Mock challenge with 1 ml medium

For histopathological evaluation, the right cardiac lobe of each lung was stained with hematoxylin and eosin and examined for bronchiolar epithelial changes and peribronchiolar inflammation in large, medium, and small or terminal bronchioles. Because lesions were found most consistently in medium-sized airways, data obtained from the medium bronchioles were used for comparisons. Lesion severity was scored by the distribution or extent of lesions within the sections examined as follows: 0—No airways affected. 1—Only a few isolated airways affected; 2—Localized cluster of affected airways, often within one or two lobules. 3—Low number of airways affected but throughout much of the section. 4—Many airways affected, often severely, all sizes.

One trained examiner was utilized for evaluation of tissue sections. The examiner was unaware of which group of animals the tissues were derived from.

Immunohistochemistry was done using a monoclonal antibody specific for the nucleoprotein of influenza. The antigen score was as follows:

0=No antigen positive cells.
1=Only a few cells with positive staining in an occasional airway.
2=Only a few cells with positive staining in scattered airways which may be localized.
3=Moderate numbers of cells with positive staining in an occasional airway.
4=Moderate numbers of cells with positive staining in scattered airways and alveoli.

Lung lavage was tested to determine virus load. Ten-fold serial dilutions were prepared in McCoy's medium without serum, supplemented with 5 µg/ml trypsin. MDCK cells were inoculated with the dilutions and incubated with medium plus trypsin in microtiter plates at 37° C. for 72 h. The plates were examined for cytopathic effects after 72 hours. Virus titers were calculated by the Reed and Muench method.

Results.

Figure 7:
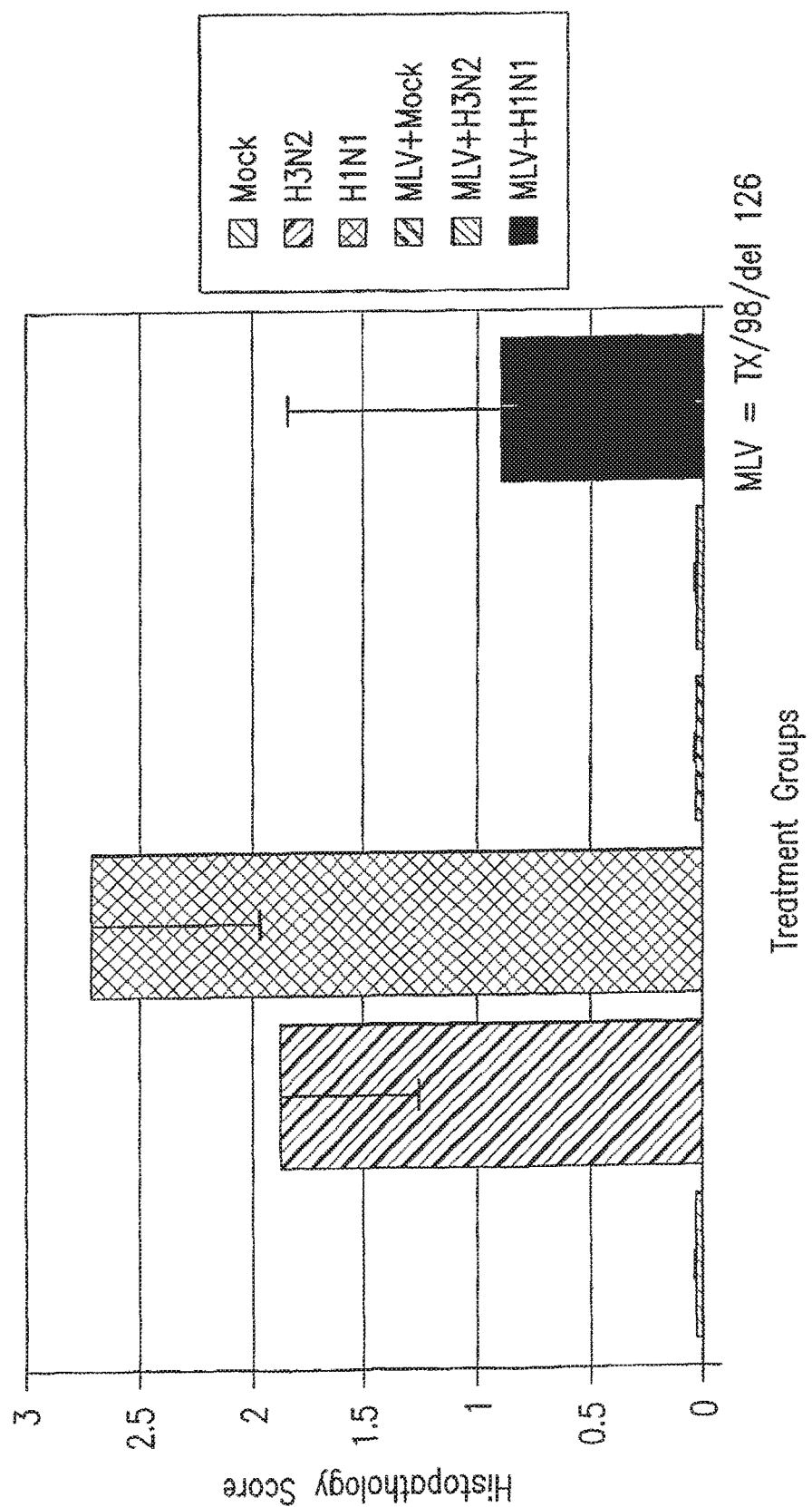
Figure 8:
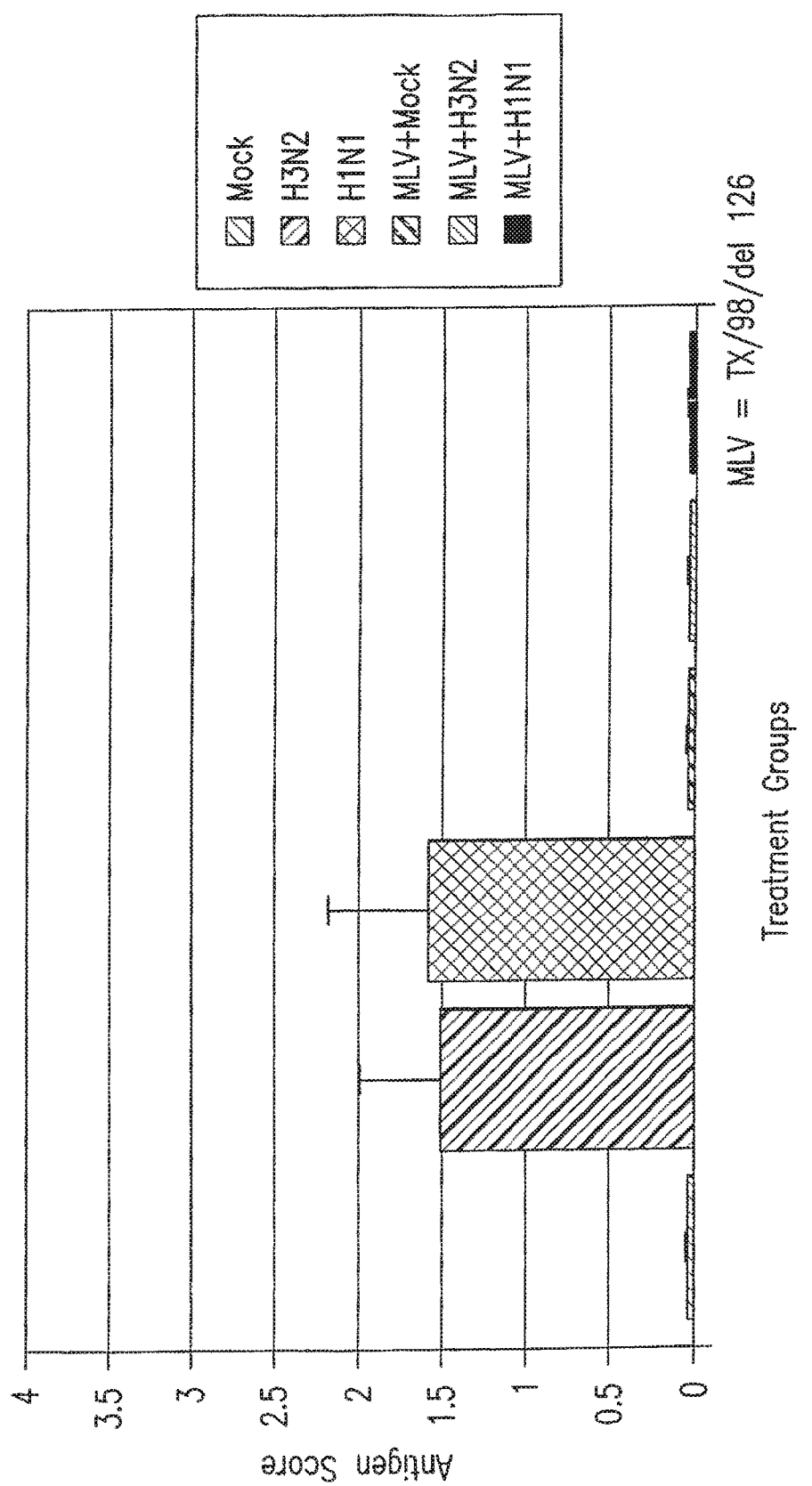
Figure 9:
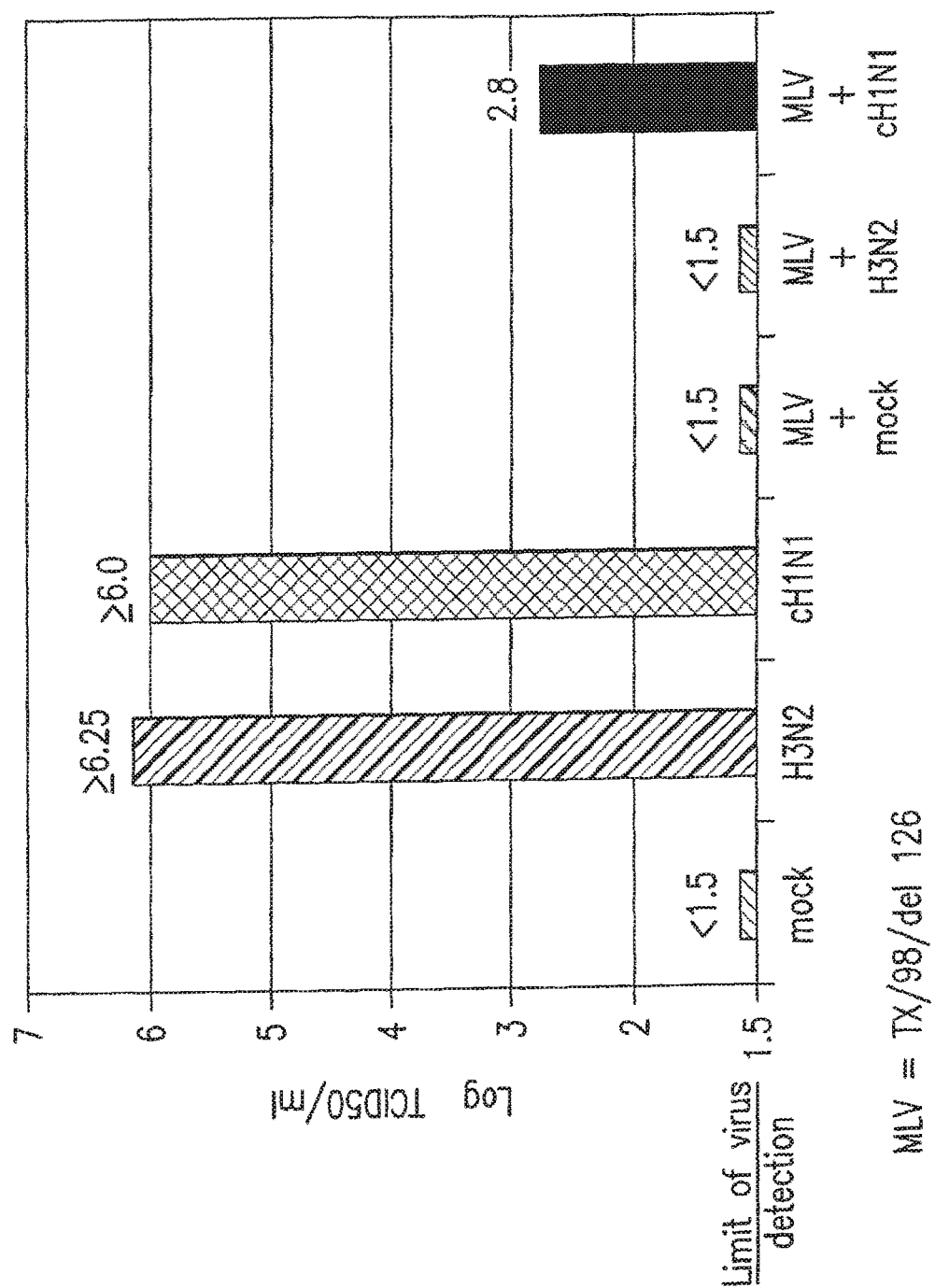

The following results were obtained 5 days after challenge:

1. Nonvaccinated, nonchallenged pigs did not have any histopathological changes and did not harbor influenza virus antigen in their lung tissues (FIGS. 7 and 8). Infectious virus was not present or below detection limits (FIG. 9).
2. Nonvaccinated pigs challenged with wild type H3N2 TX/98 virus showed significant histopathological damage and influenza viral antigen in their lung tissues (FIGS. 7 and 8). Virus titers in lung lavage was $\geq 10^{6.25}$ $TCID_{50}$/ml.
3. Nonvaccinated pigs challenged with wild type H1N1 MN/99 virus showed significant histopathological damage and influenza viral antigen in their lung tissues (FIGS. 7 and 8). Virus titers in lung lavage was $\geq 10^{6.0}$ $TCID_{50}$/ml.
4. Vaccinated, mock challenged pigs did not have any histopathological changes and did not harbor influenza virus antigen in their lung tissues (FIGS. 7 and 8). Infectious virus was not present or below detection limits (FIG. 9).
5. Vaccinated, H3N2 challenged pigs did not have any histopathological changes and did not harbor influenza virus antigen in their lung tissues (FIGS. 7 and 8). Infectious virus was not present or below detection limits (FIG. 9).
6. Vaccinated, H1N1 challenged pigs did have significantly less histopathological changes in their lung tissues compared to nonvaccinated, H1N1 challenged pigs ($p<0.001$). These pigs did not harbor influenza virus antigen in their lung tissues (FIGS. 7 and 8). There was significantly less ($p<0.001$) infectious virus present in the lung lavage when compared to the nonvaccinated H1N1 challenged animals (FIG. 9).

In summary, vaccination of pigs with the attenuated TX/98/del 126 mutant resulted in protective immunity against challenge with a homologous virus isolate (H3N2 A/Swine/Texas/4199-2/98 virus challenge). When vaccinated pigs were challenged with a virus belonging to a different influenza subtype (H1N1 A/Swine/MN/37866/99 virus challenge), this heterologous virus challenge resulted in significant less lesions in lung tissues and virus load in lung lavage when compared to the nonvaccinated controls at day 5 post inoculation.

These data indicate that attenuated TX/98/del 126 mutant has utility as a modified live virus vaccine showing protective immunity against homologous/homotypic challenge and considerable protection against heterologous/heterotypic challenge.

6.5 Equivalents

The present invention is not to be limited in scope by the specific embodiments described which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

Various references are cited herein, the disclosure of which are incorporated by reference in their entirety.

What is claimed is:

1. A method for preventing swine influenza virus disease in a pig, comprising administering to the pig an effective amount of an immunogenic composition comprising a genetically engineered attenuated swine influenza virus having an impaired interferon antagonist phenotype, wherein the virus comprises a swine influenza virus NS1 gene with a mutation resulting in a swine influenza virus NS1 protein having a deletion of between 90 and 94 amino acid residues from the carboxy-terminus of NS1.

2. The method of claim 1, wherein the swine influenza virus NS1 gene is from A/Swine/Texas/4199-2/98.

3. The method of claim 1, wherein the genetically engineered attenuated swine influenza virus is A/Swine/Texas/4199-2/98.

4. The method of claim 1, wherein the NS1 amino acids are counted on the basis of A/Swine/Texas/4199-2/98.

5. The method of claim 1, wherein the swine influenza virus is H1N1, H1N2, H3N2, H3N1, H9N2, or H5N1.

6. The method of claim 1, wherein the attenuated virus is a reassortant.

7. The method of claim 1, wherein the attenuated virus is a chimeric virus comprising a heterologous sequence.

8. The method of claim 1, wherein the attenuated virus is a chimeric virus that expresses an epitope of a foreign pathogen.

9. The method of claim 1, wherein the attenuated virus is engineered to express an epitope from a different virus or at least one segment derived from a different virus.

10. The method of claim 1, wherein the virus comprises a swine influenza virus NS1 gene with a mutation resulting in a swine influenza virus NS1 protein having a deletion of 90 amino acid residues from the carboxy-terminus of NS1.

11. The method of claim 10, wherein the swine influenza virus NS1 gene is from A/Swine/Texas/4199-2/98.

12. The method of claim 10, wherein the genetically engineered attenuated swine influenza virus is A/Swine/Texas/4199-2/98.

13. The method of claim 10, wherein the NS1 amino acids are counted on the basis of A/Swine/Texas/4199-2/98.

14. The method of claim 10, wherein the swine influenza virus is H1N1, H1N2, H3N2, H3N1, H9N2, or H5N1.

15. The method of claim 10, wherein the attenuated virus is a reassortant.

16. The method of claim 10, wherein the attenuated virus is a chimeric virus comprising a heterologous sequence.

17. The method of claim 10, wherein the attenuated virus is a chimeric virus that expresses an epitope of a foreign pathogen.

18. The method of claim 10, wherein the attenuated virus is engineered to express an epitope from a different virus or at least one segment derived from a different virus.

19. The method of claim 1, wherein said mutation in a swine influenza NS1 gene is in an NS1 gene from A/Swine/Colorado/1/77, A/Swine/Colorado/23619/99, A/Swine/Cote d'Armor/3633/84, A/Swine/Cote d'Armor/3633/84, A/Swine/England/195852/92, A/Swine/Finistere/2899/82, A/Swine/Hong Kong/10/98, A/Swine/Hong Kong/9/98, A/Swine/Hong Kong/81/78, A/Swine/Illinois/100084/01, A/Swine/Illinois/100085A/01, A/Swine/Illinois/21587/99, A/Swine/Indiana/1726/88, A/Swine/Indiana/9K035/99, A/Swine/Indiana/P12439/00, A/Swine/Iowa/30, A/Swine/Iowa/15/30, A/Swine/Iowa/533/99, A/Swine/Iowa/569/99, A/Swine/Iowa/3421/90, A/Swine/Iowa/8548-1/98, A/Swine/Iowa/930/01, A/Swine/Iowa/17672/88, A/Swine/Italy/1513-1/98, A/Swine/Italy/1523/98, A/Swine/Korea/CY02/02, A/Swine/Minnesota/55551/00, A/Swine/Minnesota/593/99, A/Swine/Minnesota/9088-2/98, A/Swine/Nebraska/1/92, A/Swine/Nebraska/209/98, A/Swine/Netherlands/12/85, A/Swine/North Carolina/16497/99, A/Swine/North Carolina/35922/98, A/Swine/North Carolina/93523/01, A/Swine/North Carolina/98225/01, A/Swine/Oedenrode/7C/96, A/Swine/Ohio/891/01, A/Swine/Oklahoma/18717/99, A/Swine/Oklahoma/18089/99, A/Swine/Ontario/01911-1/99, A/Swine/Ontario/01911-2/99, A/Swine/Ontario/41848/97, A/Swine/Ontario/97, A/Swine/Quebec/192/81, A/Swine/Quebec/192/91, A/Swine/Quebec/5393/91, A/Swine/Taiwan/7310/70, A/Swine/Tennessee/24/77, A/Swine/Texas/4199-2/98, A/Swine/Wisconsin/125/97, A/Swine/Wisconsin/136/97, A/Swine/Wisconsin/163/97, A/Swine/Wisconsin/164/97, A/Swine/Wisconsin/166/97, A/Swine/Wisconsin/168/97, A/Swine/Wisconsin/235/97, A/Swine/Wisconsin/238/97, A/Swine/Wisconsin/457/98, A/Swine/Wisconsin/458/98, A/Swine/Wisconsin/464/98 or A/Swine/Wisconsin/14094/99 swine influenza virus.

20. The method of claim 10, wherein said mutation in a swine influenza NS1 gene is in an NS1 gene from A/Swine/Colorado/1/77, A/Swine/Colorado/23619/99, A/Swine/Cote d'Armor/3633/84, A/Swine/Cote d'Armor/3633/84, A/Swine/England/195852/92, A/Swine/Finistere/2899/82, A/Swine/Hong Kong/10/98, A/Swine/Hong Kong/9/98, A/Swine/Hong Kong/81/78, A/Swine/Illinois/100084/01, A/Swine/Illinois/100085A/01, A/Swine/Illinois/21587/99, A/Swine/Indiana/1726/88, A/Swine/Indiana/9K035/99, A/Swine/Indiana/P12439/00, A/Swine/Iowa/30, A/Swine/Iowa/15/30, A/Swine/Iowa/533/99, A/Swine/Iowa/569/99, A/Swine/Iowa/3421/90, A/Swine/Iowa/8548-1/98, A/Swine/Iowa/930/01, A/Swine/Iowa/17672/88, A/Swine/Italy/1513-1/98, A/Swine/Italy/1523/98, A/Swine/Korea/CY02/02, A/Swine/Minnesota/55551/00, A/Swine/Minnesota/593/99, A/Swine/Minnesota/9088-2/98, A/Swine/Nebraska/1/92, A/Swine/Nebraska/209/98, A/Swine/Netherlands/12/85, A/Swine/North Carolina/16497/99, A/Swine/North Carolina/35922/98, A/Swine/North Carolina/93523/01, A/Swine/North Carolina/98225/01, A/Swine/Oedenrode/7C/96, A/Swine/Ohio/891/01, A/Swine/Oklahoma/18717/99, A/Swine/Oklahoma/18089/99, A/Swine/Ontario/01911-1/99, A/Swine/Ontario/01911-2/99, A/Swine/Ontario/41848/97, A/Swine/Ontario/97, A/Swine/Quebec/192/81, A/Swine/Quebec/192/91, A/Swine/Quebec/5393/91, A/Swine/Taiwan/7310/70, A/Swine/Tennessee/24/77, A/Swine/Texas/4199-2/98, A/Swine/Wisconsin/125/97, A/Swine/Wisconsin/136/97, A/Swine/Wisconsin/163/97, A/Swine/Wisconsin/164/97, A/Swine/Wisconsin/166/97, A/Swine/Wisconsin/168/97, A/Swine/Wisconsin/235/97, A/Swine/Wisconsin/238/97, A/Swine/Wisconsin/457/98, A/Swine/Wisconsin/458/98, A/Swine/Wisconsin/464/98 or A/Swine/Wisconsin/14094/99 swine influenza virus.

21. A method for immunizing a pig in need thereof against swine influenza virus, comprising administering to the pig an effective amount of an immunogenic composition comprising a genetically engineered attenuated swine influenza virus having an impaired interferon antagonist phenotype, wherein the virus comprises a swine influenza virus NS1 gene with a mutation resulting in a swine influenza virus NS1 protein having a deletion of between 90 and 94 amino acid residues from the carboxy-terminus of NS1.

22. A method for immunizing a pig in need thereof against swine influenza virus, comprising administering to the pig an effective amount of an immunogenic composition comprising a genetically engineered attenuated swine influenza virus having an impaired interferon antagonist phenotype, wherein the virus comprises a swine influenza virus NS1 gene with a mutation resulting in a swine influenza virus NS1 protein having a deletion of 90 amino acid residues from the carboxy-terminus of NS1.

23. The method of claim 21, wherein the swine influenza virus NS1 gene is from A/Swine/Texas/4199-2/98.

24. The method of claim 21, wherein the genetically engineered attenuated swine influenza virus is A/Swine/Texas/4199-2/98.

25. The method of claim 21, wherein the NS1 amino acids are counted on the basis of A/Swine/Texas/4199-2/98.

26. The method of claim 21, wherein the attenuated virus is a chimeric virus comprising a heterologous sequence.

27. The method of claim 21, wherein the attenuated virus is a chimeric virus that expresses an epitope of a foreign pathogen.

28. The method of claim 21, wherein the attenuated virus is engineered to express an epitope from a different virus or at least one segment derived from a different virus.

29. The method of claim 22, wherein the swine influenza virus NS1 gene is from A/Swine/Texas/4199-2/98.

30. The method of claim 22, wherein the genetically engineered attenuated swine influenza virus is A/Swine/Texas/4199-2/98.

31. The method of claim 22, wherein the NS1 amino acids are counted on the basis of A/Swine/Texas/4199-2/98.

32. The method of claim 22, wherein the attenuated virus is a chimeric virus comprising a heterologous sequence.

33. The method of claim 22, wherein the attenuated virus is a chimeric virus that expresses an epitope of a foreign pathogen.

34. The method of claim 22, wherein the attenuated virus is engineered to express an epitope from a different virus or at least one segment derived from a different virus.

* * * * *